US011851424B2

(12) United States Patent
Parent et al.

(10) Patent No.: US 11,851,424 B2
(45) Date of Patent: Dec. 26, 2023

(54) SOLID FORMS OF A MODULATOR OF HEMOGLOBIN

(71) Applicant: Global Blood Therapeutics, Inc., South San Francisco, CA (US)

(72) Inventors: Stephan D. Parent, West LAfayette, IN (US); Travis Lee Houston, Lafayette, IN (US); Courtney S. Johnson, West Lafayette, IN (US); Fang Wang, Foster City, CA (US)

(73) Assignee: GLOBAL BLOOD THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 17/744,537

(22) Filed: May 13, 2022

(65) Prior Publication Data

US 2022/0363674 A1     Nov. 17, 2022

Related U.S. Application Data

(60) Provisional application No. 63/188,833, filed on May 14, 2021.

(51) Int. Cl.
    *C07D 413/06*      (2006.01)

(52) U.S. Cl.
    CPC ........ *C07D 413/06* (2013.01); *C07B 2200/13* (2013.01)

(58) Field of Classification Search
    CPC .................... C07D 413/06; C07B 2200/13
    See application file for complete search history.

(56) References Cited

U.S. PATENT DOCUMENTS

10,683,285 B2 *   6/2020   Li ................. C07D 211/22
11,548,880 B2     1/2023   Li

FOREIGN PATENT DOCUMENTS

WO     WO 2020/106642 A1     5/2020

OTHER PUBLICATIONS

Brittain, H.G. (Ed.). (2009). Polymorphism in Pharmaceutical Solids (2nd ed.). CRC Press. https://doi.org/10.3109/9781420073225 (Year: 2009).*
CAIRA. Crystalline Polymorphism of Organic Compounds. Topics in Current Chemistry, Springer, Berlin, DE. 1998; 198:163-208.
International Search Report and Written Opinion dated Sep. 8, 2022 for PCT Application No. PCT/US2022/029289. 10 pages.

* cited by examiner

*Primary Examiner* — Brandon J Fetterolf
*Assistant Examiner* — Manahil Mirghani Ali Abdalhameed

(57) ABSTRACT

Forms of (S)-2-hydroxy-6-((4-(2-(2-hydroxyethyl)nicotinoyl)morpholin-3-yl)methoxy)benzaldehyde (Compound I), or salts or solvates thereof, were prepared and characterized in the solid state. Also provided are processes of manufacture and methods of using the forms of Compound I.

19 Claims, 54 Drawing Sheets

SOLID FORMS OF A MODULATOR OF HEMOGLOBIN

CROSS-REFERENCE TO RELATED APPLICATIONS

This application claims the benefit under 35 U.S.C. § 119(e) of U.S. Provisional Application No. 63/188,833, filed May 14, 2021, which is hereby incorporated by reference in its entirety.

FIELD

The present disclosure relates generally to solid forms of compounds that modulate hemoglobin, pharmaceutical compositions thereof, therapeutic uses thereof, and processes for making the solid forms.

BACKGROUND

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin A (HbA).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, making HbS susceptible to polymerization under hypoxic conditions to give the HbS containing red blood cells their characteristic sickle shape. The sickled cells are also more rigid than normal red blood cells, and their lack of flexibility can lead to blockage of blood vessels.

Compounds, such as Compound I, that modulate hemoglobin and are useful in treating disorders mediated by abnormal Hb (such as HbS) are disclosed in U.S. Pat. No. 10,683,285, the disclosure of which is hereby incorporated by reference in its entirety.

There remains a need for high purity solid forms of Compound I that are efficacious for the treatment of diseases modulated by hemoglobin.

SUMMARY

The present disclosure provides solid forms of Compound I of the formula:

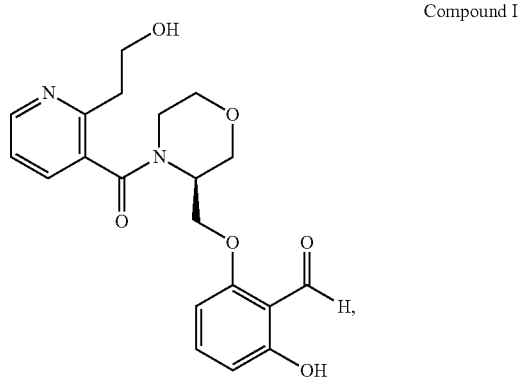

Compound I and salts and solvates thereof. Also described herein are processes for making the forms of Compound I, pharmaceutical compositions comprising solid forms of Compound I, and methods for using such forms and pharmaceutical compositions in the treatment of diseases modulated by hemoglobin.

DETAILED DESCRIPTION

Figure 1:
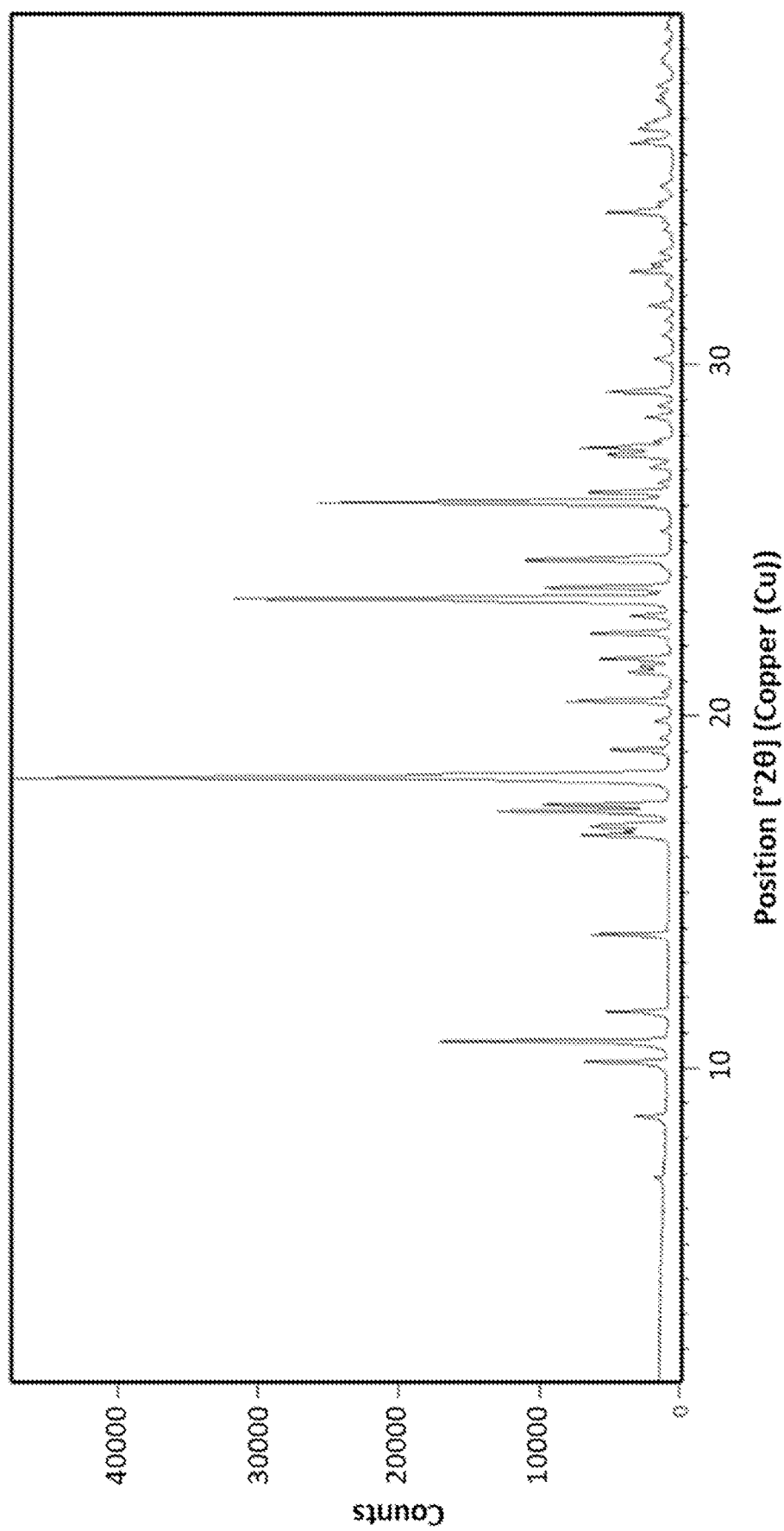
FIG. 1 shows an X-ray powder diffraction (XRPD) of Compound I Form I.

The compound (S)-2-hydroxy-6-((4-(2-(2-hydroxyethyl) nicotinoyl)morpholin-3-yl)methoxy)benzaldehyde, designated herein as Compound I, has the following formula:

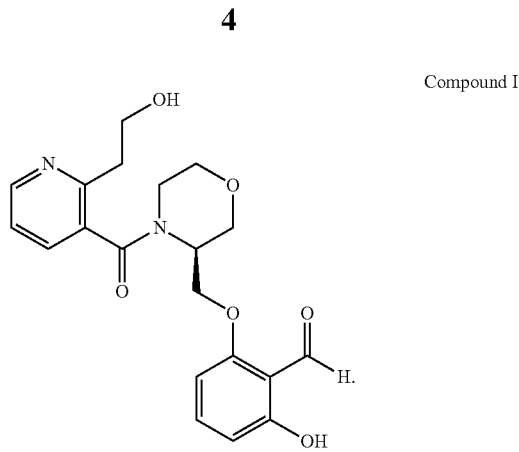

Compound I

Compound I is a modulator of hemoglobin. The synthesis and method of use thereof is described in U.S. Pat. No. 10,683,285, and U.S. Provisional Application No. 63/188,735 (filed on May 14, 2021, and titled "Methods of Making a Modulator of Hemoglobin"), and PCT Application No. PCT/US22/29304 (filed on even date herewith, and titled "Methods of Making a Modulator of Hemoglobin"), all of which are herein incorporated by reference in their entirety.

The present disclosure relates to various solid forms of Compound I and processes for making such solid forms. For instance, in some embodiments, solid forms of Compound I may include salts or solvates of Compound I. In some embodiments, solid forms of Compound I may include an amorphous form and is referred to herein as "amorphous Compound I."

The present disclosure relates to various crystalline forms of Compound I and processes for making the crystalline forms. Crystalline forms of Compound I described herein include "Compound I Form I" and "Compound I Material II." In some embodiments, such forms of Compound I may be anhydrous.

Additional crystalline forms of Compound I are also further described herein. In some embodiments, crystalline forms of Compound I may include a salt of Compound I. In some embodiments, a crystalline salt form of Compound I may be anhydrous or a solvate.

Some embodiments provide for a crystalline salt form, or solvate thereof, of Compound I:

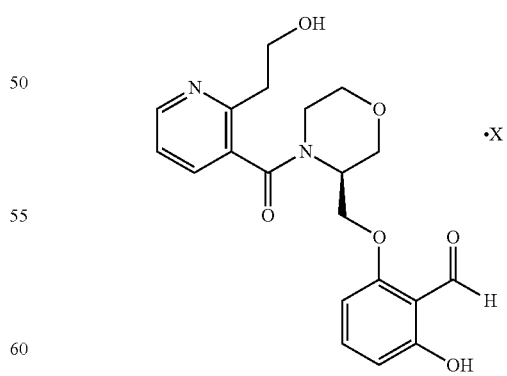

wherein X is benzenesulfonic acid, 1,2-ethanedisulfonic acid, ethanesulfonic acid, naphthalene-1,5-disulfonic acid, naphthalene-2-sulfonic acid, oxalic acid, sulfuric acid, or p-toluenesulfonic acid; and the ratio of Compound I to X is 1:1 or 2:1.

In some embodiments, X may be hydrochloric acid, benzenesulfonic acid, 1,2-ethanedisulfonic acid, ethanesulfonic acid, naphthalene-1,5-disulfonic acid, naphthalene-2-sulfonic acid, oxalic acid, sulfuric acid, or p-toluenesulfonic acid. The following exemplary forms are further described herein: "Compound I HCl Form A," "Compound I Besylate Form A," "Compound I Edisylate Form A," "Compound I Edisylate Material B," "Compound I Esylate Form A," "Compound I Esylate Form B," "Compound I Napadisylate Form A," "Compound I Napadisylate Material B," "Compound I Napsylate Form A," "Compound I Napsylate Material B," Compound I Oxalate Material A," "Compound I Oxalate Form B," "Compound I Sulfate Form A," and "Compound I Tosylate Form A."

In some embodiments, the crystalline salt form, or solvate thereof, is selected from the group consisting of: Compound I Besylate Form A, Compound I Edisylate Form A, Compound I Edisylate Material B, Compound I Esylate Form A, Compound I Esylate Form B, Compound I Napadisylate Form A, Compound I Napadisylate Material B, Compound I Napsylate Form A, Compound I Napsylate Material B, Compound I Oxalate Material A, Compound I Oxalate Form B, Compound I Sulfate Form A, and Compound I Tosylate Form A.

In some embodiments, provided is Compound I HCl Form A, Compound I Oxalate Form B, or Compound I Sulfate Form A.

1. Definitions

As used in the present specification, the following words and phrases are generally intended to have the meanings as set forth below, except to the extent that the context in which they are used indicates otherwise.

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds, and reference to "the assay" includes reference to one or more assays and equivalents thereof known to those skilled in the art.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±2.5%. In certain other embodiments, the term "about" includes the indicated amount±1%. Also, to the term "about X" includes description of "X".

Recitation of numeric ranges of values throughout the disclosure is intended to serve as a shorthand notation of referring individually to each separate value falling within the range inclusive of the values defining the range, and each separate value is incorporated in the specification as it were individually recited herein.

Forms of Compound I or salts or solvates thereof are provided herein. In some embodiments, reference to a form of Compound I or a salt or a solvate thereof means that at least 50% to 99% (e.g., at least 50%, at least 55%, at least 60%, at least 65%, at least 70%, at least 75%, at least 80%, at least 85%, at least 90%, at least 95%, or at least 99%) of Compound I or a salt or a solvate thereof present in a composition is in the designated form. For instance, in some embodiments, reference to Compound I Form I means that at least 50%, at least 55%, at least 60%, at least 65%, at least 70%, at least 75%, at least 80%, at least 85%, at least 90%, at least 95%, or at least 99% of Compound I present in a composition is in Form I.

The term "solid form" refers to a type of solid-state material that includes amorphous as well as crystalline forms. The term "crystalline form" refers to polymorphs as well as solvates, etc. The term "polymorph" refers to a particular crystal structure having particular physical properties such as X-ray diffraction, melting point, and the like.

The term "solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure.

The term "desolvated" refers to a Compound I form that is a solvate as described herein, and from which solvent molecules have been partially or completely removed. Desolvation techniques to produce desolvated forms include, without limitation, exposure of a Compound I form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (glass transition).

Any formula or structure given herein, including Compound I, is also intended to represent unlabeled forms as well as isotopically labeled forms of the compounds. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^{1}H$, $^{2}H$, $^{3}H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

"Pharmaceutically acceptable" or "physiologically acceptable" refer to forms as described herein, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the forms described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine and the like. In some embodiments, a pharmaceutically acceptable salt does not include a salt of a primary amine.

In some embodiments, the phrase "substantially shown in FIG." or "substantially shown in Figure" as applied to an X-ray powder diffractogram is meant to include a variation of ±0.2 °2θ or ±0.1 °2θ, as applied to DSC thermograms is meant to include a variation of ±3° Celsius, and as applied to thermogravimetric analysis (TGA) is meant to include a variation of ±2% in weight loss.

2. Forms of Compound I

As described generally above, the present disclosure provides crystalline forms of Compound I, and salts or solvates thereof. Additional forms (including amorphous forms) are also discussed further herein.

It is of note that the crystalline forms of Compound I, and salts or solvates thereof, and other forms (e.g., amorphous forms) of Compound I, and salts or solvates thereof, are collectively referred to herein as "forms of Compound I."

In some embodiments, Compound I is a salt. In some embodiments, Compound I is a pharmaceutically acceptable salt. In some embodiments, Compound I is a solvate. In some embodiments, Compound I is a salt or solvated salt.

In some embodiments, Compound I is an amorphous form.

Compound I Form I

It is contemplated that Compound I Form I is thermodynamically more stable, monotropically, relative to Compound I Material II.

The present disclosure provides, in some embodiments, a crystalline form of Compound I characterized by an X-ray powder diffractogram comprising the following peaks: 18.3, 23.4, and 26.1 °2θ±0.2 °2θ (Compound I Form I), as determined on a diffractometer using Cu-Kα radiation.

In some embodiments, the diffractogram of Compound I Form I further comprises one or more peaks at: 10.8 or 17.3 °2θ±0.2 °2θ.

In some embodiments, a crystalline form of Compound I is characterized by an X-ray powder diffractogram comprising the following peaks: 10.8 and 23.4 °2θ±0.2 °2θ (Compound I Form I), as determined on a diffractometer using Cu-Kα radiation. In some embodiments, a crystalline form of Compound I is characterized by an X-ray powder diffractogram comprising the following peaks: 10.8, 23.4, and 26.1 °2θ±0.2 °2θ (Compound I Form I), as determined on a diffractometer using Cu-Kα radiation. In some embodiments, the diffractogram of Compound I Form I further comprises one or more peaks at: 17.3, 17.5, or 23.7 °2θ±0.2 °2θ.

In some embodiments, Compound I Form I is characterized by the X-ray powder diffractogram as substantially shown in FIG. 1.

In some embodiments, Compound I Form I is characterized by a differential scanning calorimetry (DSC) curve that comprises an endotherm at about 111° C. (onset temperature). In some embodiments, Compound I Form I is characterized by the DSC curve as substantially shown in FIG. 2A.

Figure 3:
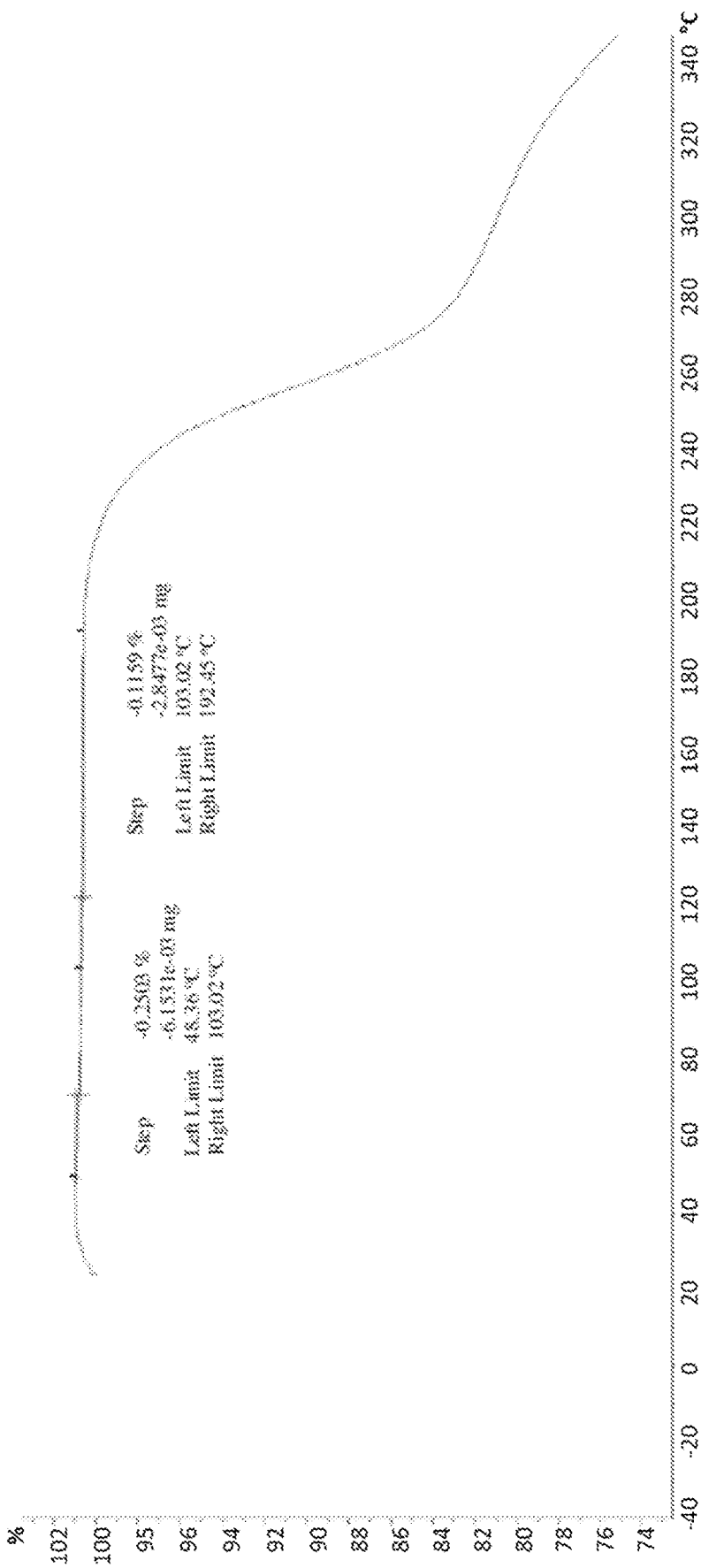
FIG. 3 shows a thermogravimetric analysis (TGA) of Compound I Form I.

In some embodiments, Compound I Form I is characterized by a thermogravimetric analysis (TGA) thermogram showing a negligible weight loss upon heating up to 192° C. In some embodiments, Compound I Form I is characterized by the thermogram as substantially shown in FIG. 3.

Some embodiments provide for Compound I Form I having unit cell parameters: a=5.50599(10) Å, b=16.4086(2) Å, c=20.4992(4) Å, α=90°, β=90°, and γ=90°.

In some embodiments, Compound I Form I has unit cell parameters: a=5.50599(10) Å, b=16.4086(2) Å, c=20.4992(4) Å, α=90°, β=90°, and γ=90° and volume=1852.02(5) Å$^3$. In some embodiments, Compound I Form I is characterized by one or more of the crystal structure parameters of Table 1.

Some embodiments provide for methods of making Compound I Form I. In some embodiments, a method of making Compound I Form I comprises:

combining Compound I and a solvent to form a mixture;
heating the mixture;
cooling the mixture to form a slurry;
filtering the slurry to obtain a solid; and
drying the solid to obtain Compound I Form I.

In some embodiments, the solvent is an organic solvent. In some embodiments, the organic solvent is ethyl acetate. In some embodiments, the organic solvent is acetonitrile. In some embodiments, the organic solvent is acetone. In some embodiments, the organic solvent is a mixture of acetone and methyl tert-butyl ether (MTBE).

In some embodiments, heating the mixture comprises heating the mixture until Compound I is dissolved in the mixture such that the mixture is a clear solution. In some embodiments, heating the mixture further comprises adding a second solvent (while heating). In some embodiments, the second solvent is MTBE. In some embodiments, cooling the mixture to form a slurry comprises cooling the mixture to ambient temperature. In some embodiments, cooling the mixture to form a slurry comprises cooling the mixture to ambient temperature and stirring for about 18-24 hours. In some embodiments, cooling the mixture comprises adding a third solvent. In some embodiments, the third solvent is MTBE. In some embodiments, drying the solid comprises drying under vacuum at about 45° C. to about 55° C.

Compound I Material II (Also Referred to as Compound I Form II)

The present disclosure provides, in some embodiments, a crystalline form of Compound I characterized by an X-ray powder diffractogram comprising the following peaks: 14.9, 16.7, and 22.9 °2θ±0.2 °2θ (Compound I Material II), as determined on a diffractometer using Cu-Kα radiation.

In some embodiments, the diffractogram of Compound I Material II further comprises one or more peaks at: 18.4 or 19.2 °2θ±0.2 °2θ.

In some embodiments, a crystalline form of Compound I is characterized by an X-ray powder diffractogram comprising the following peaks: 14.9, 22.6, and 25.8 °2θ±0.2 °2θ (Compound I Material II), as determined on a diffractometer using Cu-Kα radiation. In some embodiments, the diffractogram of Compound I Material II further comprises one or more peaks at: 18.6, 19.6, or 20.2 °2θ±0.2 °2θ.

Figure 5:
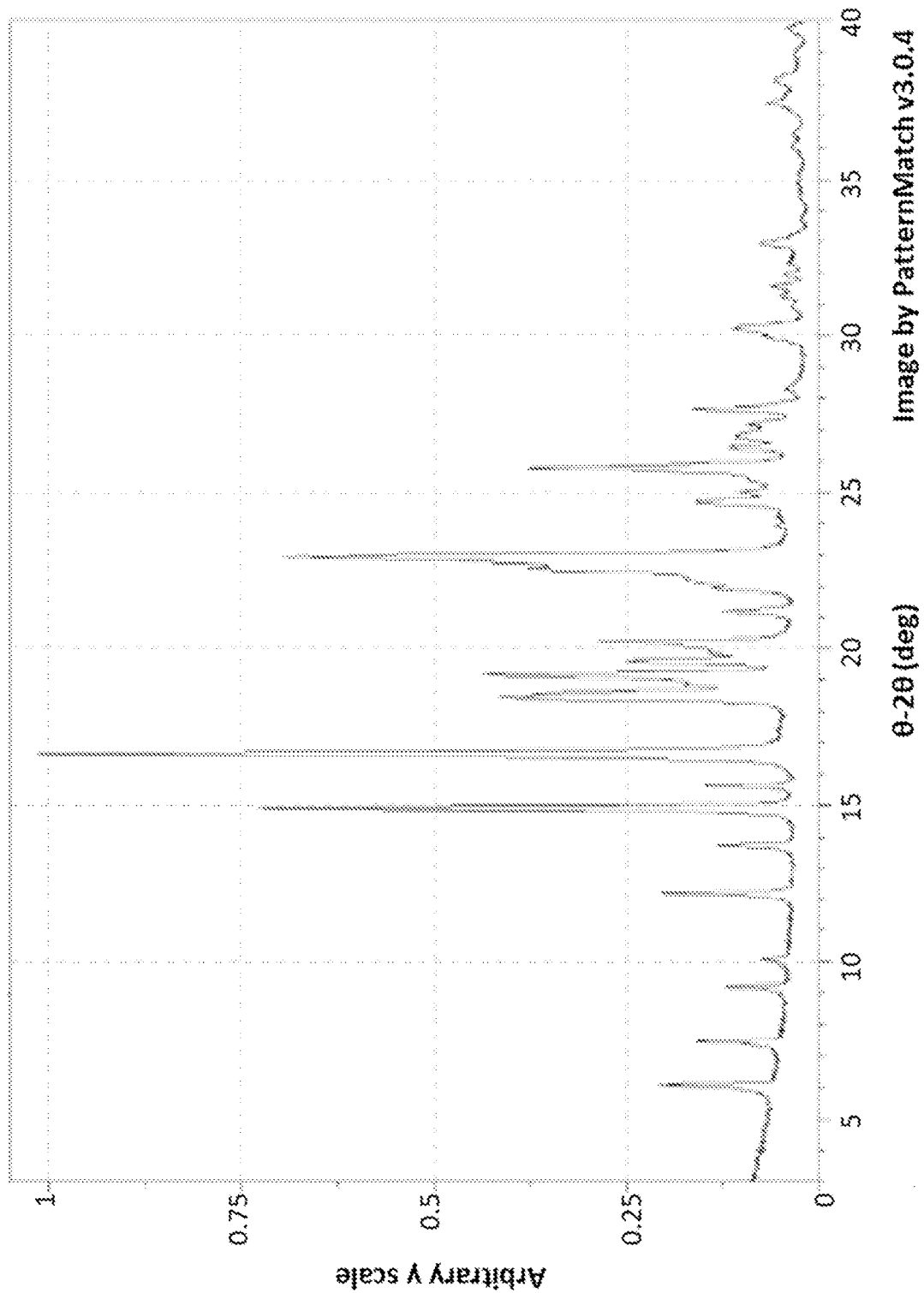
FIG. 5 shows an X-ray powder diffraction (XRPD) of Compound I Material II.

In some embodiments, Compound I Material II is characterized by the X-ray powder diffractogram as substantially shown in FIG. 5.

In some embodiments, Compound I Material II is characterized by a differential scanning calorimetry (DSC) curve that comprises an endotherm at about 102° C. (onset temperature). In some embodiments, Compound I Material II is characterized by the DSC curve as substantially shown in FIG. 6.

Figure 7:
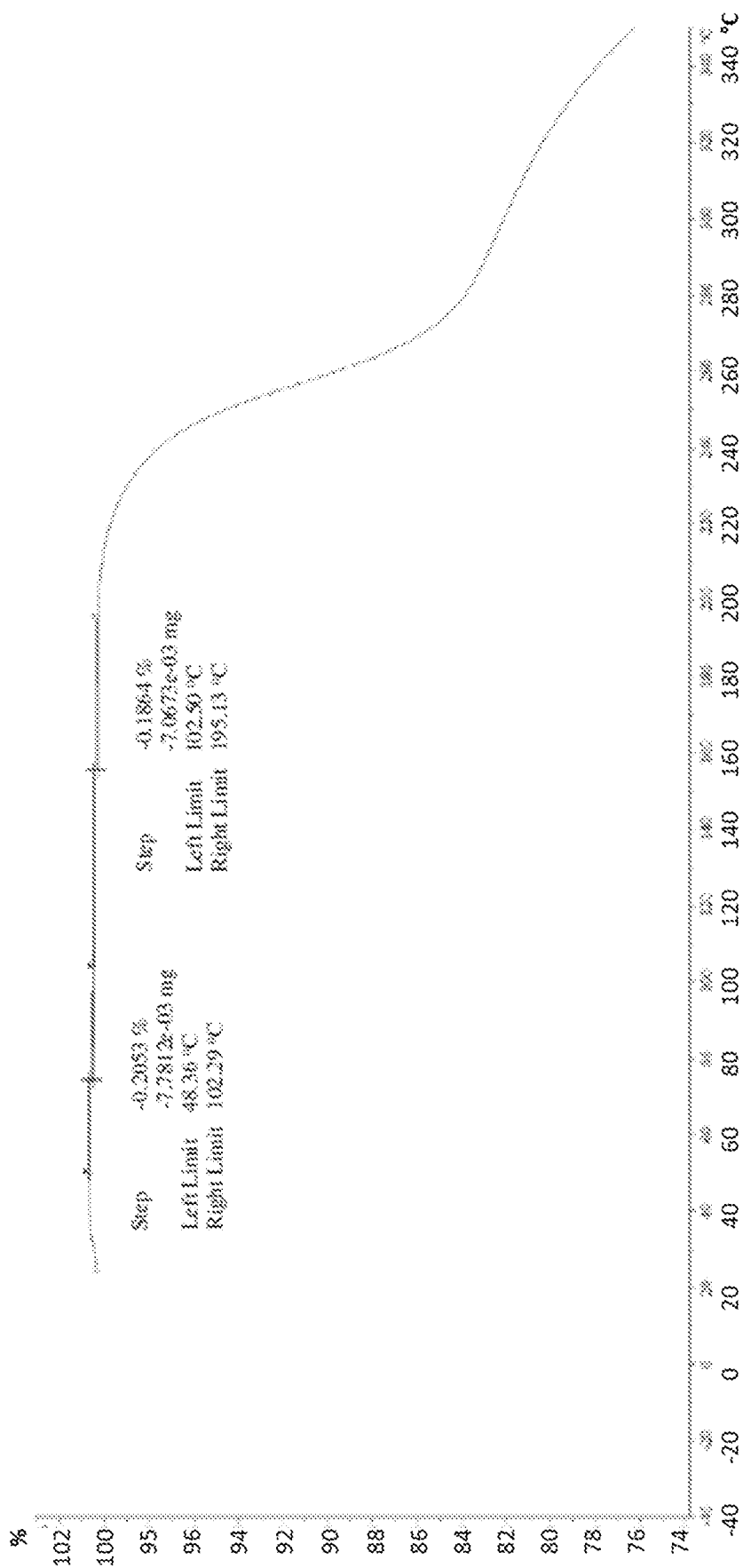
FIG. 7 shows a thermogravimetric analysis (TGA) of Compound I Material II.

In some embodiments, Compound I Material II is characterized by a thermogravimetric analysis (TGA) thermogram showing negligible weight loss upon heating up to 195° C. In some embodiments, Compound I Material II is characterized by the thermogram as substantially shown in FIG. 7.

Compound I HCl Form A

The present disclosure provides, in some embodiments, a crystalline salt form of Compound I having the formula:

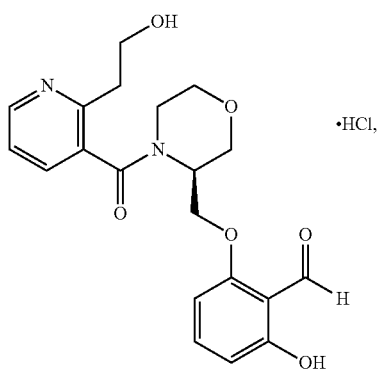

Compound I HCl characterized by an X-ray powder diffractogram comprising the following peaks: 12.7, 16.4, and 23.5 °2θ±0.2 °2θ (Compound I HCl Form A), as determined on a diffractometer using Cu-Kα radiation.

Figure 9:
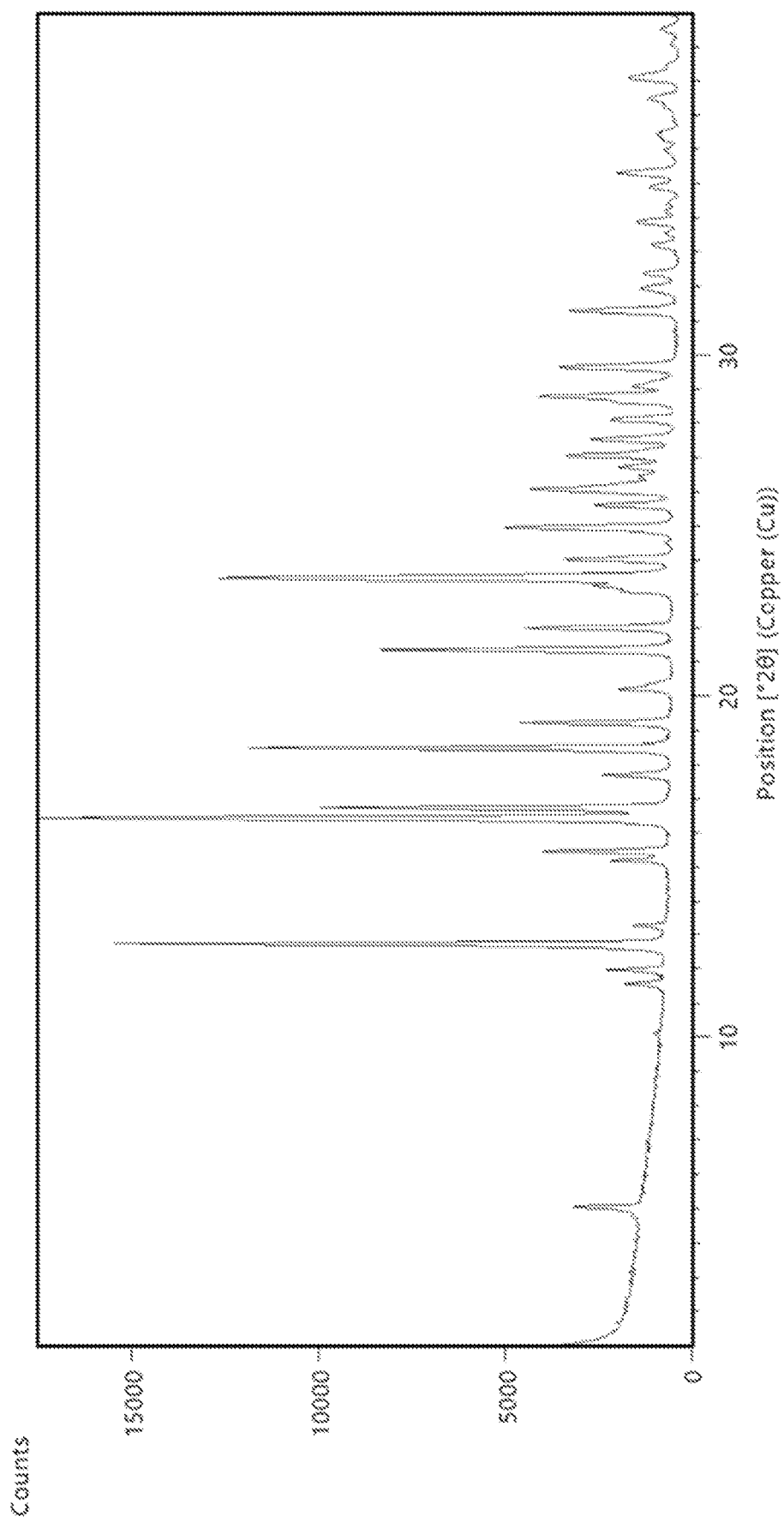
FIG. 9 shows an X-ray powder diffraction (XRPD) of Compound I HCl Form A.

In some embodiments, the diffractogram of Compound I HCl Form A further comprises one or more peaks at: 16.7 or 18.5 °2θ±0.2 °2θ. In some embodiments, Compound I HCl Form A is characterized by the X-ray powder diffractogram as substantially shown in FIG. 9.

In some embodiments, Compound I HCl Form A is characterized by a differential scanning calorimetry (DSC) curve that comprises an endotherm at about 193° C. (onset temperature). In some embodiments, Compound I HCl Form A is characterized by the DSC curve as substantially shown in FIG. 10.

In some embodiments, Compound I HCl Form A is characterized by a thermogravimetric analysis (TGA) thermogram showing a 0.6% weight loss upon heating up to 188° C. In some embodiments, Compound I HCl Form A is characterized by the thermogram as substantially shown in FIG. 11.

Some embodiments provide for Compound I HCl Form A having unit cell parameters: a=7.72088(10) Å, b=7.57161(10) Å, c=17.6273(2) Å, α=90°, β=98.0066(12)°, and γ=90°.

In some embodiments, Compound I HCl Form A has unit cell parameters: a=7.72088(10) Å, b=7.57161(10) Å, c=17.6273(2) Å, α=90°, β=98.0066(12)°, and γ=90° and volume=1022.44(2) Å$^3$.

In some embodiments, Compound I HCl Form A is characterized by one or more of the crystal structure parameters of Table 3.

Compound I Besylate Form A

The present disclosure provides, in some embodiments, a crystalline form (S)-2-hydroxy-6-((4-(2-(2-hydroxyethyl)nicotinoyl)morpholin-3-yl)methoxy)benzaldehyde besylate ("Compound I Besylate Form A" or "Besylate Form A") characterized by an X-ray powder diffractogram comprising the following peaks: 4.93, 17.0, 18.5, and 19.2 °2θ±0.2 °2θ, as determined on a diffractometer using Cu-Kα radiation. In some embodiments, the diffractogram of Compound I Besylate Form A further comprises one or more peaks at: 15.7 and 22.4 °2θ±0.2 °2θ. In some embodiments, Compound I Besylate Form A is characterized by the X-ray powder diffractogram as substantially shown in FIG. 17.

In some embodiments, Compound I Besylate Form A is characterized by a differential scanning calorimetry (DSC) curve that comprises an endotherm at about 114° C. (peak temperature). In some embodiments, Compound I Besylate Form A is characterized by a differential scanning calorimetry (DSC) curve that comprises an endotherm at about 130° C. (peak temperature). In some embodiments, Compound I Besylate Form A is characterized by the DSC curve as substantially shown in FIG. 18.

In some embodiments, Compound I Besylate Form A is characterized by a thermogravimetric analysis (TGA) thermogram showing a weight loss of about 3.9% up to 145° C. In some embodiments, Compound I Besylate Form A is characterized by a thermogravimetric analysis (TGA) thermogram showing a weight loss of about 6.6% from 145° C. to 211° C. In some embodiments, Compound I Besylate Form A is characterized by the thermogram as substantially shown in FIG. 19.

Compound I Edisylate Form A

The present disclosure provides, in some embodiments, a crystalline form (S)-2-hydroxy-6-((4-(2-(2-hydroxyethyl)nicotinoyl)morpholin-3-yl)methoxy)benzaldehyde edisylate ("Compound I Edisylate Form A" or "Edisylate Form A") characterized by an X-ray powder diffractogram comprising the following peaks: 11.5, 18.6, and 23.9 °2θ±0.2 °2θ, as determined on a diffractometer using Cu-Kα radiation. In some embodiments, the diffractogram of Compound I Edisylate Form A further comprises one or more peaks at: 4.99 and 21.1 °2θ±0.2 °2θ. In some embodiments, Compound I Edisylate Form A is characterized by the X-ray powder diffractogram as substantially shown in FIG. 20.

Figure 21:
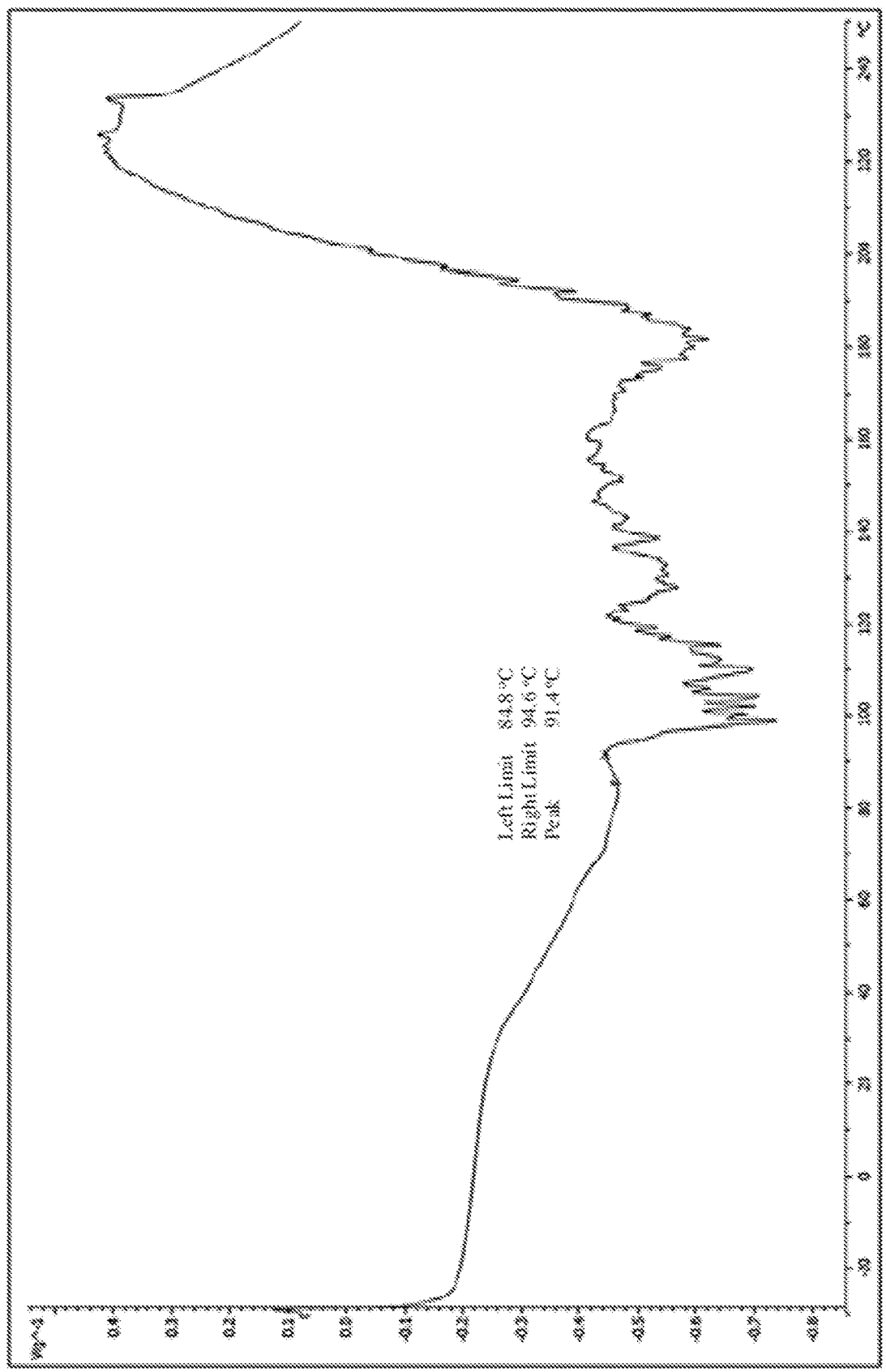
FIG. 21 shows a differential scanning calorimeter (DSC) curve of Compound I Edisylate Form A.

In some embodiments, Compound I Edisylate Form A is characterized by a differential scanning calorimetry (DSC) curve that comprises an endotherm at about 91.4° C. (peak temperature). In some embodiments, Compound I Edisylate Form A is characterized by the DSC curve as substantially shown in FIG. 21.

Figure 22:
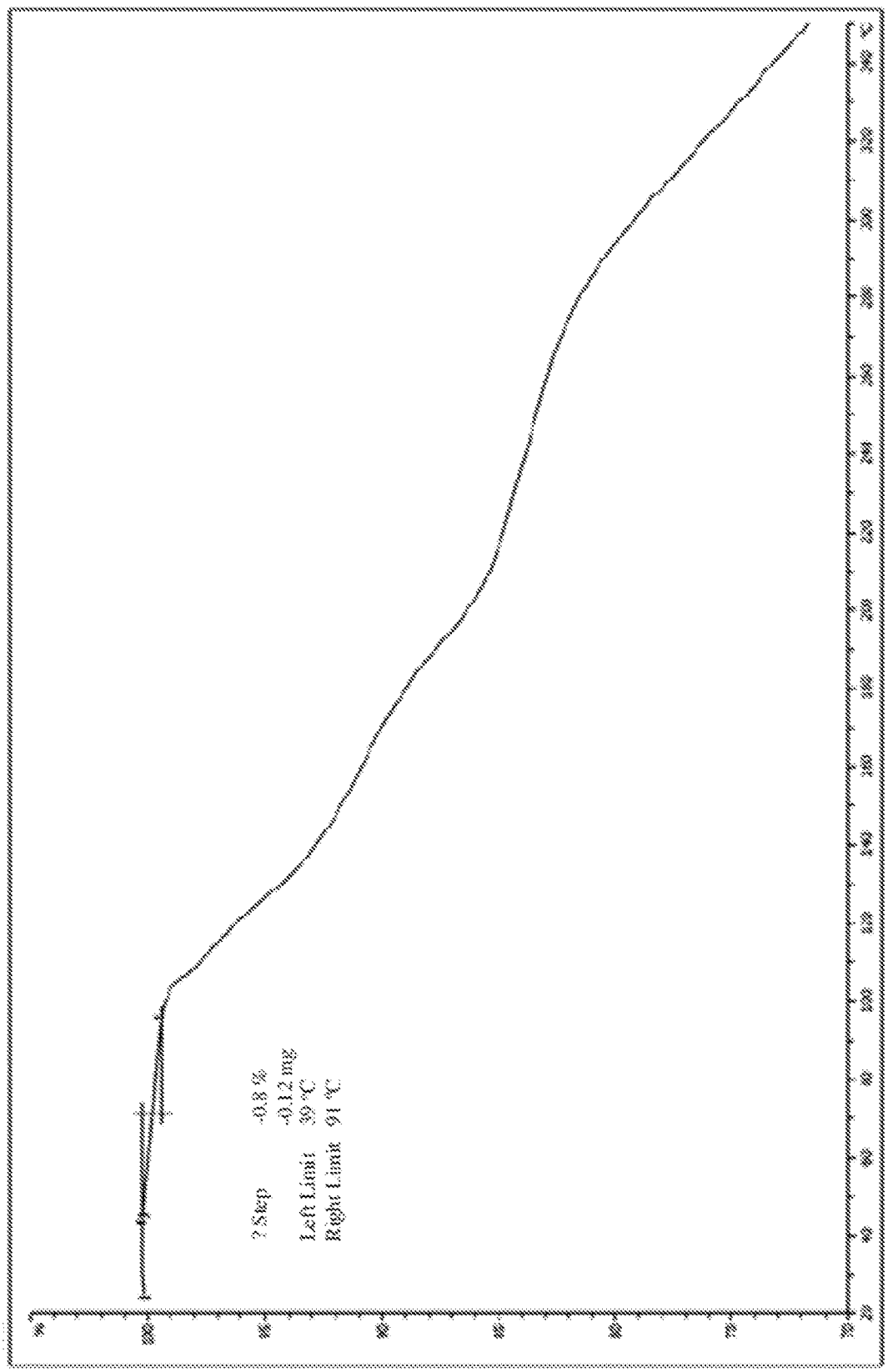
FIG. 22 shows a thermogravimetric analysis (TGA) of Compound I Edisylate Form A.

In some embodiments, Compound I Edisylate Form A is characterized by a thermogravimetric analysis (TGA) thermogram showing a weight loss of about 0.8% up to 91° C. In some embodiments, Compound I Edisylate Form A is characterized by the thermogram as substantially shown in FIG. 22.

Compound I Edisylate Material B

The present disclosure provides, in some embodiments, a crystalline form (S)-2-hydroxy-6-((4-(2-(2-hydroxyethyl)nicotinoyl)morpholin-3-yl)methoxy)benzaldehyde edisylate ("Compound I Edisylate Material B" or "Edisylate Material B") characterized by an X-ray powder diffractogram comprising the following peaks: 14.6, 22.6, and 23.9 °2θ±0.2 °2θ, as determined on a diffractometer using Cu-Kα radiation. In some embodiments, the diffractogram of Compound I Edisylate Material B further comprises one or more peaks at: 19.0 and 26.7 °2θ±0.2 °2θ. In some embodiments, Compound I Edisylate Material B is characterized by the X-ray powder diffractogram as substantially shown in FIG. 23.

In some embodiments, Compound I Edisylate Material B is characterized by a differential scanning calorimetry (DSC) curve that comprises an endotherm at about 118° C. (peak temperature). In some embodiments, Compound I Edisylate Material B is characterized by a differential scanning calorimetry (DSC) curve that comprises an endotherm at about 187° C. (peak temperature). In some embodiments, Compound I Edisylate Material B is characterized by a differential scanning calorimetry (DSC) curve that comprises an endotherm at about 208° C. (peak temperature). In some embodiments, Compound I Edisylate Material B is characterized by the DSC curve as substantially shown in FIG. 24.

In some embodiments, Compound I Edisylate Material B is characterized by a thermogravimetric analysis (TGA) thermogram showing a weight loss of about 1.1% up to 204° C. In some embodiments, Compound I Edisylate Material B is characterized by the thermogram as substantially shown in FIG. 25.

Compound I Esylate Form A

The present disclosure provides, in some embodiments t, a crystalline form (S)-2-hydroxy-6-((4-(2-(2-hydroxyethyl)nicotinoyl)morpholin-3-yl)methoxy)benzaldehyde esylate ("Compound I Esylate Form A" or "Esylate Form A") characterized by an X-ray powder diffractogram comprising the following peaks: 18.5, 19.2, and 22.5 °2θ±0.2 °2θ, as determined on a diffractometer using Cu-Kα radiation. In some embodiments, the diffractogram of Compound I Esylate Form A further comprises one or more peaks at: 11.2 and 21.4 °2θ±0.2 °2θ. In some embodiments, Compound I Esylate Form A is characterized by the X-ray powder diffractogram as substantially shown in FIG. 26.

In some embodiments, Compound I Esylate Form A is characterized by a differential scanning calorimetry (DSC) curve that comprises an endotherm at about 49.6° C. (peak temperature). In some embodiments, Compound I Esylate Form A is characterized by a differential scanning calorimetry (DSC) curve that comprises an endotherm at about 100° C. (peak temperature). In some embodiments, Compound I Esylate Form A is characterized by a differential scanning calorimetry (DSC) curve that comprises an endotherm at about 172° C. (peak temperature). In some embodiments, Compound I Esylate Form A is characterized by the DSC curve as substantially shown in FIG. 27.

In some embodiments, Compound I Esylate Form A is characterized by a thermogravimetric analysis (TGA) thermogram showing a weight loss of about 3.8% up to 91° C. In some embodiments, Compound I Esylate Form A is characterized by a thermogravimetric analysis (TGA) thermogram showing a weight loss of about 17.6% from 93° C. to 170° C. In some embodiments, Compound I Esylate Form A is characterized by the thermogram as substantially shown in FIG. 28.

Compound I Esylate Form B

The present disclosure provides, in some embodiments, a crystalline form (S)-2-hydroxy-6-((4-(2-(2-hydroxyethyl)nicotinoyl)morpholin-3-yl)methoxy)benzaldehyde esylate ("Compound I Esylate Form B" or "Esylate Form B") characterized by an X-ray powder diffractogram comprising the following peaks: 5.52, 19.8, and 22.7 °2θ±0.2 °2θ, as determined on a diffractometer using Cu-Kα radiation. In some embodiments, the diffractogram of Compound I Esylate Form B further comprises one or more peaks at: 10.8 and 16.8 °2θ±0.2 °2θ. In some embodiments, Compound I Esylate Form B is characterized by the X-ray powder diffractogram as substantially shown in FIG. 29.

In some embodiments, Compound I Esylate Form B is characterized by a differential scanning calorimetry (DSC) curve that comprises an endotherm at about 97.0° C. (onset temperature). In some embodiments, Compound I Esylate Form B is characterized by the DSC curve as substantially shown in FIG. 30.

In some embodiments, Compound I Esylate Form B is characterized by a thermogravimetric analysis (TGA) thermogram showing a weight loss of about 2.6% up to 117° C. In some embodiments, Compound I Esylate Form B is characterized by the thermogram as substantially shown in FIG. 31.

Compound I Napadisylate Form A

The present disclosure provides, in some embodiments, a crystalline form (S)-2-hydroxy-6-((4-(2-(2-hydroxyethyl)nicotinoyl)morpholin-3-yl)methoxy)benzaldehyde napadisylate ("Compound I Napadisylate Form A" or "Napadisylate Form A") characterized by an X-ray powder diffractogram comprising the following peaks: 5.26, 10.6, 12.1, and 17.8 °2θ±0.2 °2θ, as determined on a diffractometer using Cu-Kα radiation. In some embodiments, the diffractogram of Compound I Napadisylate Form A further comprises one or more peaks at: 19.5 and 20.7 °2θ±0.2 °2θ. In some embodiments, Compound I Napadisylate Form A is characterized by the X-ray powder diffractogram as substantially shown in FIG. 32.

In some embodiments, Compound I Napadisylate Form A is characterized by a differential scanning calorimetry (DSC) curve that comprises an endotherm at about 69.8° C. (peak temperature). In some embodiments, Compound I Napadisylate Form A is characterized by a differential scanning calorimetry (DSC) curve that comprises an endotherm at about 151° C. (peak temperature). In some embodiments, Compound I Napadisylate Form A is characterized by a differential scanning calorimetry (DSC) curve that comprises an endotherm at about 198° C. (peak temperature). In some embodiments, Compound I Napadisylate Form A is characterized by the DSC curve as substantially shown in FIG. 33.

Figure 34:
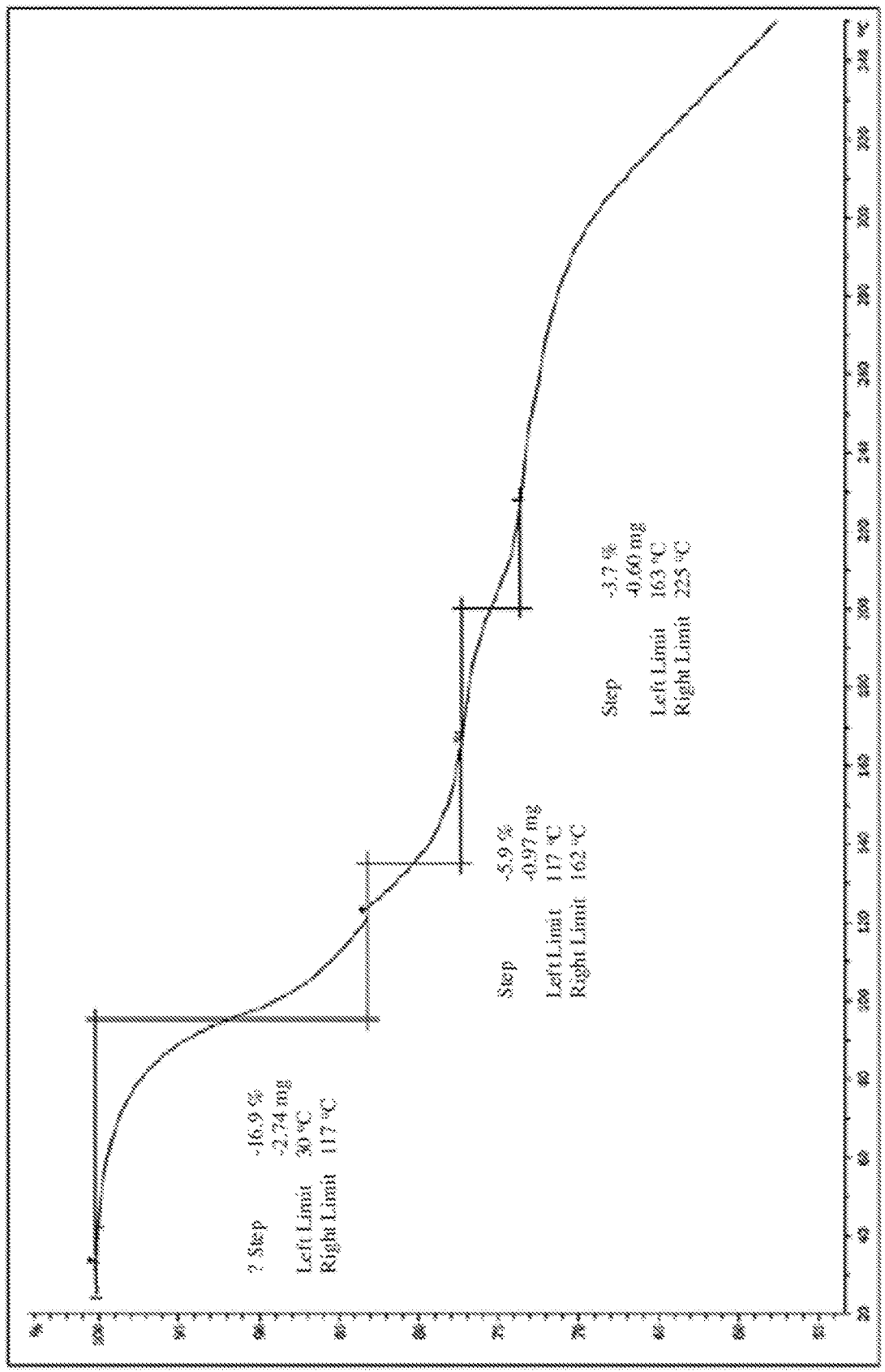
FIG. 34 shows a thermogravimetric analysis (TGA) of Compound I Napadisylate Form A.

In some embodiments, Compound I Napadisylate Form A is characterized by a thermogravimetric analysis (TGA) thermogram showing a weight loss of about 16.9% up to 117° C. In some embodiments, Compound I Napadisylate Form A is characterized by a thermogravimetric analysis (TGA) thermogram showing a weight loss of about 5.9% from 117° C. to 162° C. In some embodiments, Compound I Napadisylate Form A is characterized by a thermogravimetric analysis (TGA) thermogram showing a weight loss of about 3.7% from 163° C. to 225° C. In some embodiments, Compound I Napadisylate Form A is characterized by the thermogram as substantially shown in FIG. 34.

Compound I Napadisylate Material B

The present disclosure provides, in some embodiments, a crystalline form (S)-2-hydroxy-6-((4-(2-(2-hydroxyethyl)nicotinoyl)morpholin-3-yl)methoxy)benzaldehyde napadisylate ("Compound I Napadisylate Material B" or "Napadisylate Material B") characterized by an X-ray powder diffractogram comprising the following peaks: 5.02, 10.4, 18.1 °2θ±0.2 °2θ, as determined on a diffractometer using Cu-Kα radiation. In some embodiments, the diffractogram of Compound I Napadisylate Material B further comprises one or more peaks at: 20.2 and 20.9 °2θ±0.2 °2θ. In some embodiments, Compound I Napadisylate Material B is characterized by the X-ray powder diffractogram as substantially shown in FIG. 35.

In some embodiments, Compound I Napadisylate Material B is characterized by a differential scanning calorimetry (DSC) curve that comprises an endotherm at about 77.1° C. (peak temperature). In some embodiments, Compound I Napadisylate Material B is characterized by a differential scanning calorimetry (DSC) curve that comprises an endotherm at about 158° C. (peak temperature). In some embodiments, Compound I Napadisylate Material B is characterized by the DSC curve as substantially shown in FIG. 36.

In some embodiments, Compound I Napadisylate Material B is characterized by a thermogravimetric analysis (TGA) thermogram showing a weight loss of about 5.5% up to 162° C. In some embodiments, Compound I Napadisylate Material B is characterized by the thermogram as substantially shown in FIG. 37.

Compound I Napsylate Form A

The present disclosure provides, in some embodiments, a crystalline form (S)-2-hydroxy-6-((4-(2-(2-hydroxyethyl)nicotinoyl)morpholin-3-yl)methoxy)benzaldehyde napsylate ("Compound I Napsylate Form A" or "Napsylate Form A") characterized by an X-ray powder diffractogram comprising the following peaks: 15.0, 20.0, and 24.0 °2θ±0.2 °2θ, as determined on a diffractometer using Cu-Kα radiation. In some embodiments, the diffractogram of Compound I Napsylate Form A further comprises one or more peaks at: 15.1 and 17.4 °2θ±0.2 °2θ. In some embodiments, Compound I Napsylate Form A is characterized by the X-ray powder diffractogram as substantially shown in FIG. 38.

Compound I Napsylate Material B

The present disclosure provides, in some embodiments, a crystalline form (S)-2-hydroxy-6-((4-(2-(2-hydroxyethyl)nicotinoyl)morpholin-3-yl)methoxy)benzaldehyde napsylate ("Compound I Napsylate Material B" or "Napsylate Material B") characterized by an X-ray powder diffractogram comprising the following peaks: 4.30, 18.5, and 19.0 °2θ±0.2 °2θ, as determined on a diffractometer using Cu-Kα radiation. In some embodiments, the diffractogram of Compound I Napsylate Material B further comprises one or more peaks at: 10.7 and 21.5 °2θ±0.2 °2θ. In some embodiments, Compound I Napsylate Material B is characterized by the X-ray powder diffractogram as substantially shown in FIG. 39.

In some embodiments, Compound I Napsylate Material B is characterized by a differential scanning calorimetry (DSC) curve that comprises an endotherm at about 52.0° C. (peak temperature). In some embodiments, Compound I Napsylate Material B is characterized by a differential scanning calorimetry (DSC) curve that comprises an endotherm at about 111° C. (peak temperature). In some embodiments, Compound I Napsylate Material B is characterized by a differential scanning calorimetry (DSC) curve that comprises an endotherm at about 177° C. (peak temperature). In some embodiments, Compound I Napsylate Material B is characterized by the DSC curve as substantially shown in FIG. 40.

In some embodiments, Compound I Napsylate Material B is characterized by a thermogravimetric analysis (TGA) thermogram showing a weight loss of about 3.0% up to 117° C. In some embodiments, Compound I Napsylate Material B is characterized by the thermogram as substantially shown in FIG. 41.

Compound I Oxalate Material A

The present disclosure provides, in some embodiments, a crystalline form (S)-2-hydroxy-6-((4-(2-(2-hydroxyethyl)nicotinoyl)morpholin-3-yl)methoxy)benzaldehyde oxalate ("Compound I Oxalate Material A" or "Oxalate Material A") characterized by an X-ray powder diffractogram comprising the following peaks: 10.7, 11.6, and 16.9 °2θ±0.2 °2θ, as determined on a diffractometer using Cu-Kα radiation. In some embodiments, the diffractogram of Compound I Oxalate Material A further comprises one or more peaks at: 10.9 and 21.6 °2θ±0.2 °2θ. In some embodiments, Compound I Oxalate Material A is characterized by the X-ray powder diffractogram as substantially shown in FIG. 42.

In some embodiments, Compound I Oxalate Material A is characterized by a differential scanning calorimetry (DSC) curve that comprises an endotherm at about 67.6° C. (peak temperature). In some embodiments, Compound I Oxalate Material A is characterized by a differential scanning calorimetry (DSC) curve that comprises an endotherm at about 111° C. (onset temperature). In some embodiments, Compound I Oxalate Material A is characterized by the DSC curve as substantially shown in FIG. 43.

In some embodiments, Compound I Oxalate Material A is characterized by a thermogravimetric analysis (TGA) thermogram showing a weight loss of about 1.3% up to 122° C. In some embodiments, Compound I Oxalate Material A is characterized by the thermogram as substantially shown in FIG. 44.

Compound I Oxalate Form B

Figure 45:
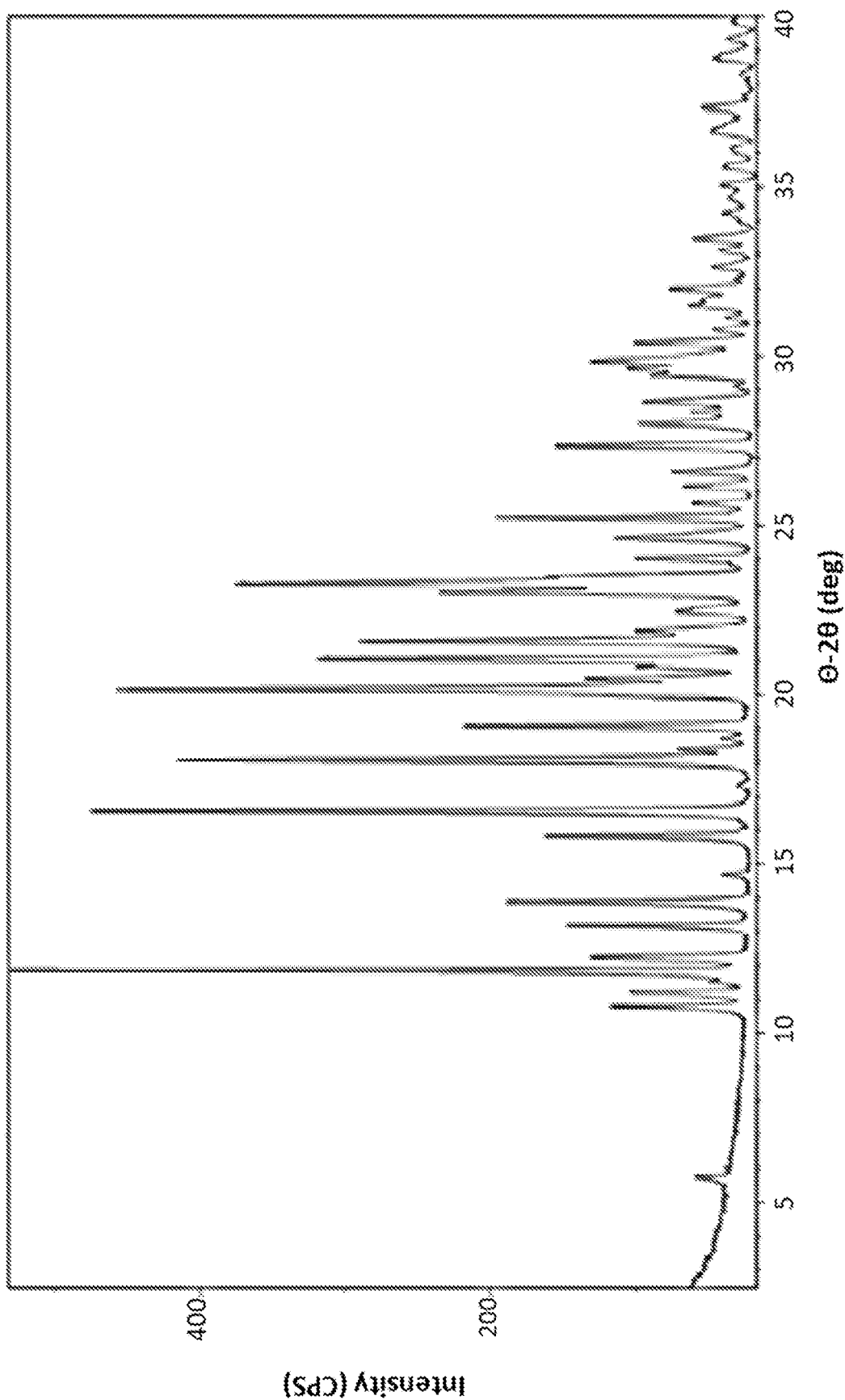
FIG. 45 shows an X-ray powder diffraction (XRPD) of Compound I Oxalate Form B.

The present disclosure provides, in some embodiments, a crystalline form (S)-2-hydroxy-6-((4-(2-(2-hydroxyethyl)nicotinoyl)morpholin-3-yl)methoxy)benzaldehyde oxalate ("Compound I Oxalate Form B" or "Oxalate Form B") characterized by an X-ray powder diffractogram comprising the following peaks: 11.9, 16.6, and 20.2 °2θ±0.2 °2θ, as determined on a diffractometer using Cu-Kα radiation. In some embodiments, the diffractogram of Compound I Oxalate Form B further comprises one or more peaks at: 18.1 and 23.3 °2θ±0.2 °2θ. In some embodiments, Compound I Oxalate Form B is characterized by the X-ray powder diffractogram as substantially shown in FIG. 45.

In some embodiments, Compound I Oxalate Form B is characterized by a differential scanning calorimetry (DSC) curve that comprises an endotherm at about 118° C. (onset temperature). In some embodiments, Compound I Oxalate Form B is characterized by the DSC curve as substantially shown in FIG. 46.

In some embodiments, Compound I Oxalate Form B is characterized by a thermogravimetric analysis (TGA) thermogram showing a weight loss of about 0.2% up to 128° C. In some embodiments, Compound I Oxalate Form B is characterized by the thermogram as substantially shown in FIG. 47.

Compound I Sulfate Form A

The present disclosure provides, in some embodiments, a crystalline form (S)-2-hydroxy-6-((4-(2-(2-hydroxyethyl)nicotinoyl)morpholin-3-yl)methoxy)benzaldehyde sulfate ("Compound I Sulfate Form A" or "Sulfate Form A") characterized by an X-ray powder diffractogram comprising the following peaks: 10.7, 18.2, and 23.5 °2θ±0.2 °2θ, as determined on a diffractometer using Cu-Kα radiation. In some embodiments, the diffractogram of Compound I Sulfate Form A further comprises one or more peaks at: 11.6, 19.3, and 20.8 °2θ±0.2 °2θ. In some embodiments, Compound I Sulfate Form A is characterized by the X-ray powder diffractogram as substantially shown in FIG. 48.

In some embodiments, Compound I Sulfate Form A is characterized by a differential scanning calorimetry (DSC) curve that comprises an endotherm at about 146° C. (onset temperature). In some embodiments, Compound I Sulfate Form A is characterized by the DSC curve as substantially shown in FIG. 49.

In some embodiments, Compound I Sulfate Form A is characterized by a thermogravimetric analysis (TGA) thermogram showing a weight loss of about 1.4% up to 161° C. In some embodiments, Compound I Sulfate Form A is characterized by the thermogram as substantially shown in FIG. 50.

Compound I Tosylate Form A

The present disclosure provides, in some embodiments, a crystalline form (S)-2-hydroxy-6-((4-(2-(2-hydroxyethyl)nicotinoyl)morpholin-3-yl)methoxy)benzaldehyde tosylate ("Compound I Tosylate Form A" or "Tosylate Form A") characterized by an X-ray powder diffractogram comprising the following peaks: 4.68, 17.7, and 23.4 °2θ±0.2 °2θ, as determined on a diffractometer using Cu-Kα radiation. In some embodiments, the diffractogram of Compound I Tosylate Form A further comprises one or more peaks at: 18.6 and 19.1 °2θ±0.2 °2θ. In some embodiments, Compound I Tosylate Form A is characterized by the X-ray powder diffractogram as substantially shown in FIG. 51.

In some embodiments, Compound I Tosylate Form A is characterized by a differential scanning calorimetry (DSC) curve that comprises an endotherm at about 115° C. (peak temperature). In some embodiments, Compound I Tosylate Form A is characterized by the DSC curve as substantially shown in FIG. 52.

Figure 53:
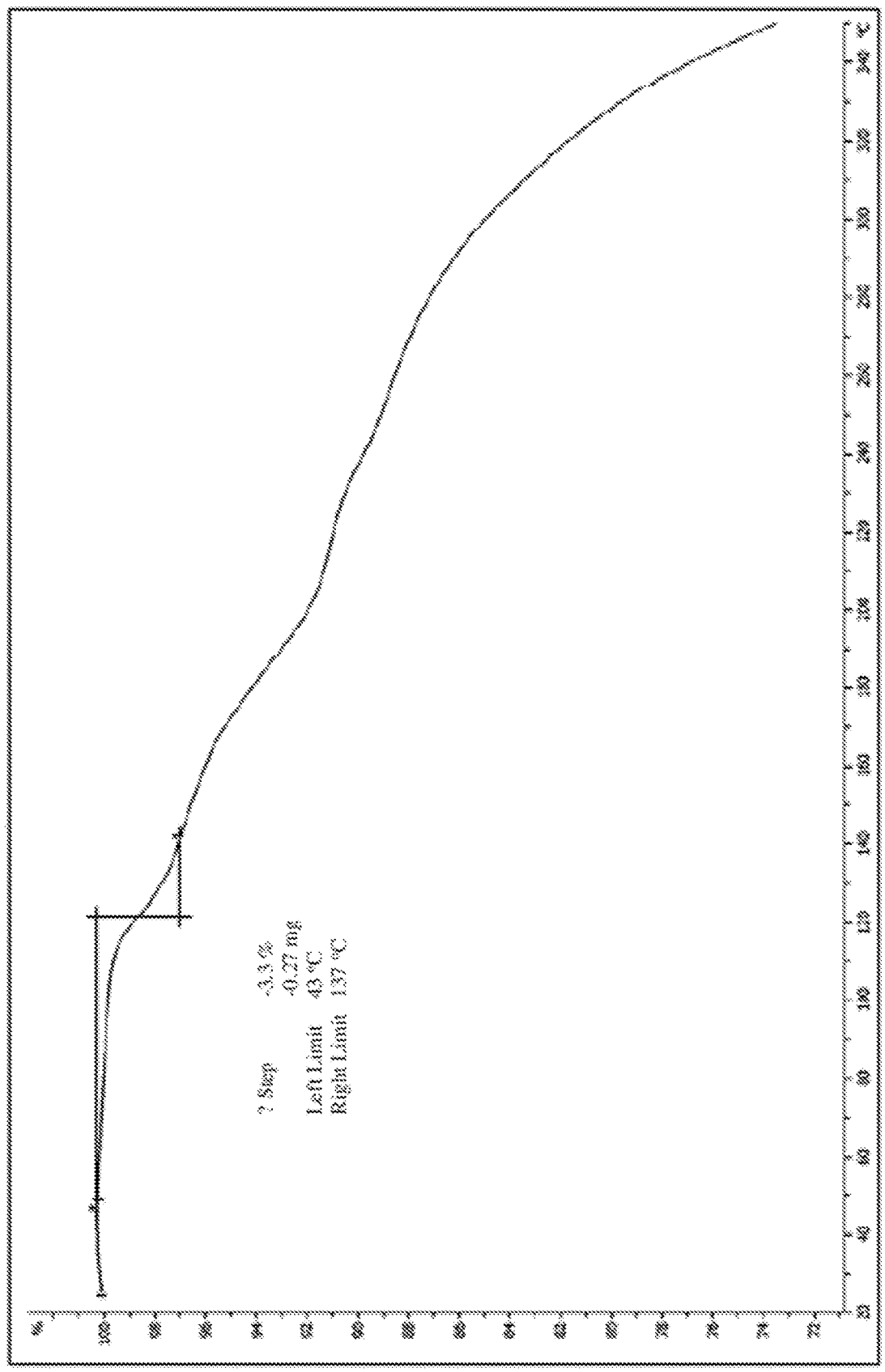
FIG. 53 shows a thermogravimetric analysis (TGA) of Compound I Tosylate Form A.

In some embodiments, Compound I Tosylate Form A is characterized by a thermogravimetric analysis (TGA) thermogram showing a weight loss of about 3.3% up to 137° C. In some embodiments, Compound I Tosylate Form A is characterized by the thermogram as substantially shown in FIG. 53.

3. Pharmaceutical Compositions and Modes of Administration

The forms of Compound I as described herein may be administered in a pharmaceutical composition. Thus, provided herein are pharmaceutical compositions comprising one or more of the forms of Compound I described herein, or salts or solvates thereof, and one or more pharmaceutically acceptable vehicles such as carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions (or crystalline forms or crystalline salt forms described herein) may be administered alone or in combination with other therapeutic agents. In some embodiments, the other therapeutic agent is a modulator of hemoglobin. In some embodiments, the other therapeutic agent is useful for treating sickle cell disease. In some embodiments, the other therapeutic agent is useful for treating a complication of sickle cell disease. Non-limiting examples of a complication of sickle cell disease include iron overload, pain, infections, acute chest syndrome, stroke, and pulmonary hypertension. In some embodiments, the other therapeutic agent is hydroxyurea, L-glutamine, crizanlizumab, or deferiprone.

Some embodiments provide for a pharmaceutical composition comprising a crystalline form as described herein or a crystalline salt form as described herein and a pharmaceutically acceptable excipient. Some embodiments provide for a pharmaceutical composition comprising a therapeutically effective amount of a crystalline form as described herein or a crystalline salt form as described herein and a pharmaceutically acceptable excipient.

In some embodiments, a pharmaceutical composition comprises a crystalline form selected from: Compound I Form I, Compound I Material II, Compound I HCl Form A, Compound I Besylate Form A, Compound I Edisylate Form A, Compound I Edisylate Material B, Compound I Esylate Form A, Compound I Esylate Form B, Compound I Napadisylate Form A, Compound I Napadisylate Material B, Compound I Napsylate Form A, Compound I Napsylate Material B, Compound I Oxalate Material A, Compound I Oxalate Form B, Compound I Sulfate Form A, and Compound I Tosylate Form A; and one or more pharmaceutically acceptable carriers.

Some embodiments provide for a pharmaceutical composition comprising a pharmaceutically acceptable excipient, a crystalline form as described herein or a crystalline salt form as described herein, and another therapeutic agent.

In some embodiments, a pharmaceutical composition comprises Compound I, wherein at least 95% of Compound I is in a crystalline form as described herein. In some embodiments, a pharmaceutical composition comprises Compound I, wherein at least 95% of Compound I is in Form I. In some embodiments, a pharmaceutical composition comprises Compound I, wherein at least 95% of Compound I is Compound I HCl Form A, Compound I Oxalate Form B, or Compound I Sulfate Form A.

In some embodiments, a pharmaceutical composition comprises Compound I, wherein at least 97% of Compound I is in a crystalline form as described herein. In some embodiments, a pharmaceutical composition comprises Compound I, wherein at least 97% of Compound I is in Form I. In some embodiments, a pharmaceutical composition comprises Compound I, wherein at least 97% of Compound I is in Material II. In some embodiments, a pharmaceutical composition comprises Compound I, wherein at least 97% of Compound I is Compound I HCl Form A, Compound I Oxalate Form B, or Compound I Sulfate Form A.

In some embodiments, a pharmaceutical composition comprises Compound I, wherein at least 99% of Compound I is in a crystalline form as described herein. In some embodiments, a pharmaceutical composition comprises Compound I, wherein at least 99% of Compound I is in Form I. In some embodiments, a pharmaceutical composition comprises Compound I, wherein at least 99% of Compound I is in Material II. In some embodiments, a pharmaceutical composition comprises Compound I, wherein at least 99% of Compound I is in HCl Form A. In some embodiments, a pharmaceutical composition comprises Compound I, wherein at least 99% of Compound I is Compound I HCl Form A, Compound I Oxalate Form B, or Compound I Sulfate Form A.

In some embodiments, a pharmaceutical composition comprises Compound I, wherein at least 99.5% of Compound I is in a crystalline form as described herein. In some embodiments, a pharmaceutical composition comprises Compound I, wherein at least 99.5% of Compound I is in Form I. In some embodiments, a pharmaceutical composition comprises Compound I, wherein at least 99.5% of Compound I is Compound I HCl Form A, Compound I Oxalate Form B, or Compound I Sulfate Form A.

In some embodiments, a pharmaceutical composition comprises Compound I, wherein at least 99.9% of Compound I is in a crystalline form as described herein. In some embodiments, a pharmaceutical composition comprises Compound I, wherein at least 99.9% of Compound I is in Form I. In some embodiments, a pharmaceutical composition comprises Compound I, wherein at least 99.9% of Compound I is Compound I HCl Form A, Compound I Oxalate Form B, or Compound I Sulfate Form A.

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the solid forms described herein, or salts or solvates thereof. Administration may be via, for example, capsule or enteric coated tablets. In making the pharmaceutical compositions that include at least one solid form described herein, or salts or solvates thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active ingredient, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one solid form described herein, or salts or solvates thereof, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the solid forms described herein, or salts or solvates thereof, in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on-demand delivery of pharmaceutical agents.

For preparing solid compositions such as tablets, the principal active ingredient may be mixed with a pharmaceutical excipient to form a solid preformulation composition containing a homogeneous mixture of a solid form described herein, or salts or solvates thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the solid forms described herein, or salts or solvates thereof, may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

4. Dosing

The specific dose level of a solid form, or a salt or a solvate thereof, of the present application for any particular subject will depend upon a variety of factors, including the activity of the specific solid form employed, the age, body weight, general health, sex, diet, time of administration, route of administration, and rate of excretion, drug combination and the severity of the particular disease in the subject undergoing therapy. For example, a dosage may be expressed as a number of milligrams of a solid form described herein, or a salt or a solvate thereof, per kilogram of the subject's body weight (mg/kg). Dosages of between about 0.1 and 150 mg/kg may be appropriate. In some embodiments, about 0.1 and 100 mg/kg may be appropriate. In other embodiments, a dosage of between 0.5 and 60 mg/kg may be appropriate. Normalizing according to the subject's body weight is particularly useful when adjusting dosages between subjects of widely disparate size, such as occurs when using the solid forms in both children and adult humans or when converting an effective dosage in a non-human subject such as dog to a dosage suitable for a human subject.

5. Methods

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition; and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. A solid forms described herein, or a salt or a solvate thereof, may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In some embodiments, the subject is a human.

The term "therapeutically effective amount" or "effective amount" of a solid form described herein, or a salt or a solvate thereof, means an amount sufficient to effect treatment when administered to a subject, to provide a therapeutic benefit such as amelioration of symptoms or slowing of disease progression. For example, a therapeutically effective amount may be an amount sufficient to decrease a symptom of a sickle cell disease. The therapeutically effective amount may vary depending on the subject, and disease or condition being treated, the weight and age of the subject, the severity of the disease or condition, and the manner of administering, which can readily be determined by one of ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the forms described herein and compositions described herein may be used for a variety of purposes, including therapeutic and experimental purposes. For example, the forms described herein and compositions described herein may be used ex vivo to determine the optimal schedule and/or dosing of administration of a form of the present disclosure for a given indication, cell type, individual, and other parameters. Information gleaned from such use may be used for experimental purposes or in the clinic to set protocols for in vivo treatment. Other ex vivo uses for which the forms described herein and compositions described herein may be suited are described below or will become apparent to those skilled in the art. The selected forms described herein may be further characterized to examine the safety or tolerance dosage in human or non-human subjects. Such properties may be examined using commonly known methods to those skilled in the art.

The term "hemoglobin" as used herein refers to any hemoglobin protein, including normal hemoglobin (HbA) and abnormal hemoglobin, such as sickle hemoglobin (HbS).

The term "sickle cell disease" refers to diseases mediated by sickle hemoglobin (HbS) that results from a single point mutation in the hemoglobin (Hb). Sickle cell diseases include sickle cell anemia (HbSS), hemoglobin SC disease (HbSC), hemoglobin S beta-plus-thalassemia (HbS/β+) and hemoglobin S beta-zero-thalassemia (HbS/β0).

Provided herein are methods for treating sickle cell disease (SCD). Sickle hemoglobin (HbS) contains a point mutation where glutamic acid is replaced with valine, making HbS susceptible to polymerization under hypoxic conditions to give the HbS containing red blood cells their characteristic sickle shape. The sickled cells are also more rigid than normal red blood cells, and their lack of flexibility can lead to blockage of blood vessels. It is contemplated that an approach to therapy would be to maintain the HbS in the oxygenated state, as polymerization occurs only in the deoxygenated state under hypoxic conditions.

In some embodiments, provided herein is a method for increasing oxygen affinity of hemoglobin S in a subject in need thereof, comprising administering to the subject a solid form described herein, or a salt or a solvate thereof, or a pharmaceutical composition as described herein.

In some embodiments, provided herein is a method for increasing oxygen affinity of hemoglobin S in a subject in need thereof, comprising administering to the subject a crystalline form or crystalline salt form as described herein or a pharmaceutical composition as described herein.

In some embodiments, provided herein is a method for treating a disorder mediated by hemoglobin in a subject in need thereof, comprising administering to the subject a solid form described herein, or a salt or a solvate thereof, or a pharmaceutical composition as described herein.

In some embodiments, provided herein is a method for treating a disorder mediated by hemoglobin in a subject in need thereof, comprising administering to the subject a crystalline form or crystalline salt form as described herein or a pharmaceutical composition as described herein.

In some embodiments, the disorder is a hemoglobinopathy. In some embodiments, the hemoglobin is sickle hemoglobin.

In some embodiments, provided herein is a method for treating sickle cell disease in a subject in need thereof, comprising administering to the subject a solid form described herein, or a salt or a solvate thereof, or a pharmaceutical composition as described herein.

In some embodiments, provided herein is a method for treating sickle cell disease in a subject in need thereof, comprising administering to the subject a crystalline form or crystalline salt form as described herein, or a pharmaceutical composition as described herein.

EXAMPLES

Instrumental Techniques

X-Ray Powder Diffraction (XRPD)

XRPD figures were generated using SSCI Pattern Match 3.0.4, unvalidated software.

XRPD patterns were collected with a PANalytical X'Pert PRO MPD or a PANalytical Empyrean diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e or NIST SRM 640f) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening and asymmetry from axial divergence. Diffraction patterns were collected using a scanning position-sensitive detector (X'Celerator) located 240 mm from the specimen and Data Collector software v. 2.2b or v. 5.5.

Reflection Geometry

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e or NIST SRM 640f) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 5.5.

Differential Scanning Calorimetry (DSC)

DSC was performed using a Mettler-Toledo DSC3+ differential scanning calorimeter. A tau lag adjustment was performed with indium, tin, and zinc. The temperature and enthalpy were adjusted with octane, phenyl salicylate, indium, tin and zinc. The adjustment was then verified with octane, phenyl salicylate, indium, tin, and zinc. The sample was placed into a hermetically sealed aluminum DSC pan, and the weight was accurately recorded. The pan was then inserted into the DSC cell. A weighed aluminum pan configured as the sample pan was placed on the reference side of the cell. The pan lid was pierced prior to sample analysis. Samples were analyzed from −30° C. to 250° C. @ 10°/min.

The cyclic DSC method heated from −30° C. to 100° C., returned to −30° C., then heated to 250° C. at 10°/min.

Dynamic Vapor Sorption/Desorption (DVS)

Automated vapor sorption (VS) data were collected on a Surface Measurement System DVS Intrinsic instrument or a VTI SGA-100 instrument. Samples were not dried prior to analysis. Sorption and desorption data were collected over a range from 5% to 95% relative humidity (RH) at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Thermogravimetric Analysis (TGA)

TG analysis was performed using a Mettler-Toledo TGA/DSC3+ analyzer. Temperature and enthalpy adjustments were performed using indium, tin, and zinc, and then verified with indium. The balance was verified with calcium oxalate. The sample was placed in an open aluminum pan. The pan was hermetically sealed, the lid pierced, then inserted into the TG furnace. A weighed aluminum pan configured as the sample pan was placed on the reference platform. The furnace was heated under nitrogen. Each sample was heated from ambient temperature to 350° C. at 10° C./min.

Ion Chromatography

Ion chromatography was performed to quantify the weight percent of a selected anion in each sample. The samples were prepared by dissolving approximately 5-10 mg of sample water.

Solution-State Proton Nuclear Magnetic Resonance ($^1$H NMR)

The solution NMR spectra were acquired with an Avance 600 MHz NMR spectrometer. The samples were prepared by dissolving given amount of sample in DMSO-$d_6$ containing TMS.

Single Crystal Data Collection Compound I Form I

Standard uncertainty is written in crystallographic parenthesis notation, e.g. 0.123(4) is equivalent to 0.123±0.004. Calculated XRPD patterns were generated for Cu radiation using Mercury and the atomic coordinates, space group, and unit cell parameters from the single crystal structure. The atomic displacement ellipsoid diagrams were prepared using Mercury. Atoms are represented by 50% probability anisotropic thermal ellipsoids. The quality of the structure obtained is high, as indicated by the fit residual, R, of 0.0317 (3.17%). R-factors in the range 2%-6% are quoted to be the most reliably determined structures.

Data Collection: A colorless plate having approximate dimensions of 0.18×0.08×0.03 mm$^3$, was mounted on a polymer loop in random orientation. Preliminary examination and data collection were performed on a Rigaku Super-Nova diffractometer, equipped with a copper anode microfocus sealed X-ray tube (Cu K$\alpha\lambda$=1.54184 Å) and a Dectris Pilatus3 R 200K hybrid pixel array detector. Cell constants and an orientation matrix for data collection were obtained from least-squares refinement using the setting angles of 4579 reflections in the range 4.3100°<θ<77.1380°. The space group was determined by the program CRYSALIS-PRO to be $P2_12_12_1$ (international tables no. 19). The data were collected to a maximum diffraction angle (2θ) of 155.236° at room temperature.

Data Reduction: Frames were integrated with CrysAlis-Pro. A total of 8747 reflections were collected, of which 3808 were unique. Lorentz and polarization corrections were applied to the data. The linear absorption coefficient is 0.860 mm$^{-1}$ for Cu K$\alpha$ radiation. An empirical absorption correction using CrysAlisPro was applied. Transmission coefficients ranged from 0.957 to 1.000. A secondary extinction correction was applied. The final coefficient, refined in least-squares, was 0.0023(3) (in absolute units). Intensities of equivalent reflections were averaged. The agreement factor for the averaging was 2.55% based on intensity.

Single Crystal Data Collection Compound I HCl Form A

Standard uncertainty is written in crystallographic parenthesis notation, e.g. 0.123(4) is equivalent to 0.123±0.004. Calculated XRPD patterns were generated for Cu radiation using Mercury and the atomic coordinates, space group, and unit cell parameters from the single crystal structure. The atomic displacement ellipsoid diagrams were prepared using Mercury. Atoms are represented by 50% probability anisotropic thermal ellipsoids. The quality of the structure obtained is high, as indicated by the fit residual, R, of 0.0389 (3.89%). R-factors in the range 2%-6% are quoted to be the most reliably determined structures.

Data Collection: A colorless plate having approximate dimensions of 0.36×0.16×0.03 mm$^3$, was mounted on a polymer loop in random orientation. Preliminary examination and data collection were performed on a Rigaku Super-Nova diffractometer, equipped with a copper anode microfocus sealed X-ray tube (Cu K$\alpha\lambda$=1.54184 Å) and a Dectris Pilatus3 R 200K hybrid pixel array detector. Cell constants and an orientation matrix for data collection were obtained from least-squares refinement using the setting angles of 7034 reflections in the range 5.0710°<θ<77.0390°. The space group was determined by the program CRYSALIS-PRO to be $P2_1$ (international tables no. 4). The data were collected to a maximum diffraction angle (2θ) of 154.678° at room temperature.

Data Reduction: Frames were integrated with CrysAlis-Pro. A total of 10895 reflections were collected, of which 4117 were unique. Lorentz and polarization corrections were applied to the data. The linear absorption coefficient is 2.004 mm$^{-1}$ for Cu K$\alpha$ radiation. An empirical absorption correction using CrysAlisPro was applied. Transmission coefficients ranged from 0.716 to 1.000. Intensities of equivalent reflections were averaged. The agreement factor for the averaging was 2.67% based on intensity.

Example 1: Characterization of Amorphous Compound I

Compound I may be made according to methods known in the art.

Figure 13:
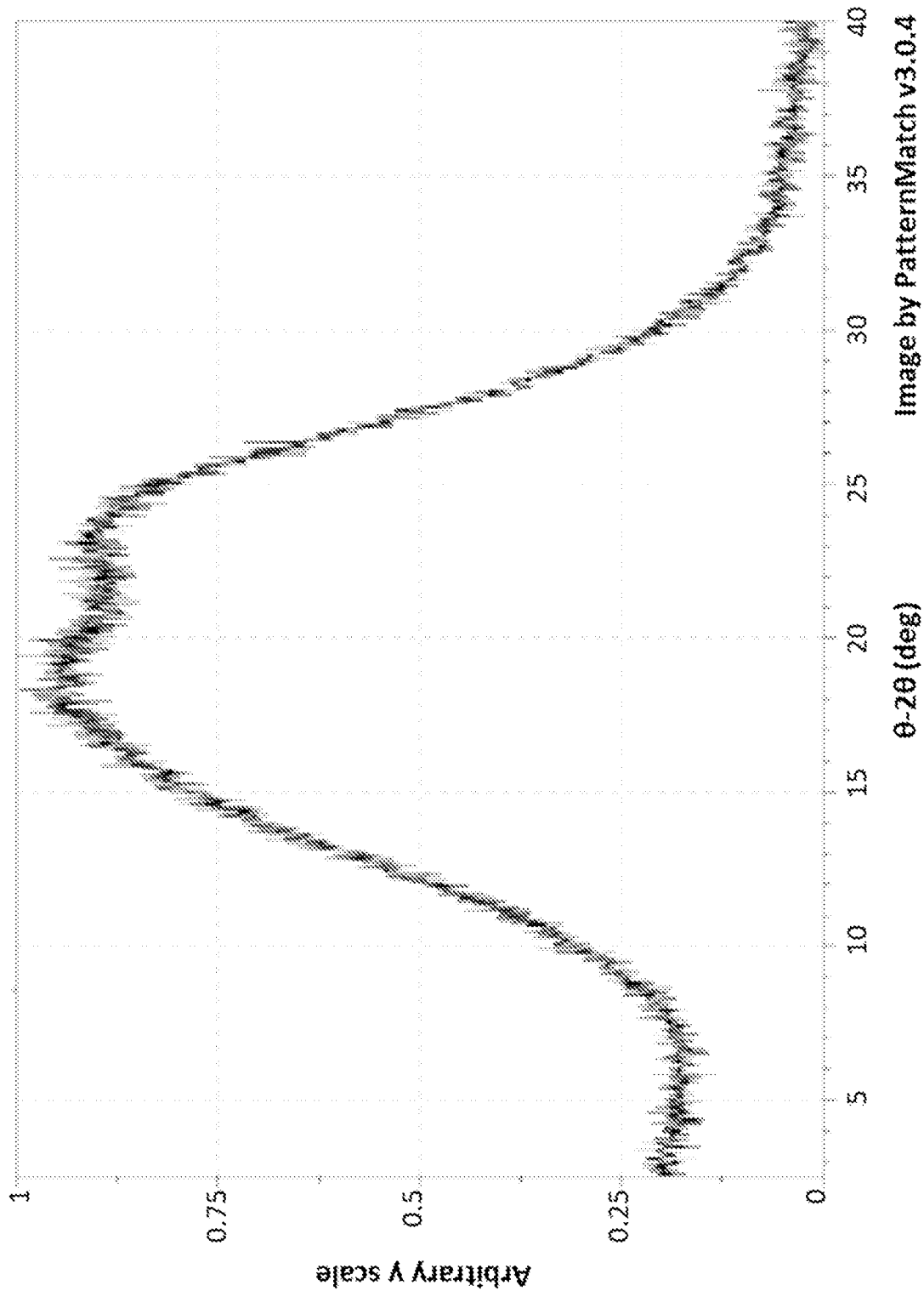
FIG. 13 shows an X-ray powder diffraction (XRPD) of amorphous Compound I.
Figure 14:
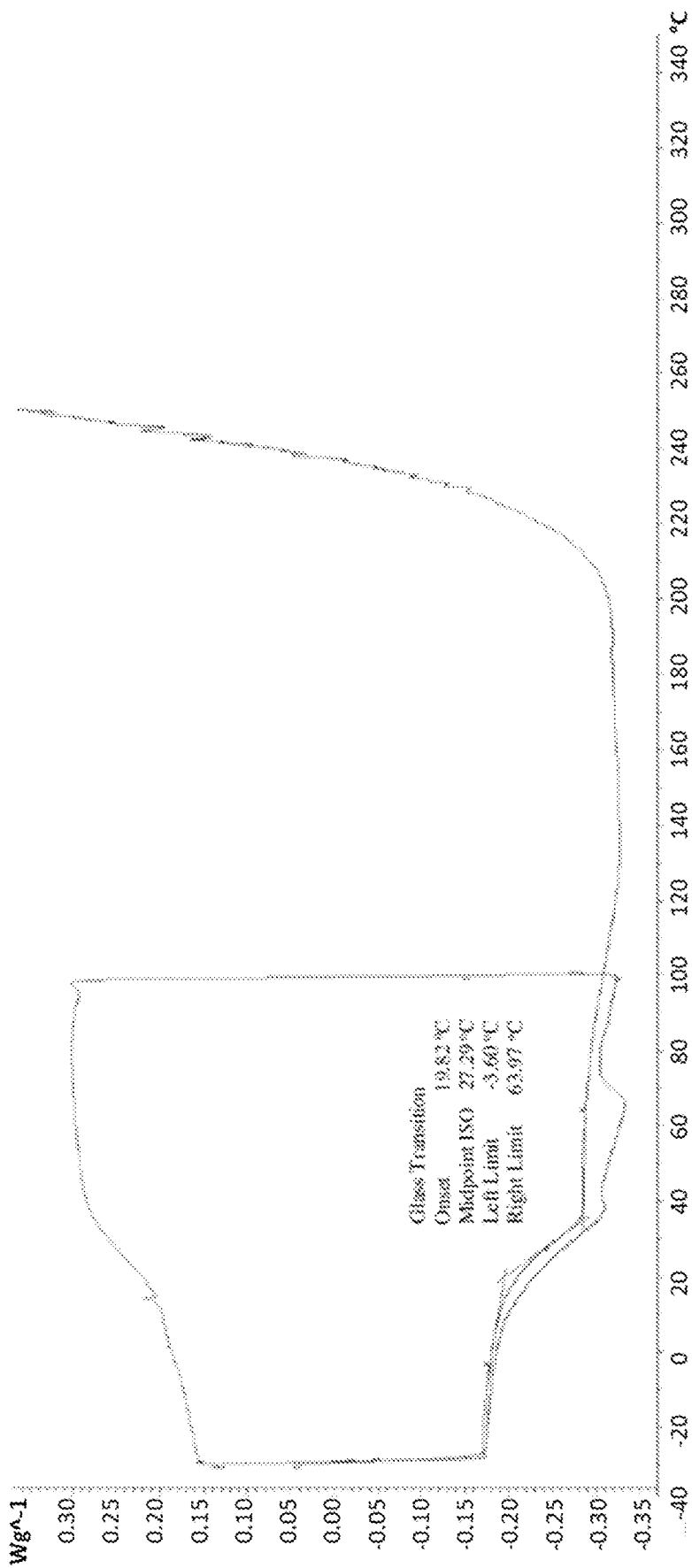
FIG. 14 shows a differential scanning calorimeter (DSC) curve of amorphous Compound I.
Figure 15:
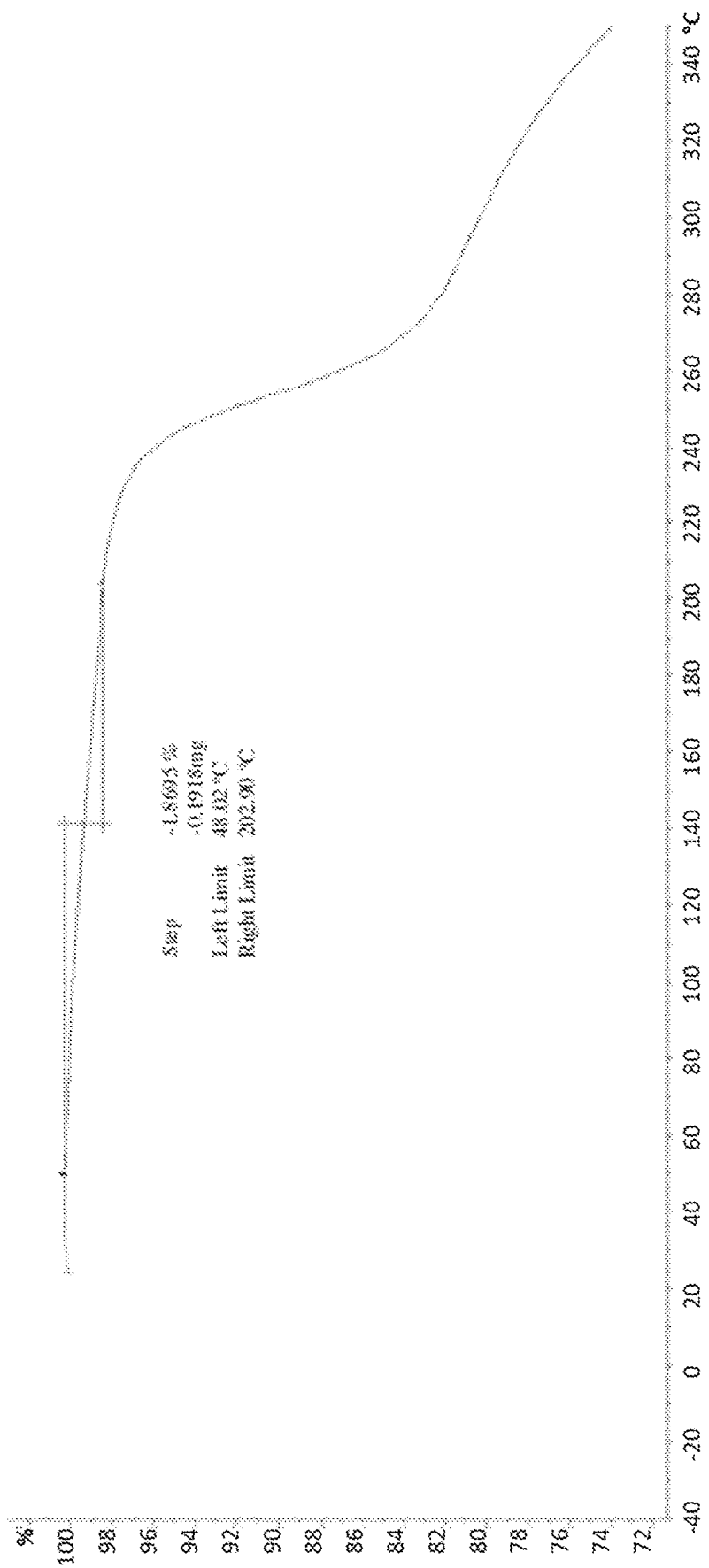
FIG. 15 shows a thermogravimetric analysis (TGA) of amorphous Compound I.

FIG. 13 depicts an X-ray powder diffraction (XRPD) pattern for amorphous Compound I. A continuous weight loss of approximately 1.9% up to 203° C. is observed by TGA (FIG. 15). A cycling DSC experiment was performed to measure the glass transition ($T_g$) after the removal of residual moisture upon heating. Amorphous Compound I exhibits a $T_g$ at approximately 27° C. (midpoint). The observation of a $T_g$ can be characteristic of the non-crystalline nature of the material. Decomposition, rather than recrystallization, was observed above the glass transition temperature.

Figure 16:
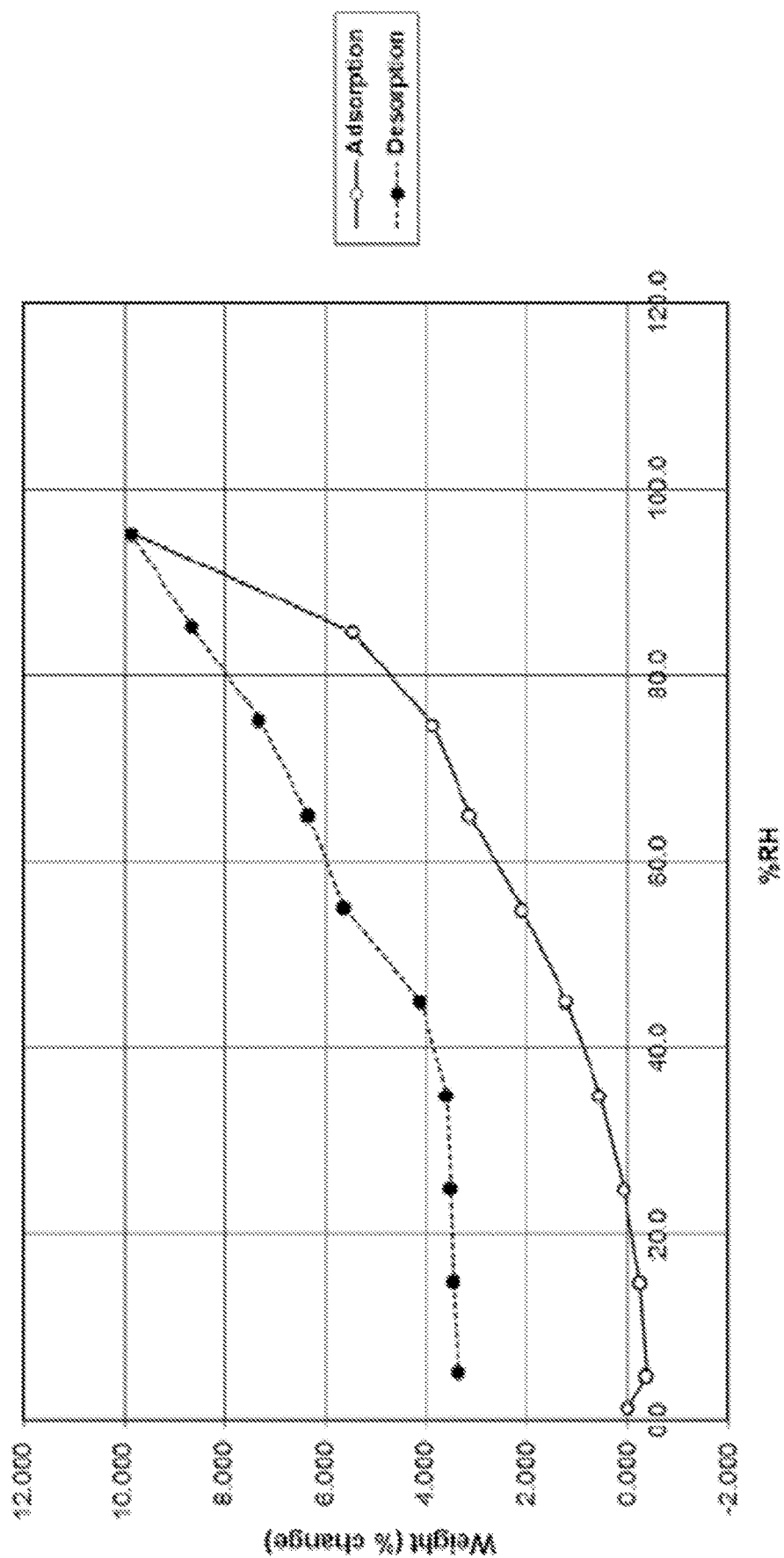
FIG. 16 shows dynamic vapor sorption (DVS plot) of amorphous Compound I.

The dynamic vapor sorption (DVS) isotherm indicates the material exhibits significant hygroscopicity from 5 to 95% RH (FIG. 16). The weight gain through the sorption cycle was approximately 10%. Hysteresis was observed with a 7% weight loss upon desorption. The material recovered from the DVS experiment remained amorphous, as determined by XRPD.

Example 2: Preparation of Compound I Form I

A solution of amorphous Compound I in MeCN (>540 mg/mL) was refrigerated for 4 days and then placed in a freezer for 1 day. The solids were filtered and dried under nitrogen to provide Compound I Form I.

Compound I Form I was also prepared as follows: Amorphous Compound I was slurried in ether with seeding with Compound I Form I from another experiment (prepared as described herein) at ambient temperature for 1 day, providing Compound I Form I.

Figure 2A:
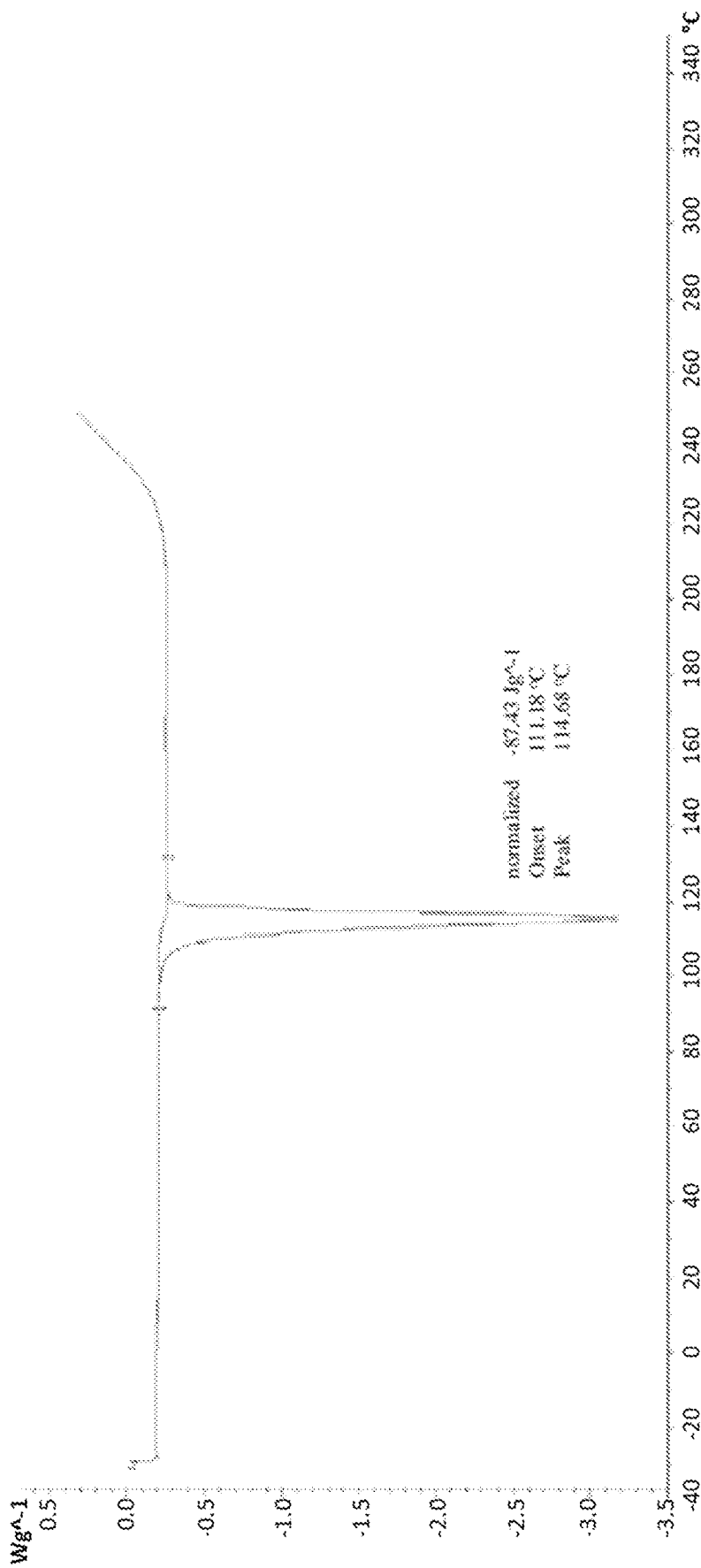
FIG. 2A shows a differential scanning calorimeter (DSC) curve of Compound I Form I.

Compound I Form I is anhydrous with a melt onset near 111° C. (FIG. 2A).

The single-crystal structure of Compound I Form I was determined successfully. The crystal system is orthorhombic and the space group is $P2_12_12_1$. The cell parameters and calculated volume are: a=5.50599(10) Å, b=16.4086(2) Å, c=20.4992(4) Å, α=90°, β=90°, γ=90°, V=1852.02(5) Å$^3$. The formula weight is 386.39 g mol$^{-1}$ with Z=4, resulting in a calculated density of 1.386 g cm$^{-3}$. Further details of the crystal data and crystallographic data collection parameters are summarized in Table 1.

TABLE 1

Crystal Data and Data Collection Parameters for Compound I Form I.

| | |
|---|---|
| Empirical formula | $C_{20}H_{22}N_2O_6$ |
| Formula weight (g mol$^{-1}$) | 386.39 |
| Temperature (K) | 299.52(12) |
| Wavelength (Å) | 1.54184 |
| Crystal system | orthorhombic |
| Space group | $P2_12_12_1$ |
| Unit cell parameters | |
| a = 5.50599(10) Å | α = 90° |
| b = 16.4086(2) Å | β = 90° |
| c = 20.4992(4) Å | γ = 90° |
| Unit cell volume (Å$^3$) | 1852.02(5) |
| Cell formula units, Z | 4 |
| Calculated density (g cm$^{-3}$) | 1.386 |
| Absorption coefficient (mm$^{-1}$) | 0.860 |
| F(000) | 816 |
| Crystal size (mm$^3$) | 0.18 × 0.08 × 0.03 |
| Reflections used for cell measurement | 4579 |
| θ range for cell measurement | 4.3100°-77.1380° |
| Total reflections collected | 8747 |
| Index ranges | −6 ≤ h ≤ 6; −20 ≤ k ≤ 20; −23≤ l ≤25 |
| θ range for data collection | $θ_{min}$ = 3.450°, $θ_{max}$ = 77.618° |
| Completeness to $θ_{max}$ | 98.6% |
| Completeness to $θ_{full}$ = 67.684° | 100% |
| Absorption correction | multi-scan |
| Transmission coefficient range | 0.957-1.000 |
| Refinement method | full matrix least-squares on F$^2$ |
| Independent reflections | 3808 [$R_{int}$ = 0.0255, $R_σ$ = 0.0321] |
| Reflections [ I > 2σ(I) ] | 3458 |
| Reflections/restraints/parameters | 3808/0/342 |
| Goodness-of-fit on F$^2$ | S = 1.05 |
| Final residuals [ I > 2σ(I) ] | R = 0.0317, $R_w$ = 0.0762 |
| Final residuals [ all reflections ] | R = 0.0357, $R_w$ = 0.0784 |
| Largest diff. peak and hole (e Å$^{-3}$) | 0.118, −0.120 |
| Max/mean shift/standard uncertainty | 0.000/0.000 |
| Absolute structure determination | Flack parameter: −0.21(12) |

The TGA curve (FIG. 3) exhibits negligible weight loss upon heating up to 192° C., consistent with an anhydrous form.

DSC thermograms were obtained on two different samples of Compound I Form I. Sample B was crystallized from amorphous Compound I by slurrying with seed (which was obtained from amorphous Compound I by slurrying in ether at ambient temperature for 4 day) in ether at ambient temperature for 1 day.

Figure 2B:
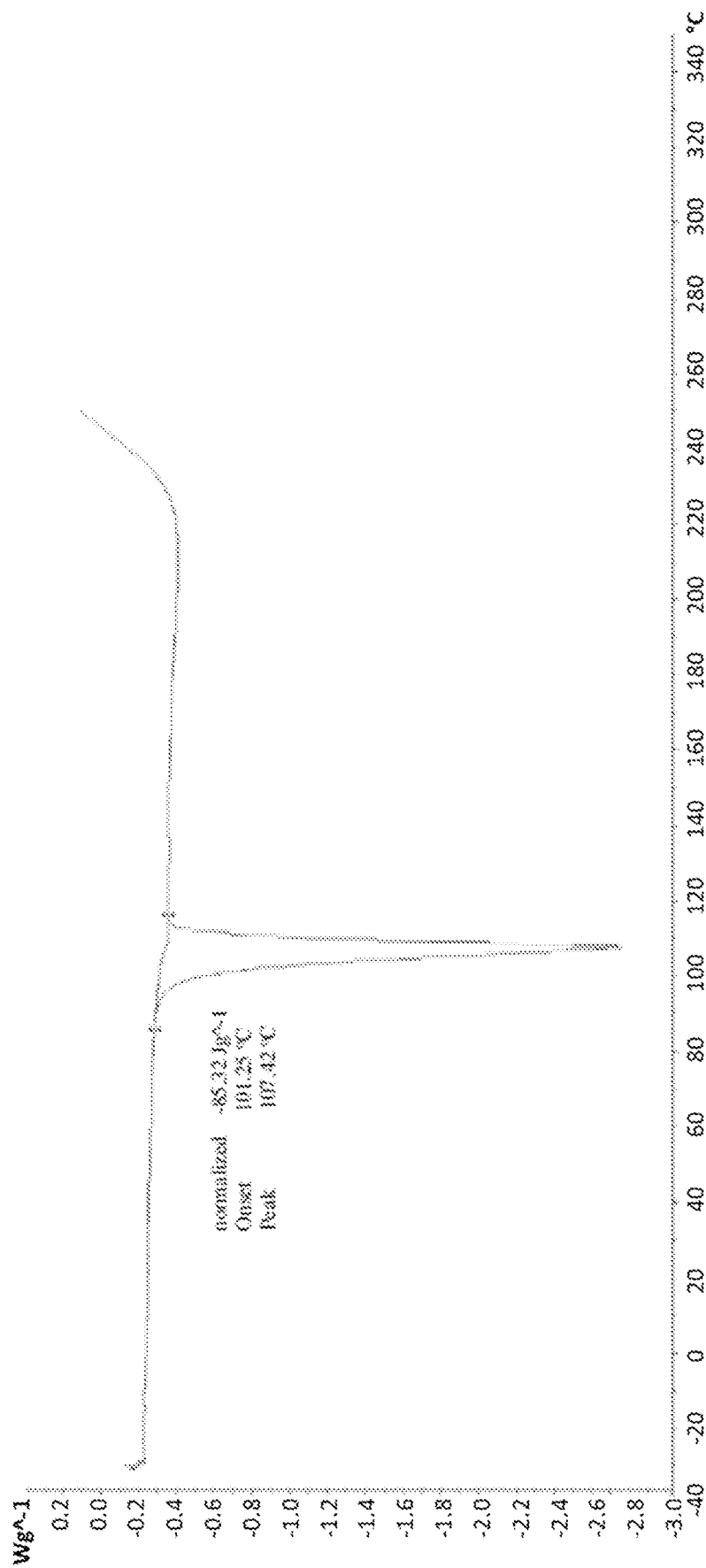
FIG. 2B shows another differential scanning calorimeter (DSC) curve of Compound I Form I.

Sample A was obtained by slurrying Compound I Form I in MeCN at ambient temperature for 6 days. Sample B, shown in FIG. 2B, exhibits a melt onset of 101° C. Conversely, Sample A was obtained from sequential recrystallizations and was white in color, suggesting the sample is more representative of pure material. Sample A, shown in FIG. 2A, exhibits a higher melt onset of 111° C. (87 J/g).

Figure 4:
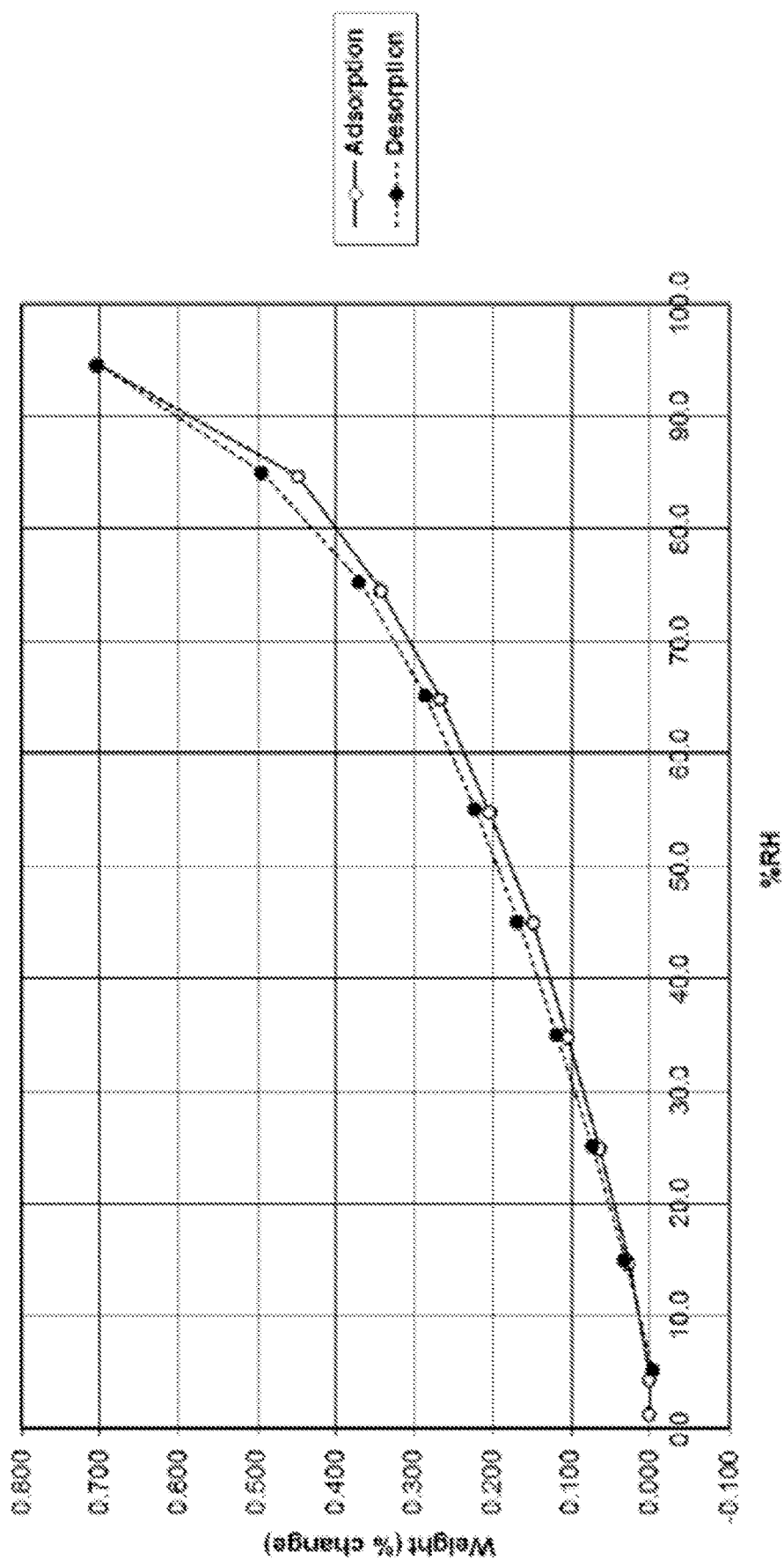
FIG. 4 shows dynamic vapor sorption (DVS plot) of Compound I Form I.

The DVS isotherm indicates that Form I exhibits low hygroscopicity (FIG. 4). A total of 0.7% weight gain and loss was observed during the adsorption/desorption cycle with no hysteresis. The material recovered from the DVS experiment was identified as Compound I Form I by XRPD.

Example 3: Preparation of Compound I Material II

Compound I Form I was dissolved in DCM, and the solution was added to heptane. The resulting suspension was stirred at ambient temperature for 3 days then in refrigerated conditions for 8 days, providing Compound I Material II.

Compound I was also dissolved in EtOAc and concentrated to an oil. To the residue was added seed of Compound I Material II, prepared as described above, and MTBE was added. The turbid mixture was stirred at ambient temperature for 7 days. The slurry was concentrated by fast evaporation. The residue was treated with MTBE, providing Compound I Material II.

Figure 6:
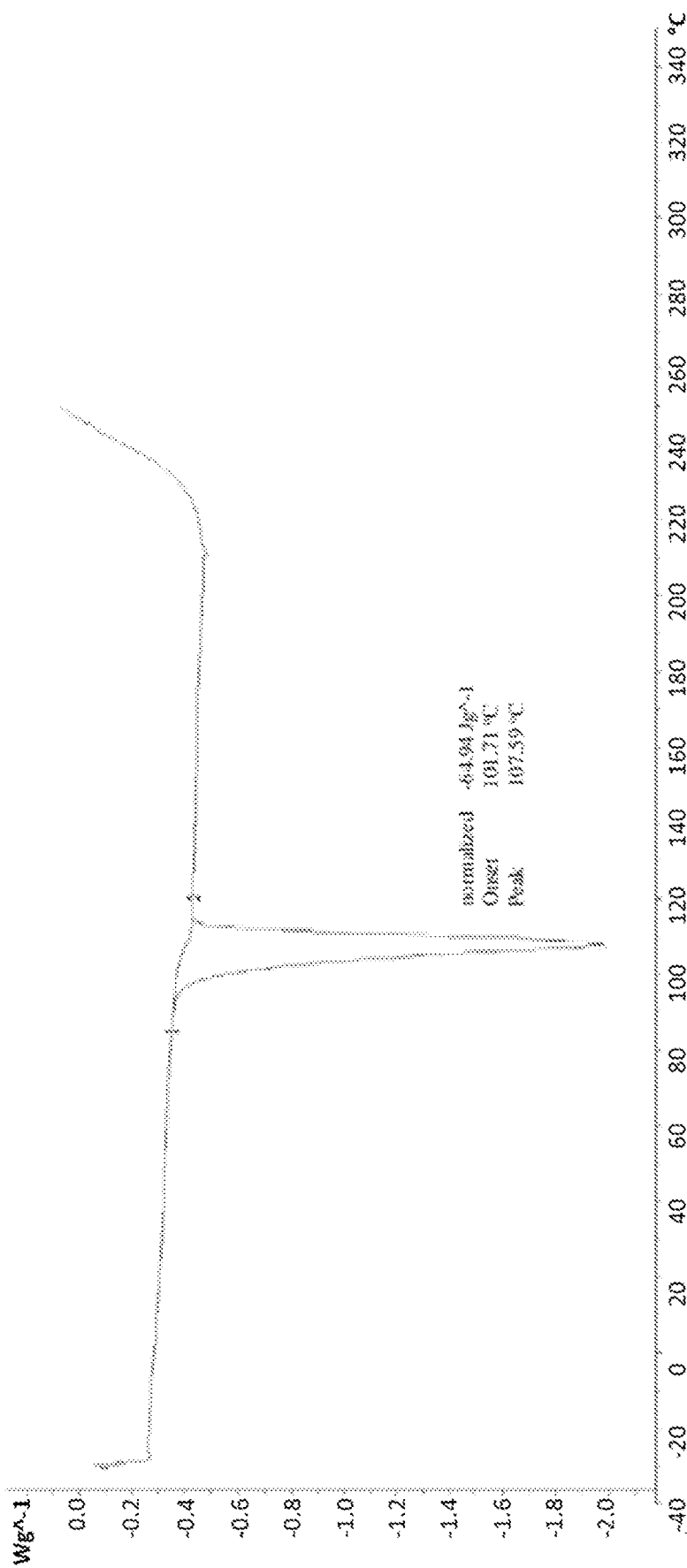
FIG. 6 shows a differential scanning calorimeter (DSC) curve of Compound I Material II.

Compound I Material II is anhydrous with a melt onset near 102° C. (FIG. 6).

A representative XRPD pattern for Compound I Material II is shown in FIG. 5. Data suggests that Material II is a unique crystalline phase; however, although attempted, XRPD patterns of Material II could not be indexed to confirm phase purity.

The TGA curve (FIG. 7) exhibits negligible weight loss upon heating up to 195° C., consistent with an anhydrous form.

The DSC curve (FIG. 6) exhibits a single endotherm with an onset near 102° C. (65 J/g).

Figure 8:
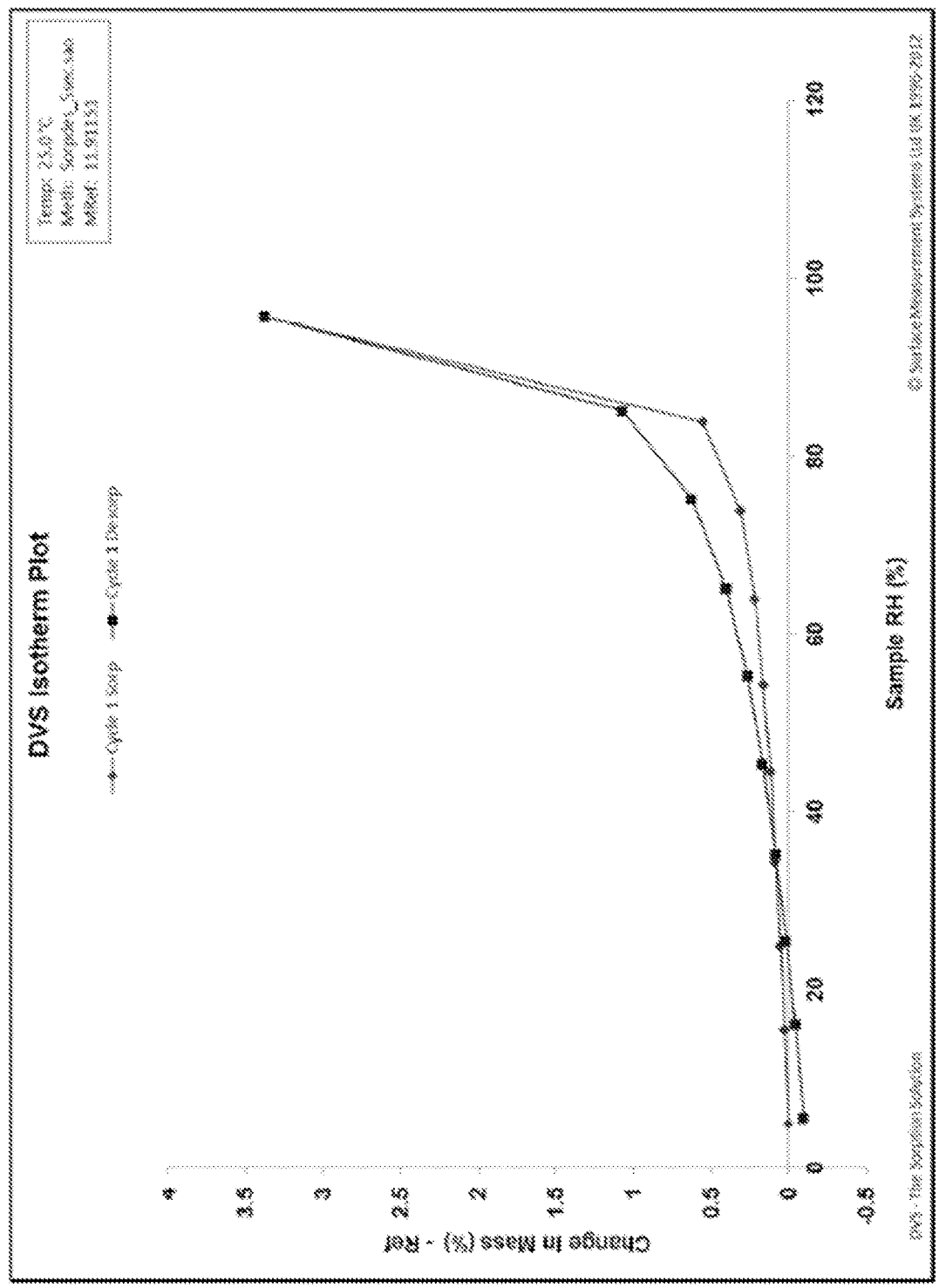
FIG. 8 show dynamic vapor sorption (DVS plot) of Compound I Material II.

The DVS isotherm indicates that Material II exhibits significant hygroscopicity above 85% RH (FIG. 8). The weight gain and loss through the sorption/desorption cycle was approximately 3.4%, with the majority of the weight change occurring above 85% RH. Hysteresis was evident upon desorption. The material recovered from the DVS experiment was identified as Compound I Material II by XRPD.

Material II was observed less frequently than Form I and only from kinetic experiments (solvent/anti-solvent additions).

Example 4: Interconversion Studies

Binary interconversion slurry experiments between Compound I Form I and Compound I Material II in different solvent systems at room temperature are summarized in Table 2. Saturated solutions were generated and then added to mixtures composed of approximately equivalent quantities of the two polymorphs. The samples were slurried for several days and the solids harvested and analyzed by XRPD. An elevated temperature experiment was attempted; however, the solvent provided limited solubility and conversion did not occur within the timespan evaluated. The results of the room temperature interconversion studies confirm that Form I is the most thermodynamically stable form relative to Material II.

TABLE 2

| Temperature | Time | Solvent | Result |
|---|---|---|---|
| ambient | 11 days | EtOAc | A |
| ambient | 11 days | IPA | A |
| ambient | 11 days | water | A |
| 94° C. | 2 days | heptane | A + B |

Example 5: Preparation of Compound I HCl Form A

To a solution of 79.2 mg of amorphous Compound I in 0.5 mL of THF was added a molar equivalent of HCl in THF. The resulting solids were filtered, forming Compound I HCl Form A.

An amber solution was generated with 1.09 g of amorphous Compound I in 3 mL of tetrahydrofuran. The Compound I solution was stirred at 250 RPM (magnetic stir bar) and seeded with Compound I HCl Form A (made according to the paragraph above). An acidic solution was generated with 0.213 mL of 37% HCl in 2 mL of tetrahydrofuran (molar equivalent) and then, in turn, slowly added to the seeded Compound I solution. Precipitation was immediately evident. After approximately 15 minutes the solids were collected by vacuum filtration, rinsed with 2 mL of tetrahydrofuran and vacuum dried overnight to yield 1.10 g of Compound I HCl Form A.

Compound I HCl Form A is anhydrous with a melt onset near 193° C. The single-crystal structure of HCl Form A was determined successfully. The crystal system is monoclinic and the space group is $P2_1$. The cell parameters and calculated volume are: a=7.72088(10) Å, b=7.57161(10) Å, c=17.6273(2) Å, α=90°, β=98.0066(12)°, γ=90°, V=1022.44(2) Å$^3$. The formula weight is 422.85 g mol$^{-1}$ with Z=2, resulting in a calculated density of 1.376 g cm$^{-3}$. Further details of the crystal data and crystallographic data collection parameters are summarized in Table 3.

TABLE 3

Crystal Data and Data Collection Parameters for Compound 1 HCl Form A.

| | |
|---|---|
| Empirical formula | $C_{20}H_{23}ClN_2O_6$ |
| Formula weight (g mol$^{-1}$) | 422.85 |
| Temperature (K) | 299.38(13) |
| Wavelength (Å) | 1.54184 |
| Crystal system | monoclinic |
| Space group | $P2_1$ |
| Unit cell parameters | |
| a = 7.72088(10) Å | α = 90° |
| b = 7.57161(10) Å | β = 98.0066(12)° |
| c = 17.6273(2) Å | γ = 90° |
| Unit cell volume (Å$^{-3}$) | 1020.44(2) |
| Cell formula units, Z | 2 |
| Calculated density (g cm$^{-3}$) | 1.376 |
| Absorption coefficient (mm$^{-1}$) | 2.004 |
| F(000) | 444 |
| Crystal size (mm$^3$) | 0.36 × 0.16 × 0.03 |
| Reflections used for cell measurement | 7034 |
| θ range for cell measurement | 5.0710°-77.0390° |
| Total reflections collected | 10895 |
| Index ranges | −9 ≤ h ≤ 8; −9 ≤ k ≤ 9; −22≤l≤22 |
| θ range for data collection | $θ_{min}$ = 5.068°, $θ_{max}$ = 77.339° |
| Completeness to $θ_{max}$ | 98.7% |
| Completeness to $θ_{full}$ = 67.684° | 99.2% |
| Absorption correction | multi-scan |
| Transmission coefficient range | 0.716-1.000 |
| Refinement method | full matrix least-squares on $F^2$ |
| Independent reflections | 4117 [$R_{int}$ = 0.0267, $R_σ$ = 0.0311] |
| Reflections [ I > 2σ(I) ] | 3854 |
| Reflections/restraints/parameters | 4117/1/274 |
| Goodness-of-fit on $F^2$ | S = 1.06 |
| Final residuals [ I > 2σ(I) ] | R = 0.0389, $R_w$ = 0.1081 |
| Final residuals [ all reflections ] | R = 0.0413, $R_w$ = 0.1106 |
| Largest diff. peak and hole (e Å$^{-3}$) | 0.492, −0.242 |
| Max/mean shift/standard uncertainty | 0.000/0.000 |
| Absolute structure determination | Flack parameter: −0.001(11) |

Figure 10:
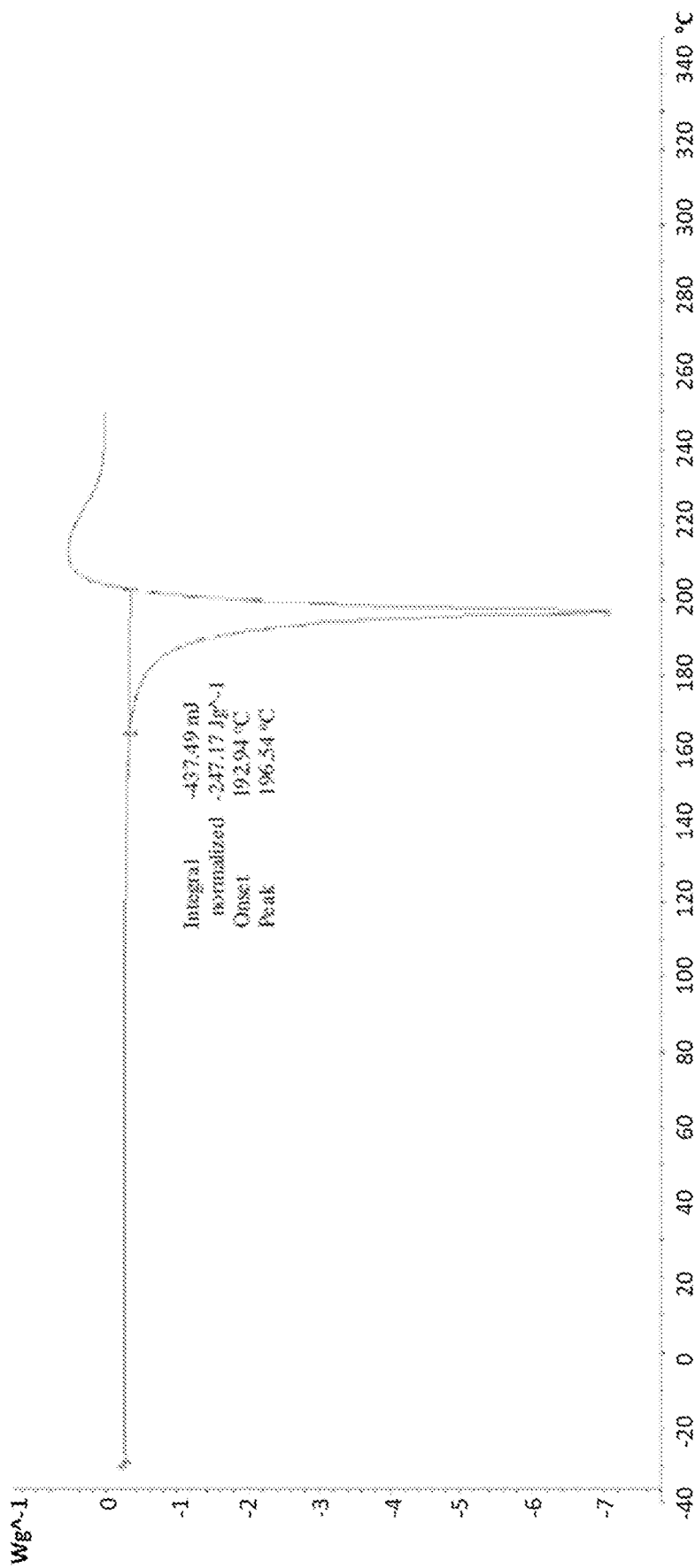
FIG. 10 shows a differential scanning calorimeter (DSC) curve of Compound I HCl Form A.
Figure 11:
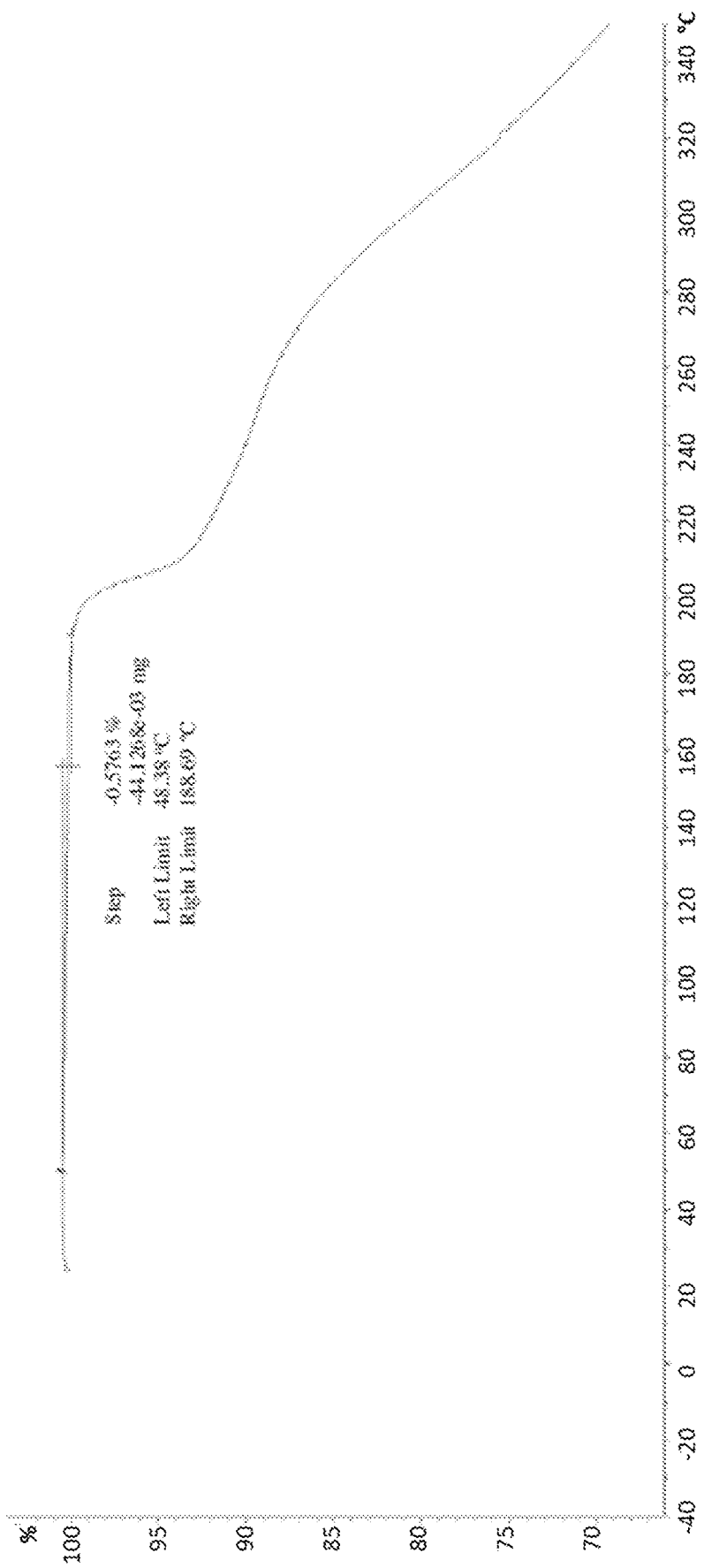
FIG. 11 shows a thermogravimetric analysis (TGA) of Compound I HCl Form A.
Figure 12:
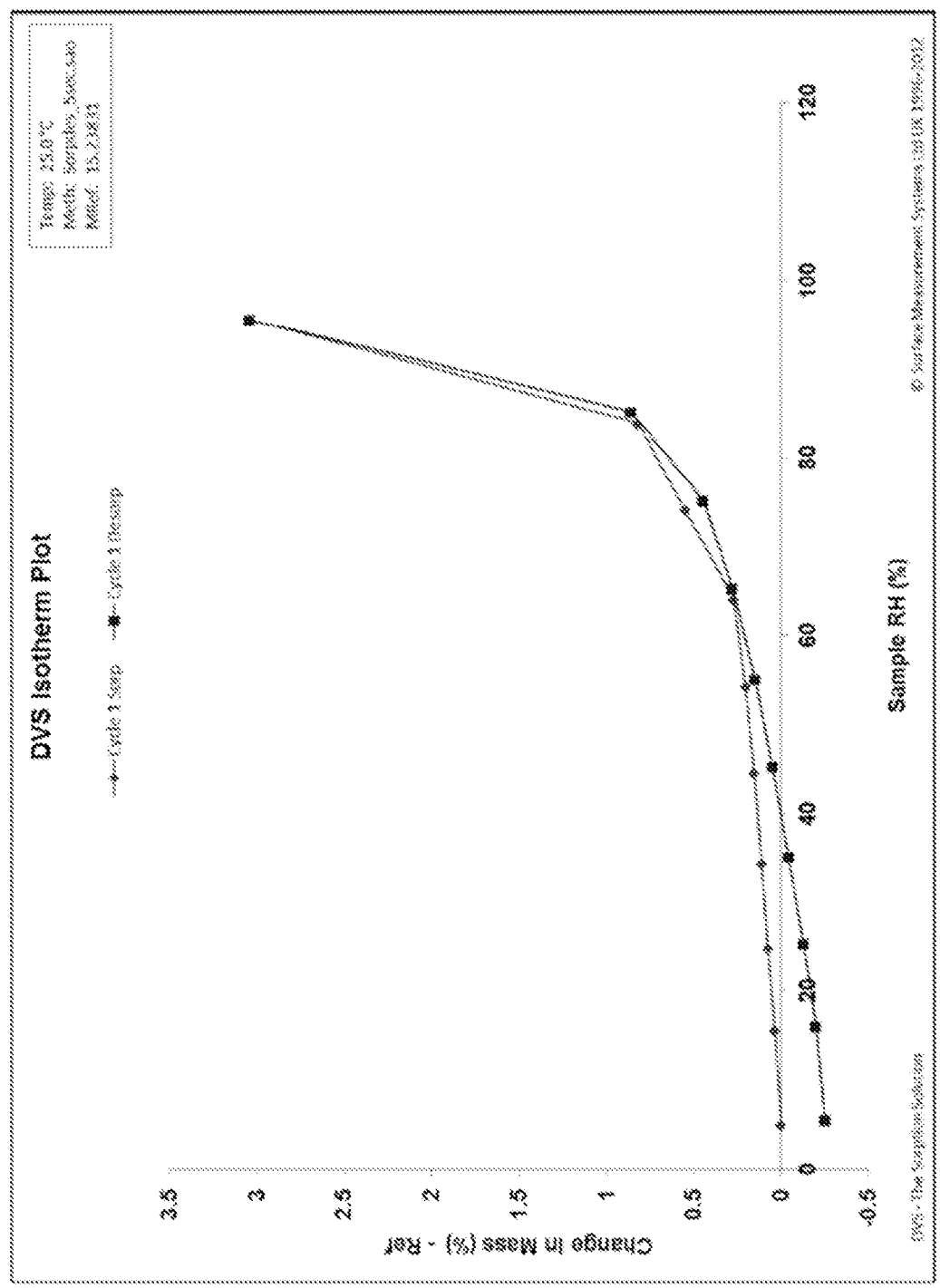
FIG. 12 shows dynamic vapor sorption (DVS plot) of Compound I HCl Form A.

The TGA data of Compound I HCl Form A shows a 0.6% weight loss upon heating up to 188° C. (FIG. 11). The DSC exhibits a single endotherm with an onset near 193° C. (FIG. 10). The DVS isotherm indicates the material exhibits significant hygroscopicity (FIG. 12). A weight gain of 3% is observed during the sorption cycle, the majority of which occurred above 85% RH. Upon desorption a 3.3% weight loss is observed. The material recovered from the DVS experiment remained Compound I HCl Form A by XRPD. Compound I HCl Form A was stressed at 40° C./75% RH for 27 days. The material was observed to be a free flowing powder upon removal and no changes were observed in the XRPD pattern.

Example 5: Salt Screen

Alternative Preparation of Compound I Form I and Salt Screen of Compound I (R)-(2-(2-((tert-butyldiphenylsilyl)oxy)ethyl)pyridin-3-yl)(3-(hydroxymethyl)morpholino)methanone can be synthesized according to the methods described in U.S. Pat. No. 10,683,285, or U.S. Provisional Application No. 63/188,735 (filed on May 14, 2021, and titled "Methods of Making a Modulator of Hemoglobin"), or PCT Application No. PCT/US22/29304 (filed on even date herewith, and titled "Methods of Making a Modulator of Hemoglobin"), all of which are incorporated by reference in their entirety.

In a 50 L reactor, a solution of (R)-(2-(2-((tert-butyldiphenylsilyl)oxy)ethyl)pyridin-3-yl)(3-(hydroxymethyl)morpholino)methanone in THF (6.07 kg in about 30 L THF), 2,6-dihydroxybenzaldehyde (1.2 equiv) and triphenylphosphine (1.3 equiv) were placed. The resulting mixture was warmed to 30° C. To the mixture was added a solution of DIAD in THF (1.3 equiv in about 9 L of THF) dropwise maintaining the temperature between 25° C. and 35° C. The reaction mixture was stirred for 30 min at 30° C. To the reaction mixture was added water (0.6 equiv), and the mixture was stirred for additional 1 h at 30° C.

To the reaction mixture was added a solution of TBAF in THF (0.5 equiv, 1 M solution in THF), and the mixture was stirred for 18 h. The reaction mixture was concentrated to remove most of the THF under vacuum, maintaining the temperature below 50° C. To the residue was added 1.2 N HCl aq. (about 72 L) and toluene (about 30 L). The mixture was stirred for 15 min at 20° C., and the layers were separated. The aqueous layer was extracted with toluene twice (about 30 L per extraction). To the aqueous solution was added DCM (about 90 L), and to the mixture was added potassium carbonate until the pH was between pH 8 and pH 10. The layers were separated. The DCM solution was washed with water (about 30 L) and concentrated under reduced pressure.

The residue was purified by silica gel chromatography (30 kg silica gel, a mixture of ethyl acetate:DCM:methanol=100:20:8 as eluent). This resulted in crude (S)-2-hydroxy-6-((4-(2-(2-hydroxyethyl)nicotinoyl)morpholin-3-yl)methoxy)benzaldehyde.

Crude (S)-2-hydroxy-6-((4-(2-(2-hydroxyethyl)nicotinoyl)morpholin-3-yl)methoxy)benzaldehyde, as an oil (4.4 kg, 11.4 mol), was dissolved in EtOAc (9.11 L). To the resulting solution was added seed crystal of Compound I Form I (prepared as described herein), and the reaction mixture was stirred for 18 h at 15° C.-25° C. The resulting slurry was heated to 35° C.-45° C. and stirred for 18 h. To the slurry was added MTBE (52.8 L), and the mixture was stirred for 18 h maintaining the temperature at 35° C.-45° C. The slurry was cooled to 15° C.-25° C. and stirred for 18 h. The solids were collected by filtration, washed with MTBE (2.2 L) and dried under vacuum at 35° C.-45° C. This resulted in Compound I Form I.

The generation of crystalline salts and cocrystals of Compound I were then attempted with 55 different acidic and neutral coformers. Approximately 115 experiments were conducted (data not shown). The products from the experiments were qualitatively evaluated for crystallinity by PLM and/or XRPD.

In addition to the HCl salt described herein, 13 unique crystalline materials and forms were obtained from 8 different acids, including benzenesulfonic; 1,2-ethanedisulfonic; ethanesulfonic; 1,5-naphthalenedisulfonic; naphthalene-2-sulfonic; oxalic; sulfuric; and p-toluenesulfonic acid. All remaining counterions and coformers failed to provide crystalline material or provided Freebase Form I, the coformer, or a combination of the two.

Compound I Besylate Form A

Solids of Compound I, prepared as described in Example 5 (106.2 mg), were combined with a benzenesulfonic acid/THF solution (54.4 mg in 0.5 mL THF). The resulting solution was left to stir at ambient temperature for 3 days, affording a thick off-white slurry. The slurry was filtered on a 0.2-µm nylon filter in a Swinnex filter holder. The solids were flushed with air (5×20 mL) on the filter. Resulting solids consisted of Compound I Besylate Form A.

Figure 17:
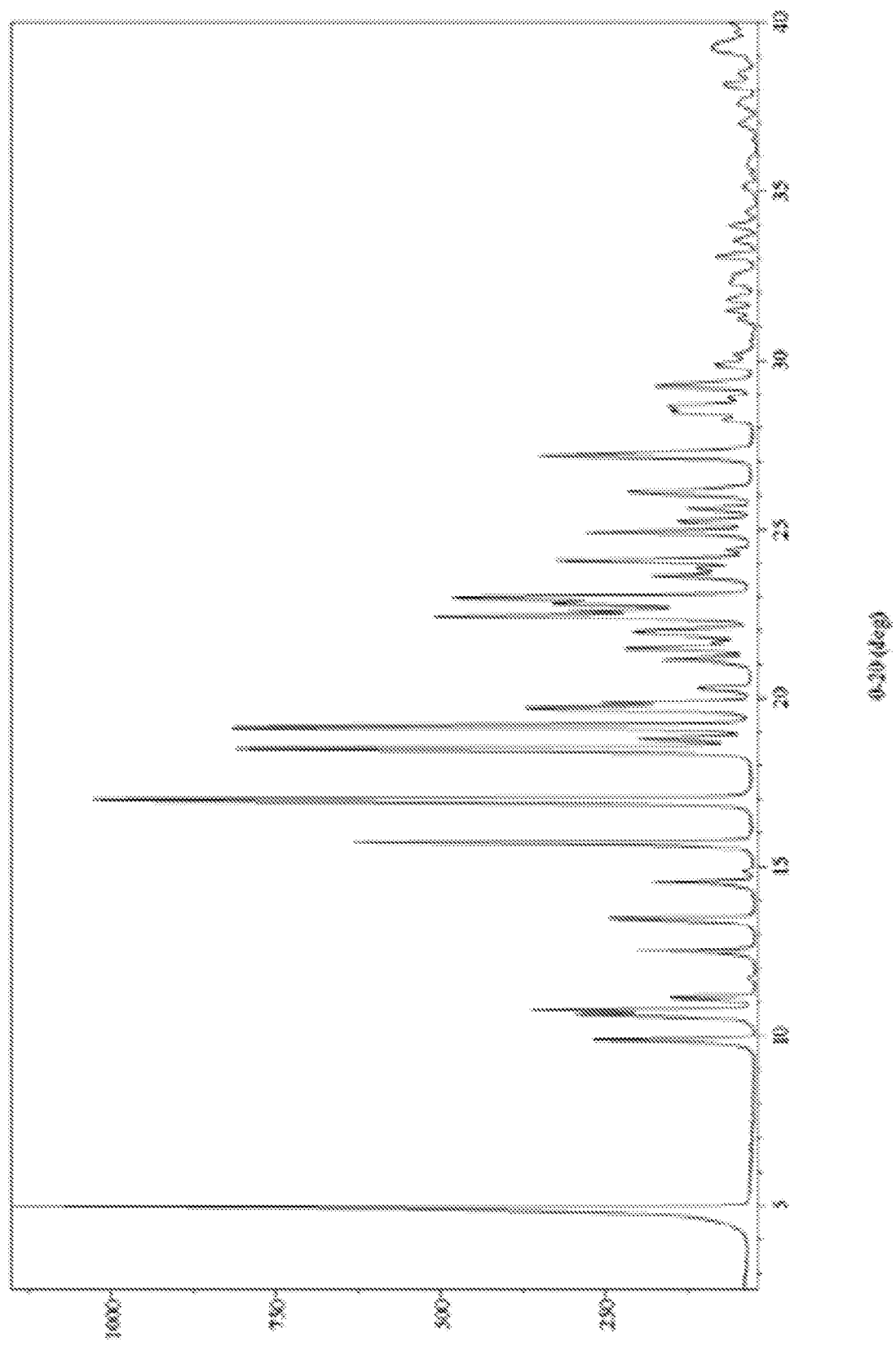
FIG. 17 shows an X-ray powder diffraction (XRPD) of Compound I Besylate Form A.

Compound I Besylate Form A is a 1:1 besylate salt of Compound I (FIG. 17). Compound I Besylate Form A appears to be a hemiTHF solvate; however, the unit cell volume is variable and likely compensates for differences in solvent content. An XRPD pattern (data not shown) displayed peak shifting to the right for the sample exposed to 44° C. under vacuum, associated with a decrease in the volume of the unit cell. The crystal structure is isostructural with Compound I Tosylate Form A and Compound I Esylate Forms A & B.

The stoichiometry of benzenesulfonic acid in Compound I Besylate Form A was confirmed by solution state proton nuclear magnetic resonance spectroscopy. The doublet at approximately 6.75 ppm corresponds with 1 proton in Compound I and integrates to 100. The multiplets at approximately 7.6 ppm and 7.31 ppm correspond with 5 protons in benzenesulfonic acid. These peaks integrate to a total of 484.21. The ratio of Compound I/benzenesulfonic acid, based on integration per proton, is 100:96.84 or 1:1. This sample also displayed multiplets at approximately 3.60 ppm and 1.75 ppm that correspond with 8 protons in THF. These peaks integrate to a total of 367.08. The ratio of Compound I/THF, based on integration per proton, is 100:45.89 or 1:0.5.

Figure 18:
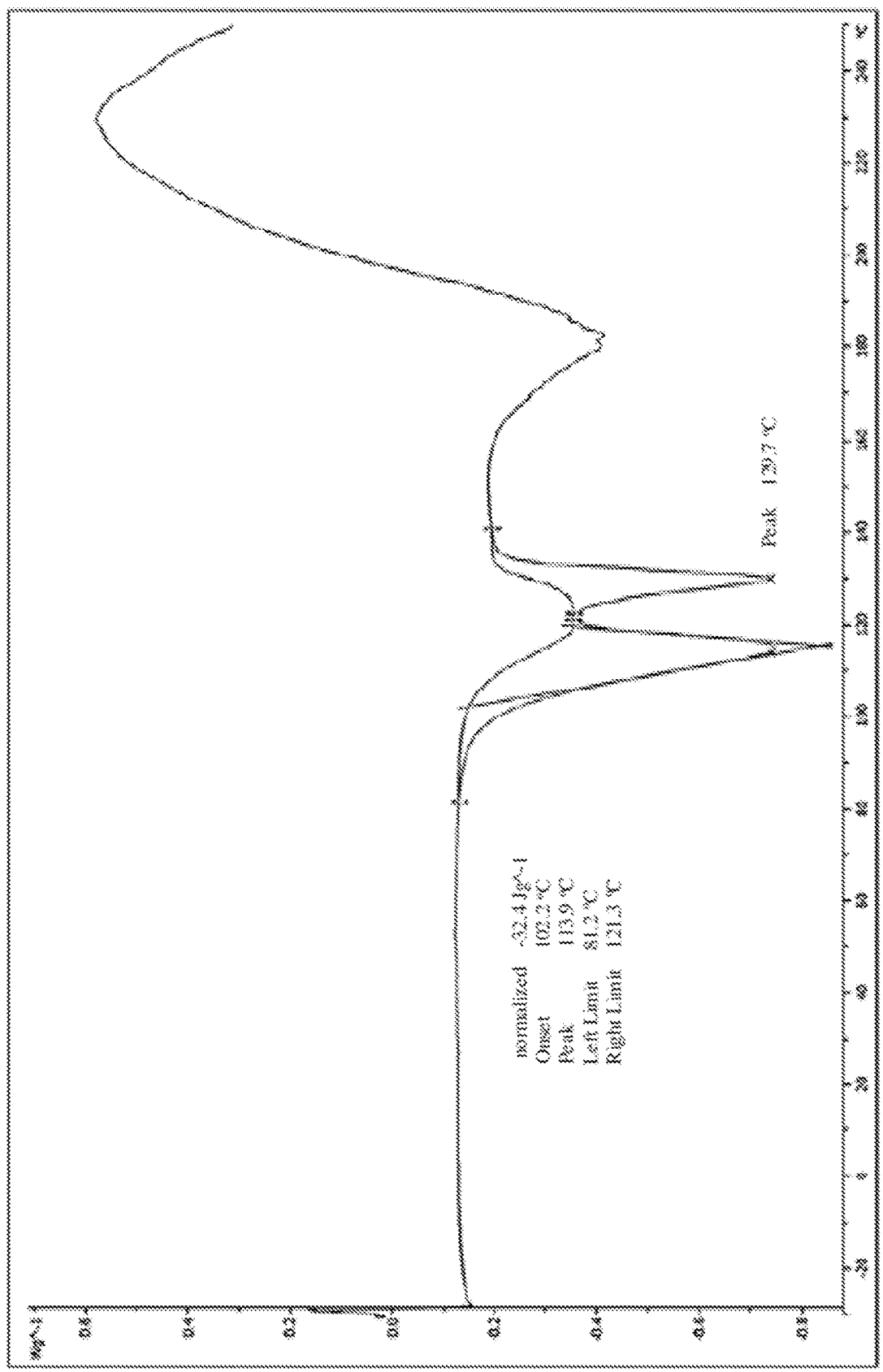
FIG. 18 shows a differential scanning calorimeter (DSC) curve of Compound I Besylate Form A.
Figure 19:
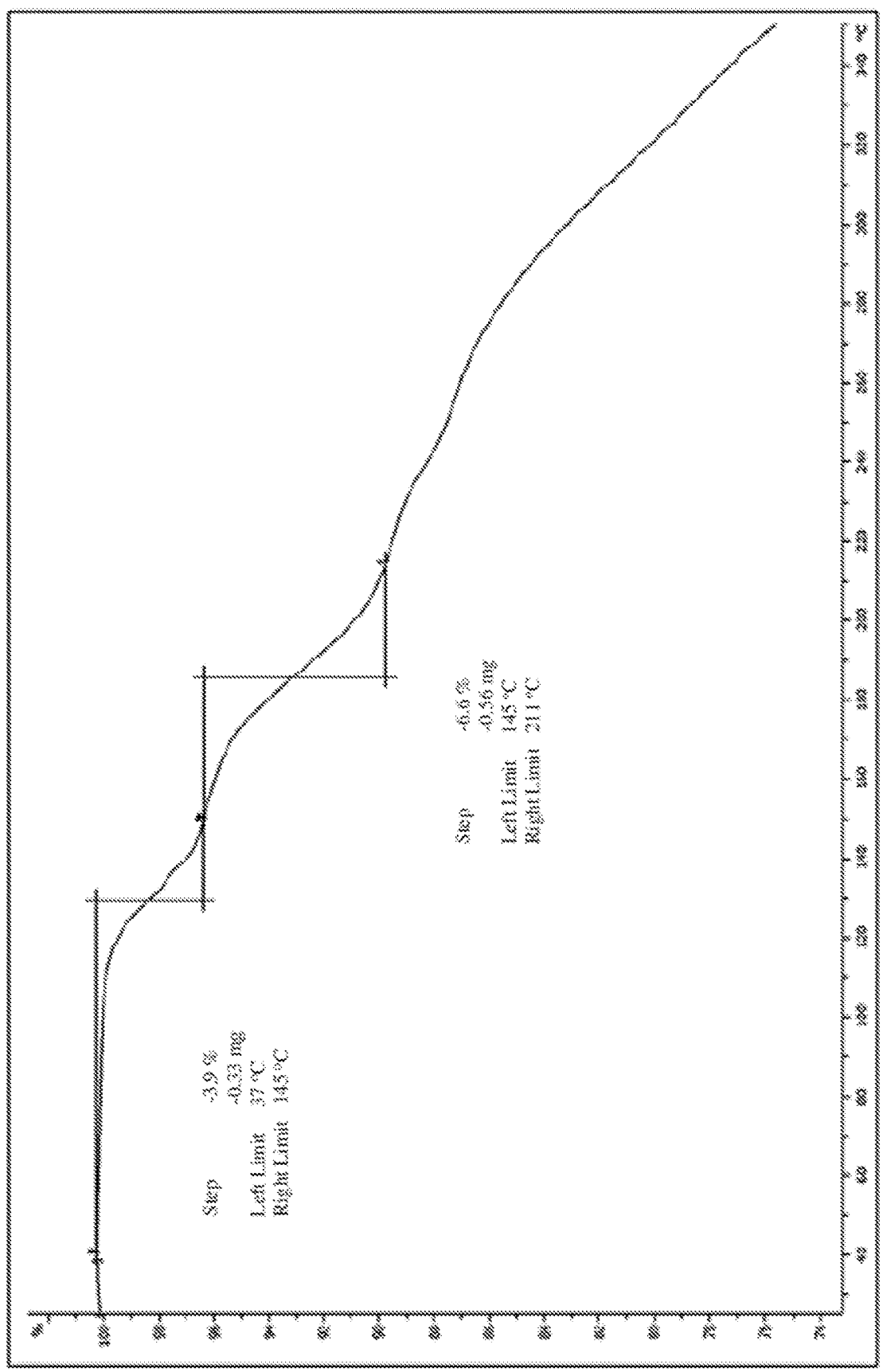
FIG. 19 shows a thermogravimetric analysis (TGA) of Compound I Besylate Form A.

Differential scanning calorimetry of the solvated sample showed two small endotherms at 113.9° C. and 129.7° C. (FIG. 18). Negligible weight loss was seen by thermogravimetric analysis up to approximately 85° C. (FIG. 19). A two-step weight loss was observed from approximately 85° C. to 211° C. From 37° C. to 145° C., 3.9% weight loss was observed. A 6.6% weight loss was observed from 145° C. to 211° C. The 3.9% weight loss is consistent with 0.3 mol of THF per mol of Compound I. This is slightly lower than what was observed by NMR due to the previously noted variability in the unit cell size.

Compound I Edisylate Form A

A solution of 1,2-ethanedisulfonic acid in EtOH (54.1 mg in 1 mL EtOH) was added to solids of Compound I, prepared as described in Example 5 (105.1 mg). The off-white slurry was stirred for 2 days. After 2 days, the slurry had turned pink. The slurry was filtered on a 0.2-µm nylon filter in a Swinnex filter holder. The solids were flushed with air (5×20 mL) on the filter. Resulting damp solids consisted of Compound I Edisylate Form A.

Figure 20:
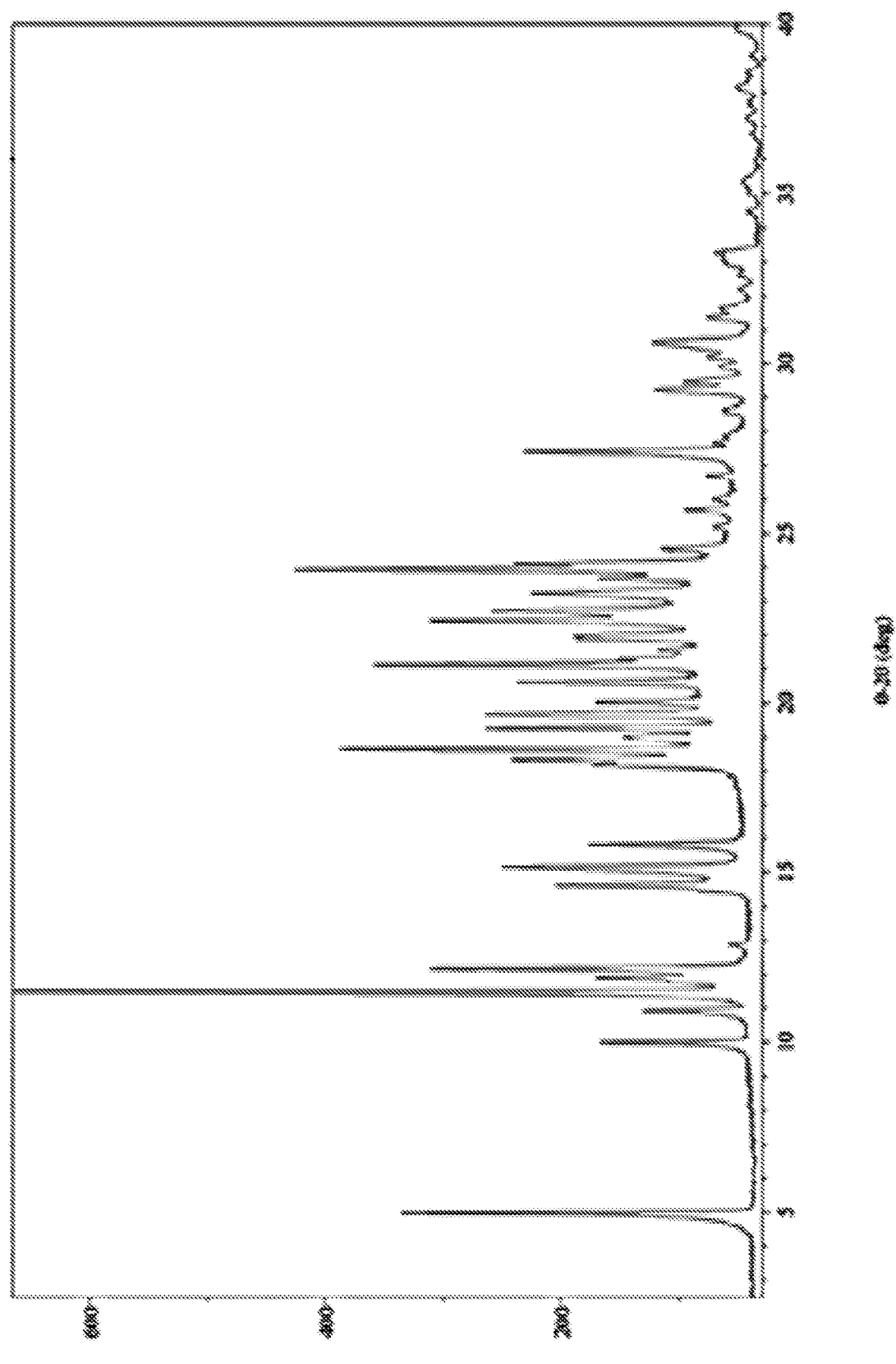
FIG. 20 shows an X-ray powder diffraction (XRPD) of Compound I Edisylate Form A.

Compound I Edisylate Form A is a metastable 1:1 edisylate salt of Compound I (FIG. 20). The sample consisted of slightly damp pink solids. Although characterized with excess solvent, Compound I Edisylate Form A is tentatively described as anhydrous.

An XRPD pattern (data not shown) of slightly damp material was successfully indexed with a unit cell volume consistent with an anhydrous 1:1 edisylate. The stoichiometry of 1,2-ethanedisulfonic acid in Compound I Edisylate Form A was confirmed by solution state proton nuclear magnetic resonance spectroscopy. The doublet at approximately 6.75 ppm corresponds with 1 proton in Compound I and integrates to 100. The singlet at 2.68 ppm corresponds with 4 protons in 1,2-ethanedisulfonic acid. This peak integrates to 282.188. The ratio of Compound I/1,2-ethanedisulfonic acid, based on integration per proton, is 100:70.547 or 1:0.7. Excess ethanol is evident.

The DSC (FIG. 21) and TGA (FIG. 22) thermograms of the damp sample displayed thermal instability after 91.4° C. A weight loss of 0.8% was observed in the TGA from 39° C. to 91° C. Both experiments caused the material to expand out of the sample pan upon heating.

The physical stability of Compound I Edisylate Form A was investigated. The solids became very tacky upon exposure to ambient conditions with a relative humidity level of approximately 57%. This indicates that Compound I Edisylate Form A is very hygroscopic and not stable under ambient conditions. Drying the damp sample in a 43° C. vacuum oven showed physical instability with additional unidentifiable peaks present in the X-ray pattern of the resulting material (data not shown). This is likely attributed to the thermal instability observed when obtaining differential scanning calorimetry and thermogravimetric analysis, as noted above.

Compound I Edisylate Material B

A THF solution of solids of Compound I, prepared as described in Example 5 (99.0 mg in 0.5 mL THF), was added to 1,2-ethanedisulfonic acid solids (62.1 mg), and the resulting slurry was left to stir at ambient temperature for 2 days, providing dark orange solids in clear solution. The solution was decanted by disposable pipette and the remaining solids were briefly dried under $N_2$. Resulting sticky solids consisted of Compound I Edisylate Material B.

Figure 23:
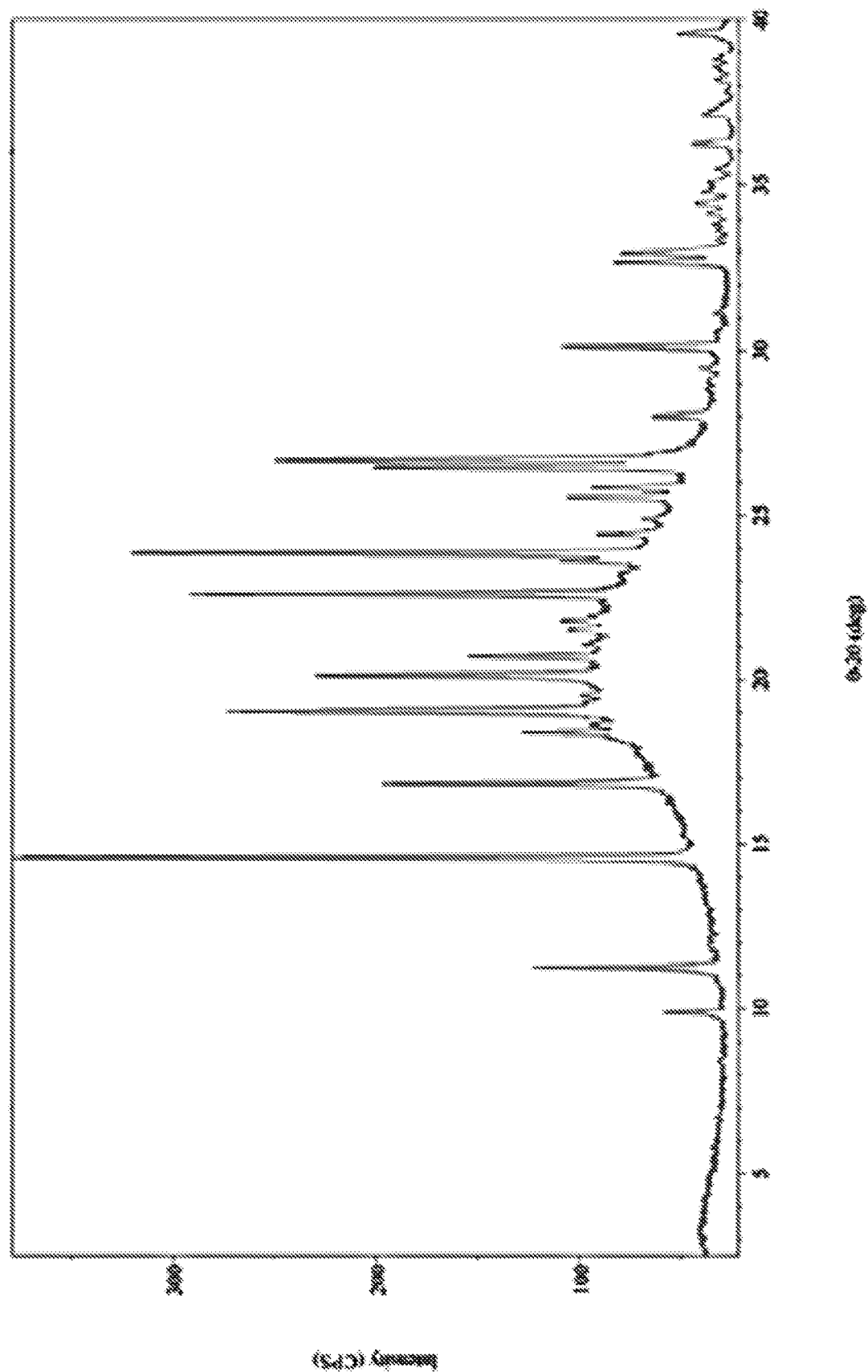
FIG. 23 shows an X-ray powder diffraction (XRPD) of Compound I Edisylate Material B.

Compound I Edisylate Material B is likely an anhydrous 1:1 edisylate salt of Compound I (FIG. 23).

The stoichiometry of 1,2-ethanedisulfonic acid in Compound I Edisylate Material B was confirmed by solution state proton nuclear magnetic resonance spectroscopy. The doublet at approximately 6.75 ppm corresponds with 1 proton in Compound I and integrates to 100. The singlet at 2.68 ppm corresponds with 4 protons in 1,2-ethanedisulfonic acid. This peak integrates to 484.380. The ratio of Compound I/1,2-ethanedisulfonic acid, based on integration per proton, is 100:121.095 or 1:1.2.

Figure 24:
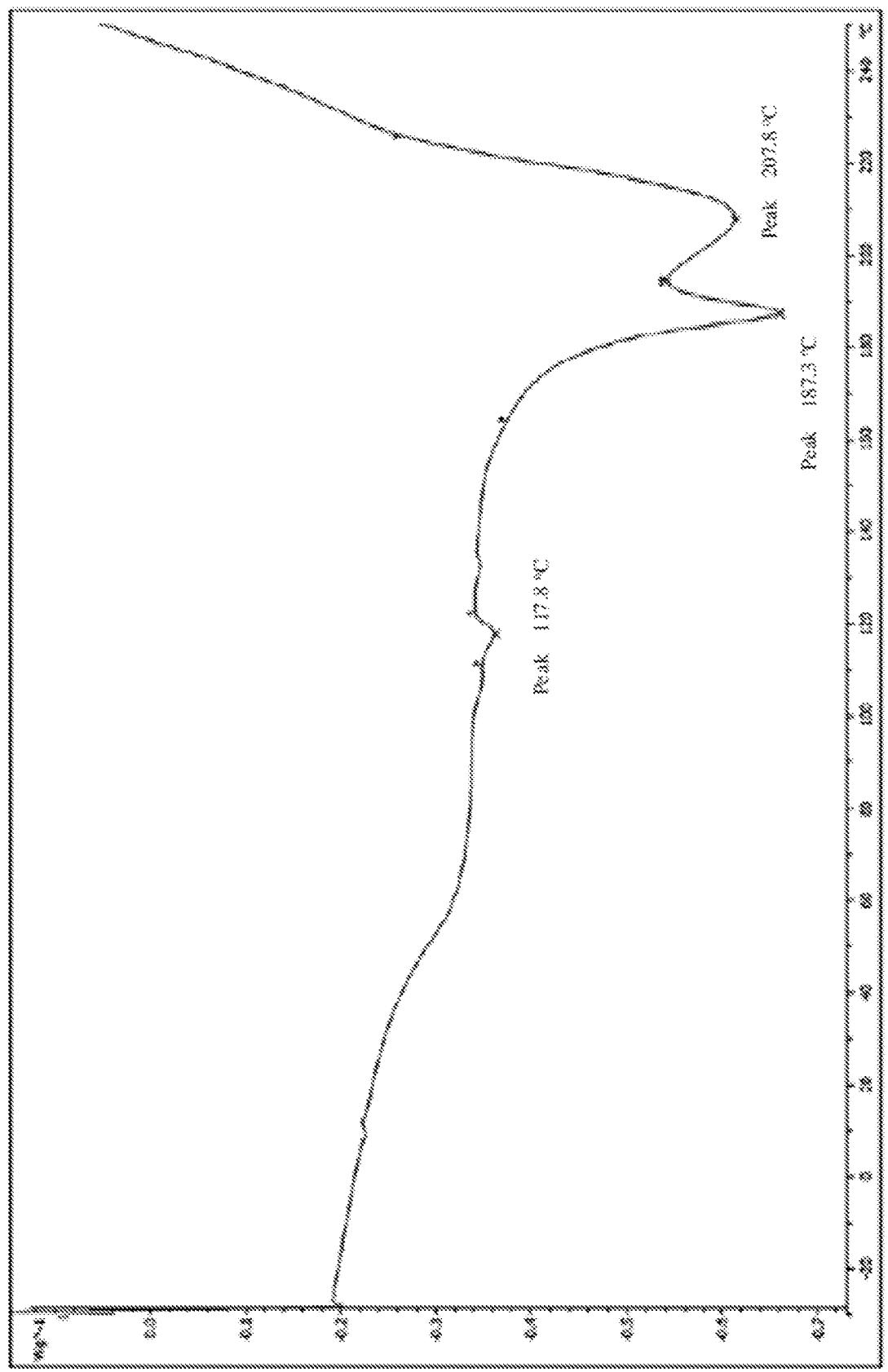
FIG. 24 shows a differential scanning calorimeter (DSC) curve of Compound I Edisylate Material B.
Figure 25:
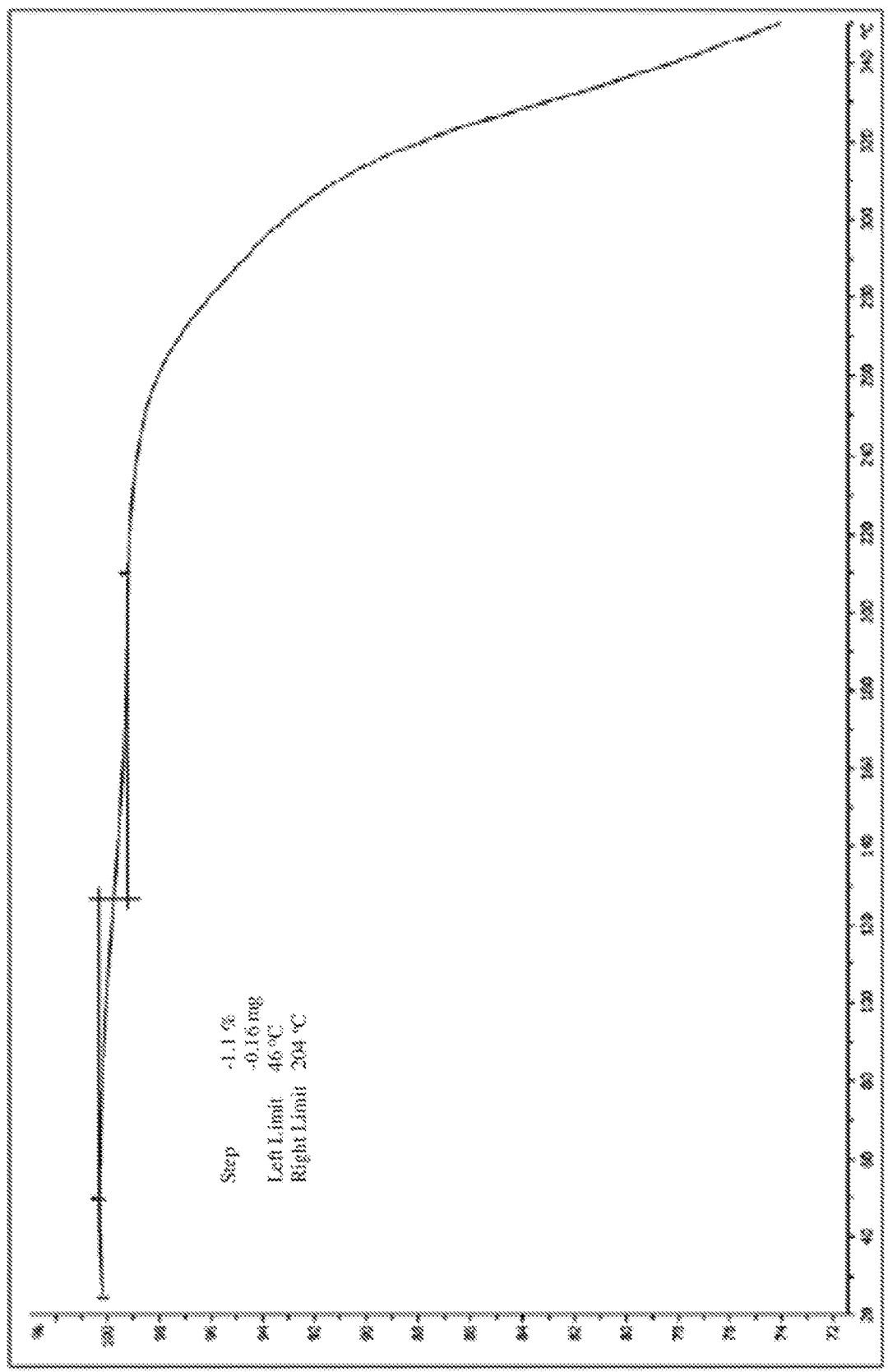
FIG. 25 shows a thermogravimetric analysis (TGA) of Compound I Edisylate Material B.

Differential scanning calorimetry displayed three broad, shallow endotherms at 117.8° C., 187.3° C., and 207.8° C. (FIG. 24). Thermogravimetric analysis of the dried sample displayed a 1.1% weight loss over 46 to 204° C. (FIG. 25). This weight loss is likely due to water, suggesting this material may be hygroscopic as well. This can be further observed through physical stability testing in different temperature vacuum ovens (data not shown). Compound I Edisylate Material B exposed to 44° C. under vacuum provided Compound I Edisylate Material B with additional unidentified peaks by XRPD. These extra peaks were no longer evident after further drying at 80° C. under vacuum. It is likely that the unidentified peaks were the result of Compound I Edisylate Material B picking up water due to hygroscopicity, before the XRPD was obtained.

Compound I Esylate Form A

Solids of Compound I, prepared as described in Example 5 (107.4 mg), were slurried in IPA (2 mL) at ambient temperature. Ethanesulfonic acid (24.5 µL) was added to the slurry. The mixture was stirred for 5 days resulting in a pale pink slurry. The slurry was filtered on a 0.2 µm nylon filter in a Swinnex filter holder. The solids were flushed with air (5×20 mL) on the filter. Resulting solids consisted of Compound I Esylate Form A.

Figure 26:
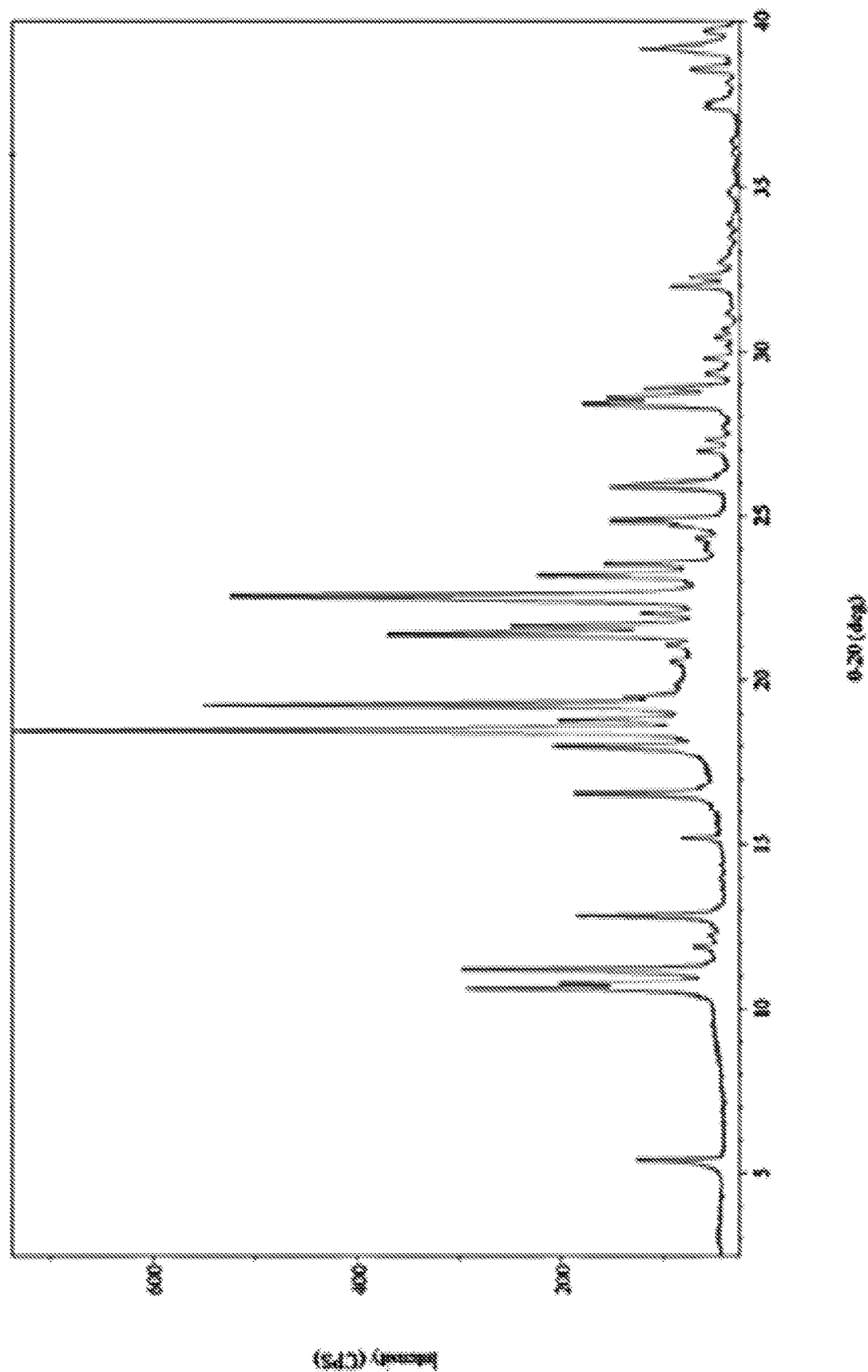
FIG. 26 shows an X-ray powder diffraction (XRPD) of Compound I Esylate Form A.

Compound I Esylate Form A consists of an IPA solvate of a 1:1 esylate salt of Compound I (FIG. 26). The IPA stoichiometry varied between analyses and could not be confirmed. In addition, the unit cell volume was shown to vary and likely compensates for differences in solvent content. An XRPD pattern (data not shown) displayed slight shifting of the indexed peaks in a sample that was desolvated in a 44° C. vacuum oven and reflects a slightly smaller unit cell. Additional peaks were also evident, which suggests that the solvate is not physically stable. The form is isostructural with Compound I Besylate Form A, Compound I Esylate Form B, and Compound I Tosylate Form A.

The stoichiometry of ethanesulfonic acid in Compound I Esylate Form A was confirmed by solution state proton nuclear magnetic resonance spectroscopy. The doublet at approximately 6.75 ppm corresponds with 1 proton in Compound I and integrates to 100. The quartet at approximately 2.4 ppm and triplet at approximately 1.07 ppm correspond with 5 protons in ethanesulfonic acid. These peaks integrate to 632.905. The ratio of Compound I/ethanesulfonic acid, based on integration per proton, is 100:126.581 or 1:1.3. This sample also displayed a doublet at approximately 1.04 ppm that corresponds with 6 protons in IPA. These peaks integrate to a total of 1794.425. The ratio of Compound I/IPA, based on integration per proton, is 100:299.071 or 1:3.

Figure 27:
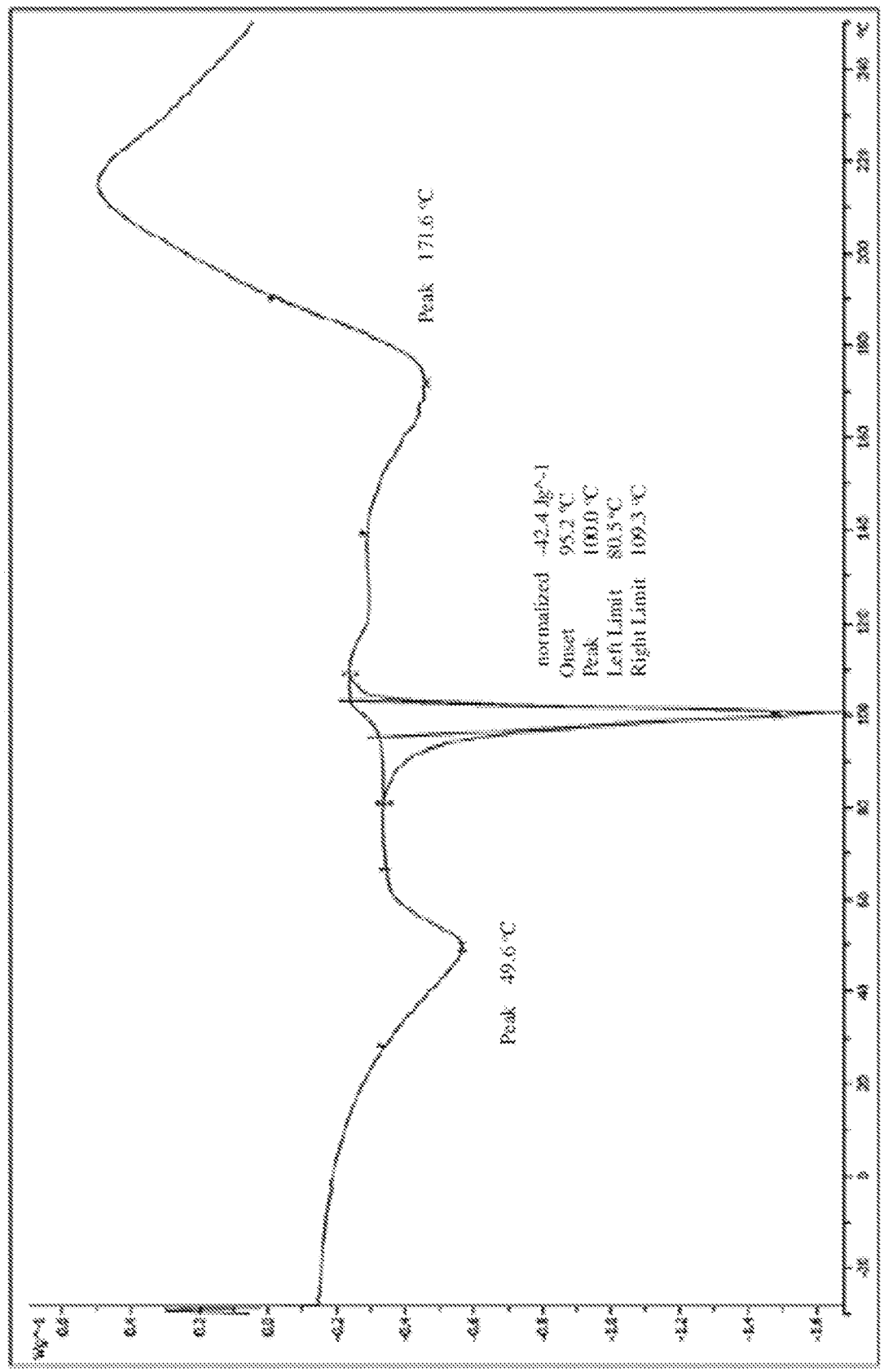
FIG. 27 shows a differential scanning calorimeter (DSC) curve of Compound I Esylate Form A.
Figure 28:
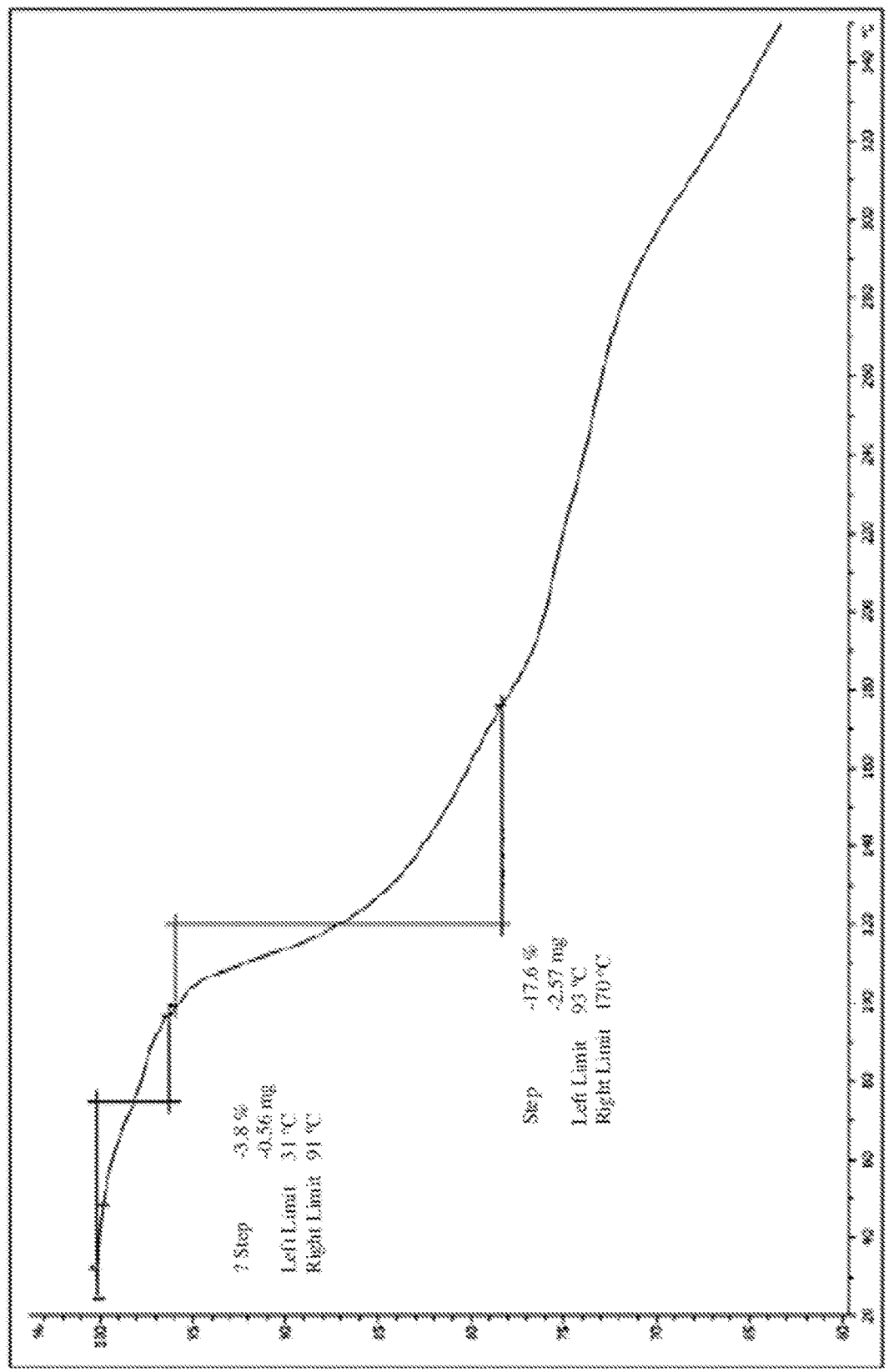
FIG. 28 shows a thermogravimetric analysis (TGA) of Compound I Esylate Form A.

Differential scanning calorimetry of the solvated sample showed two broad, shallow endotherms at 49.6° C. and 171.6° C. and a sharper endotherm at 100.0° C. (FIG. 27). A two-step weight loss was observed by thermogravimetric analysis from approximately 31° C. to 91° C. and from 93° C. to 170° C. (FIG. 28). From approximately 31° C. to 91° C., 3.8% weight loss was observed and from 93° C. to 170° C., 17.6% weight loss was observed. This is consistent with a loss of 2.1 moles of IPA per mole of Compound I. The discrepancy between the IPA content observed in both the NMR and the TGA further supports that Compound I Esylate Form A is a variable solvate.

Compound I Esylate Form B

Solids of Compound I, prepared as described in Example 5 (128.1 mg), were dissolved in acetone (1 mL) at ambient temperature with sonication. Ethanesulfonic acid (29.0 µL) was added to the solution. The solution was stirred for 1 day, resulting in an off-white slurry. The slurry was filtered on a 0.2-µm nylon filter in a Swinnex filter holder. The solids were flushed with air (5×20 mL) on the filter. Resulting solids consisted of Compound I Esylate Form B.

Figure 29:
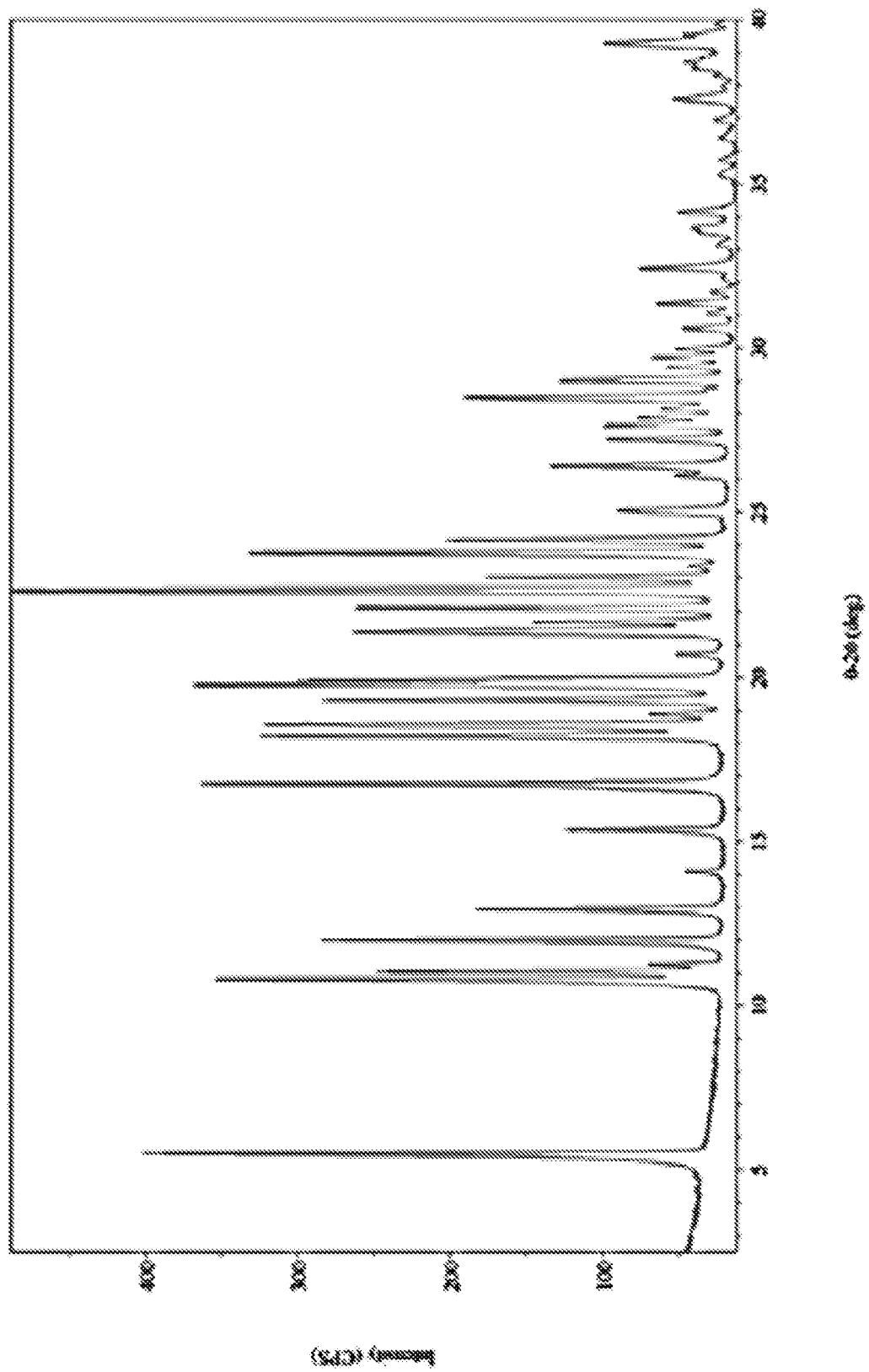
FIG. 29 shows an X-ray powder diffraction (XRPD) of Compound I Esylate Form B.

Compound I Esylate Form B consists of a 1:1 esylate salt of Compound I (FIG. 29). Compound I Esylate Form B also appears isostructural with Compound I Esylate Form A, Compound I Besylate Form A, and Compound I Tosylate Form A. Due to structural similarities with these variable solvates, it is highly likely that Compound I Esylate Form B is a variable hemiacetone solvate. The unit cell volume is shown to compensate for differences in solvent content through peak shifting (data not shown). Physical stability of Compound I Esylate Form B was also assessed under 90% relative humidity conditions at ambient temperature. Under these conditions, the sample deliquesced and is therefore very hygroscopic.

The stoichiometry of ethanesulfonic acid in Compound I Esylate Form B was confirmed by solution state proton nuclear magnetic resonance spectroscopy. The doublet at approximately 6.75 ppm corresponds with 1 proton in Compound I and integrates to 100. The quartet at approximately 2.42 ppm and triplet at approximately 1.07 ppm correspond with 5 protons in ethanesulfonic acid. These peaks integrate to 382.97. The ratio of Compound I/ethanesulfonic acid, based on integration per proton, is 100:76.594 or 1:0.8. A singlet at 2.09 ppm, corresponding with 6 protons in acetone, was also present. This peak integrates to 184.94. The ratio of Compound I/acetone, based on integration per proton, is 100:30.823 or 1:0.3.

Figure 30:
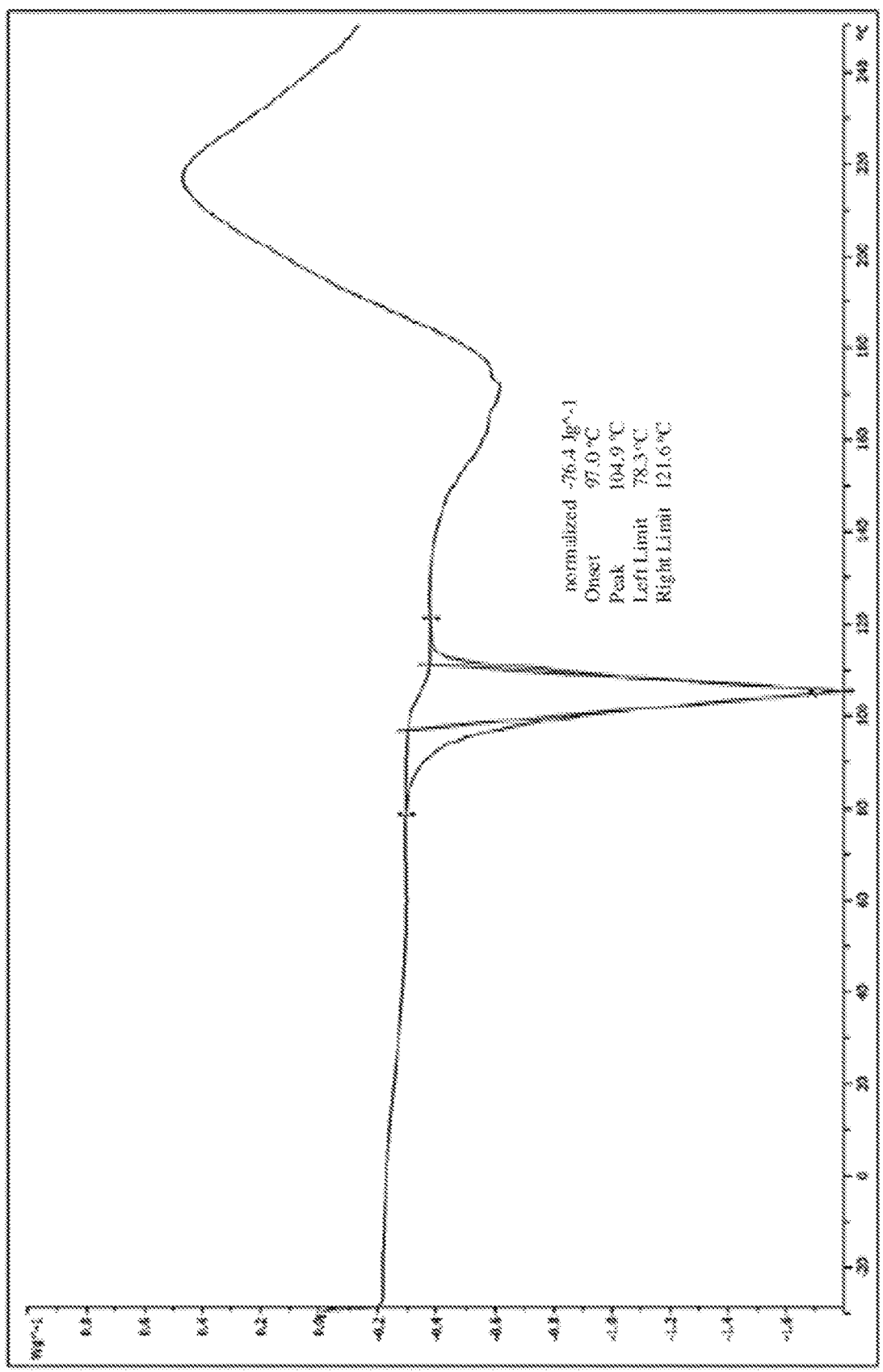
FIG. 30 shows a differential scanning calorimeter (DSC) curve of Compound I Esylate Form B.
Figure 31:
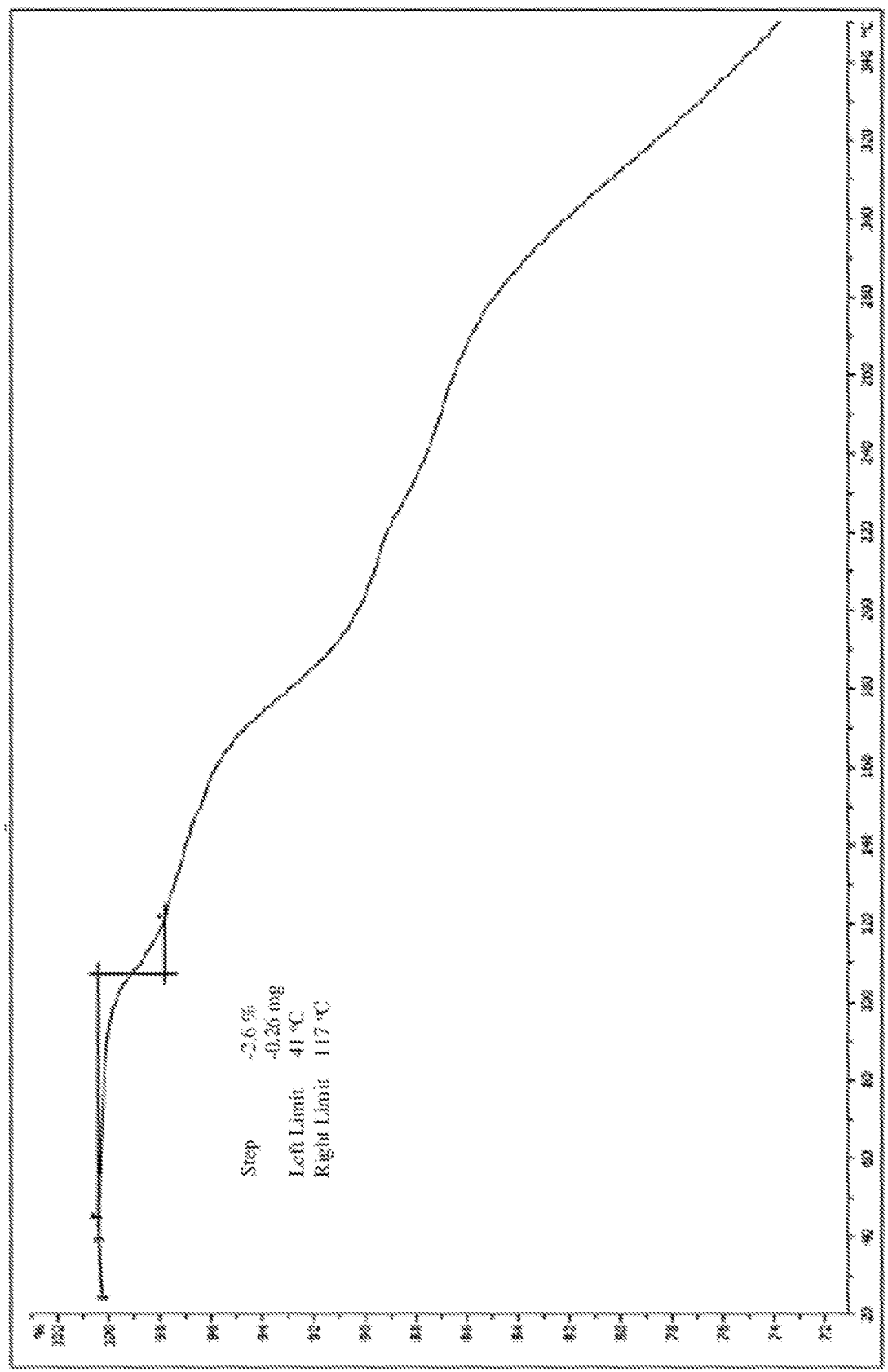
FIG. 31 shows a thermogravimetric analysis (TGA) of Compound I Esylate Form B.

Differential scanning calorimetry of the sample showed a slightly broad endotherm with an onset at 97.0° C. (FIG. 30). A small weight loss of 2.6% over 41° C. to 117° C. was seen by thermogravimetric analysis (FIG. 31). This was calculated to be 0.23 mol/mol acetone. The discrepancy between the acetone content observed in both the NMR and the TGA further supports that Compound I Esylate Form B is a variable solvate.

Compound I Napadisylate Form A

A solution of naphthalene-1,5-disulfonic acid in EtOH (95.4 mg in 1 mL EtOH) was added to solids of Compound I, prepared as described in Example 5 (98.8 mg). The mixture was stirred at ambient temperature for 2 days. After 2 days, the mixture was a pink slurry. The slurry was filtered on a 0.2-µm nylon filter in a Swinnex filter holder. The solids were flushed with air (5×20 mL) on the filter. The resulting solids consisted of Compound I Napadisylate Form A.

Figure 32:
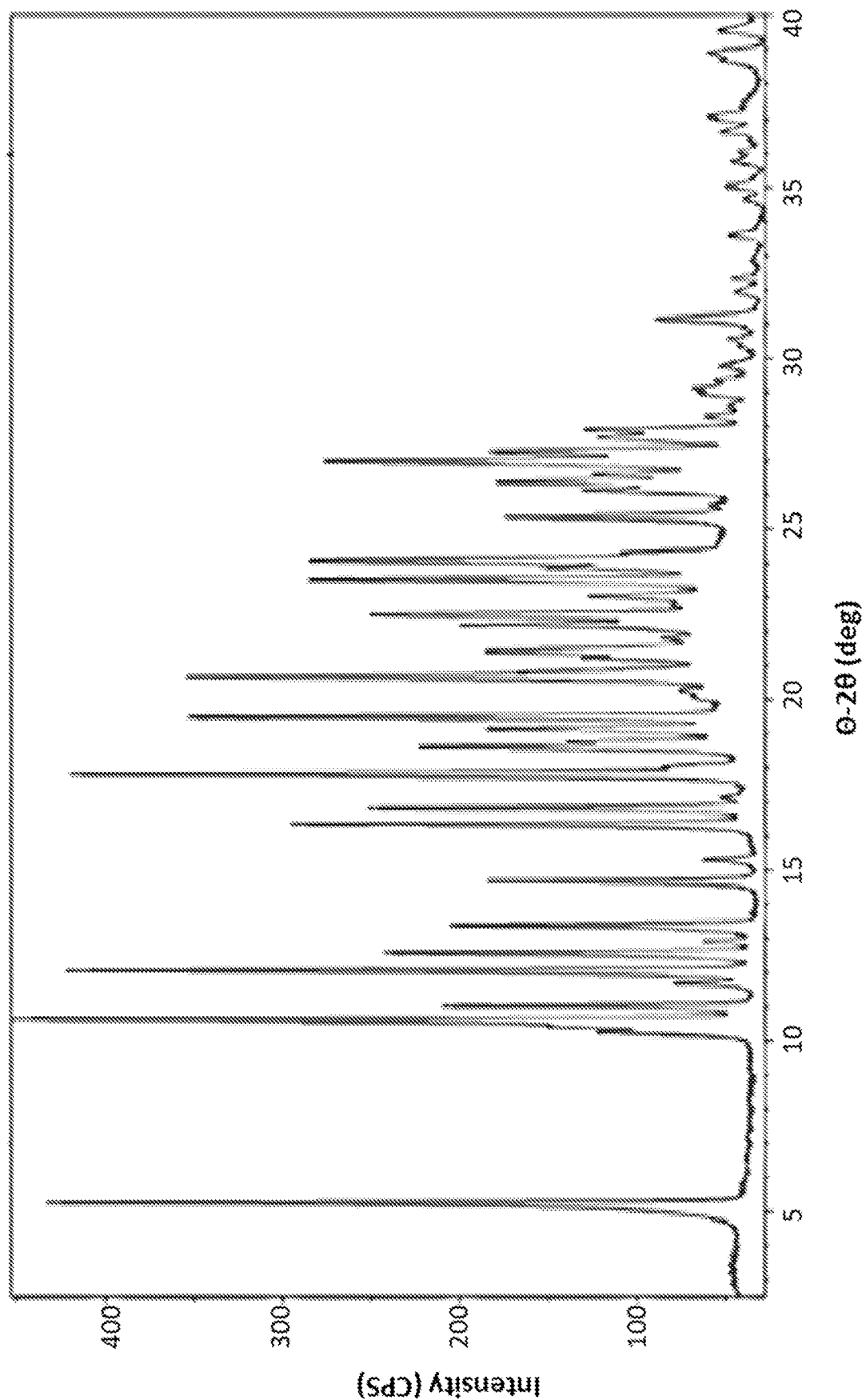
FIG. 32 shows an X-ray powder diffraction (XRPD) of Compound I Napadisylate Form A.

Compound I Napadisylate Form A consists of an ethanol solvate of a 1:1 napadisylate salt of Compound I (FIG. 32). An XRPD pattern of the material was successfully indexed with a unit cell volume consistent with solvated 1:1 napadisylate salt. The ethanol stoichiometry appears to be 3 mol/mol or more. The solvate is not physically stable upon exposure to 43° C. under vacuum and additional unknown peaks become evident by XRPD within 4 days (data not shown). No noticeable shifting was observed for the peaks associated with Compound I Napadisylate Form A, suggesting that the solvate is not variable.

The stoichiometry of naphthalene-1,5-disulfonic acid in Compound I Napadisylate Form A was confirmed by solution state proton nuclear magnetic resonance spectroscopy. The doublet at approximately 6.75 ppm corresponds with 1 proton in Compound I and integrates to 100. The doublets at approximately 8.96 ppm & 7.93 ppm, and the triplet at approximately 7.41 ppm, correspond with 6 protons in naphthalene-1,5-disulfonic acid. These peaks integrate to 449.158. The ratio of Compound I/naphthalene-1,5-disulfonic acid, based on integration per proton, is 100:74.90 or 1:0.7. This sample also displayed a quartet at approximately 3.45 ppm and a triplet at approximately 1.06 ppm that correspond with 5 protons in EtOH. These peaks integrate to a total of 1754.551. The ratio of Compound I/EtOH, based on integration per proton, is 100:350.9 or 1:3.5.

Figure 33:
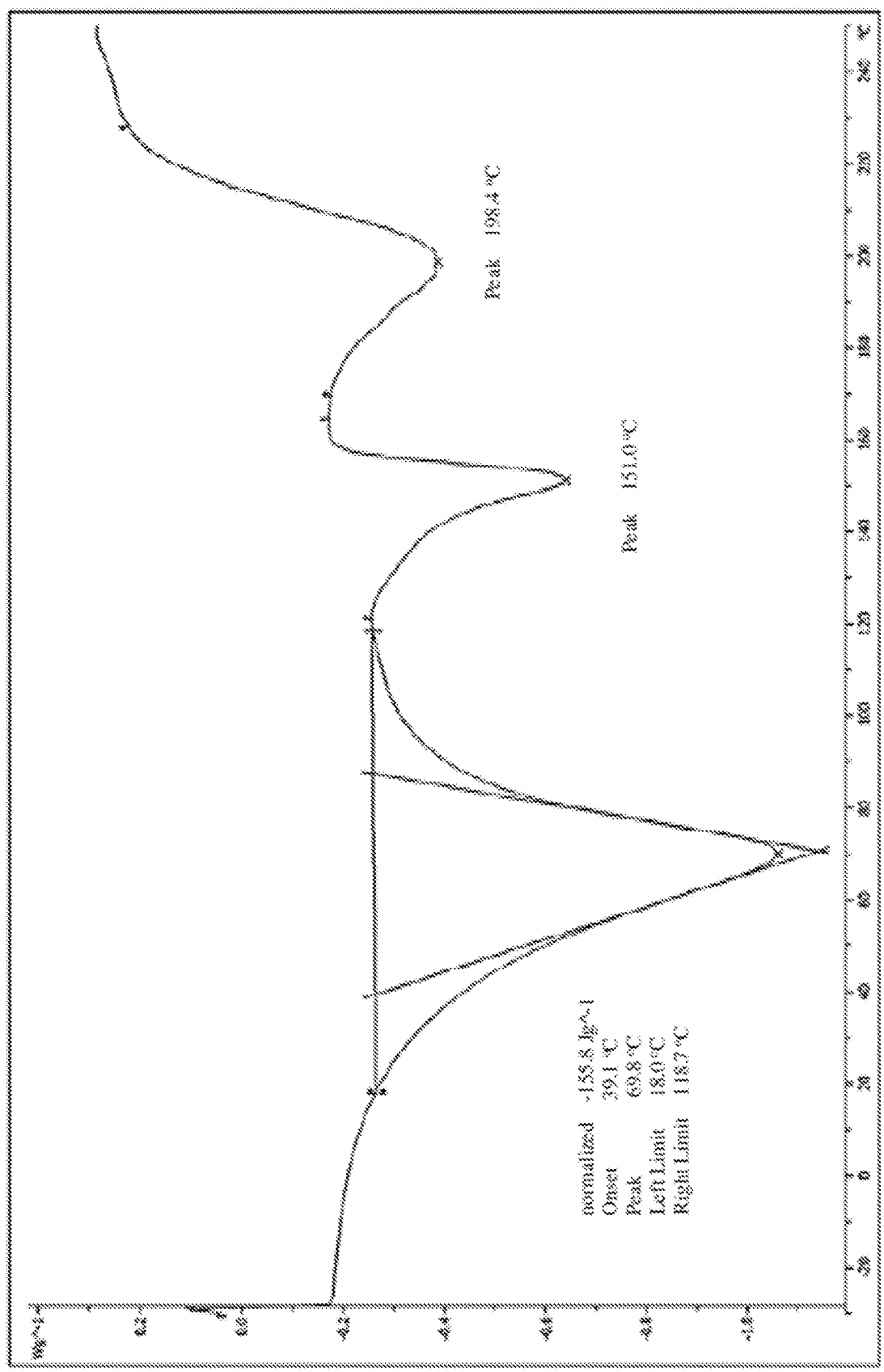
FIG. 33 shows a differential scanning calorimeter (DSC) curve of Compound I Napadisylate Form A.

Differential scanning calorimetry of the solvated sample showed three broad endotherms at 69.8° C., 151.0° C., and 198.4° C. (FIG. 33). A three-step weight loss was seen by thermogravimetric analysis (FIG. 34), coinciding with the endotherms observed in the DSC. First, a 16.9% weight loss was seen from 30° C. to 117° C., followed by a 5.9% weight loss from 117° C. to 162° C., and a 3.7% weight loss from 163° C. to 225° C. This is consistent with a loss of 3 moles of ethanol per mole of Compound I.

Compound I Napadisylate Material B

Solids of Compound I, prepared as described in Example 5 (98.1 mg), were combined with a naphthalene-1,5-disulfonic acid/THF solution (50.2 mg in 0.5 mL THF), and the resulting solution was left to stir at ambient temperature for 2 days, affording an off-white slurry. The slurry was filtered on a 0.2-μm nylon filter in a Swinnex filter holder. The solids were flushed with air (5×20 mL) on the filter. Resulting solids consisted of Compound I Napadisylate Material B.

Figure 35:
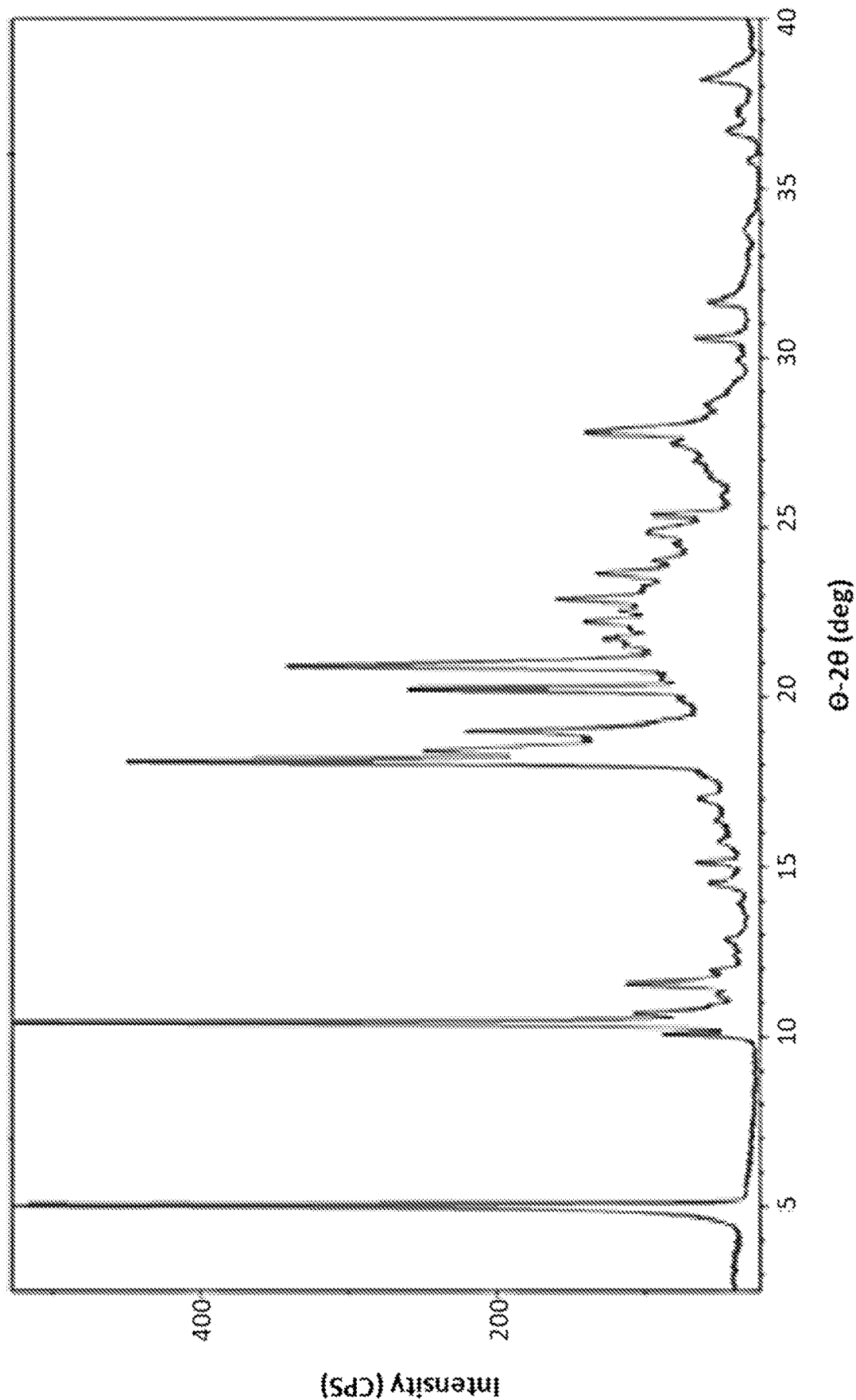
FIG. 35 shows an X-ray powder diffraction (XRPD) of Compound I Napadisylate Material B.

Compound I Napadisylate Material B is a likely THF solvate of a 1:1 napadisylate salt of Compound I (FIG. 35). The XRPD pattern of the material was not successfully indexed and phase purity could not be confirmed.

The stoichiometry of naphthalene-1,5-disulfonic acid in Compound I Napadisylate Material B was confirmed by solution state proton nuclear magnetic resonance spectroscopy. The doublet at approximately 6.75 ppm corresponds with 1 proton in Compound I and integrates to 100. The doublets at approximately 8.85 ppm & 7.90 ppm, and the triplet at approximately 7.4 ppm, correspond with 6 protons in naphthalene-1,5-disulfonic acid. These peaks integrate to 476.767. The ratio of Compound I/naphthalene-1,5-disulfonic acid, based on integration per proton, is 100:79.46 or 1:0.8. This sample also displayed multiplets at approximately 3.60 ppm and 1.75 ppm that correspond with 8 protons in THF. These peaks integrate to a total of 813.548. The ratio of Compound I/THF, based on integration per proton, is 100:101.69 or 1:1.

Figure 36:
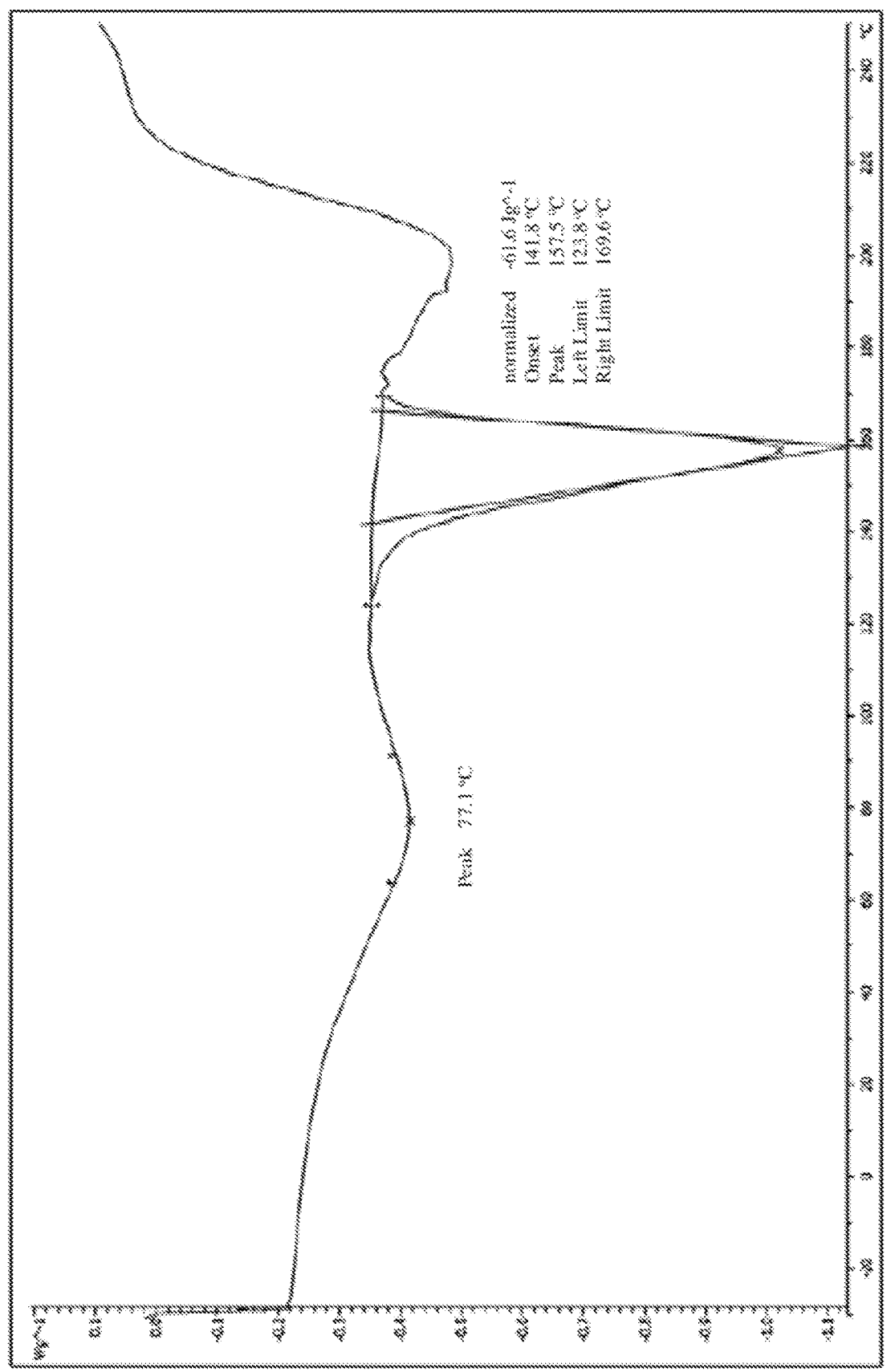
FIG. 36 shows a differential scanning calorimeter (DSC) curve of Compound I Napadisylate Material B.
Figure 37:
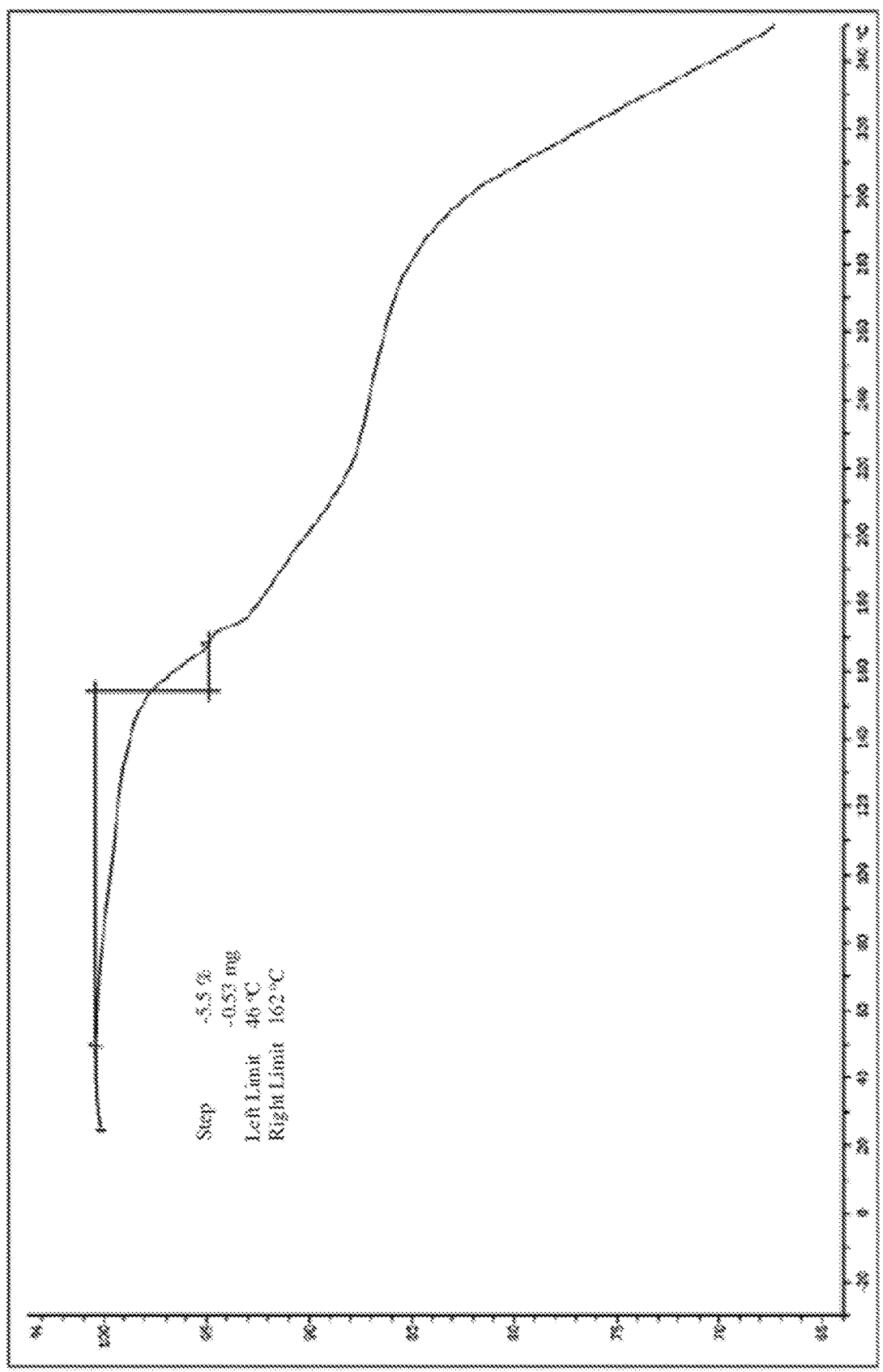
FIG. 37 shows a thermogravimetric analysis (TGA) of Compound I Napadisylate Material B.

Differential scanning calorimetry of the solvated sample showed two broad endotherms at 77.1° C. and 157.5° C. (FIG. 36). A 5.5% weight loss was seen by thermogravimetric analysis over 46 to 162° C. (FIG. 37). This was calculated to be consistent with 0.5 mol/mol THF.

Compound I Napsylate Form A

Solids of Compound I, prepared as described in Example 5 (98.3 mg), were combined with a naphthalene-2-sulfonic acid/THF solution (69.0 mg in 0.5 mL THF), and the resulting solution was left to stir at ambient temperature for 2 days, affording a yellow slurry. The slurry was centrifuged, and a clear solution was decanted from yellow solids. The solids were briefly dried under $N_2$. The resulting wet solids consisted of Compound I Napsylate Form A.

Figure 38:
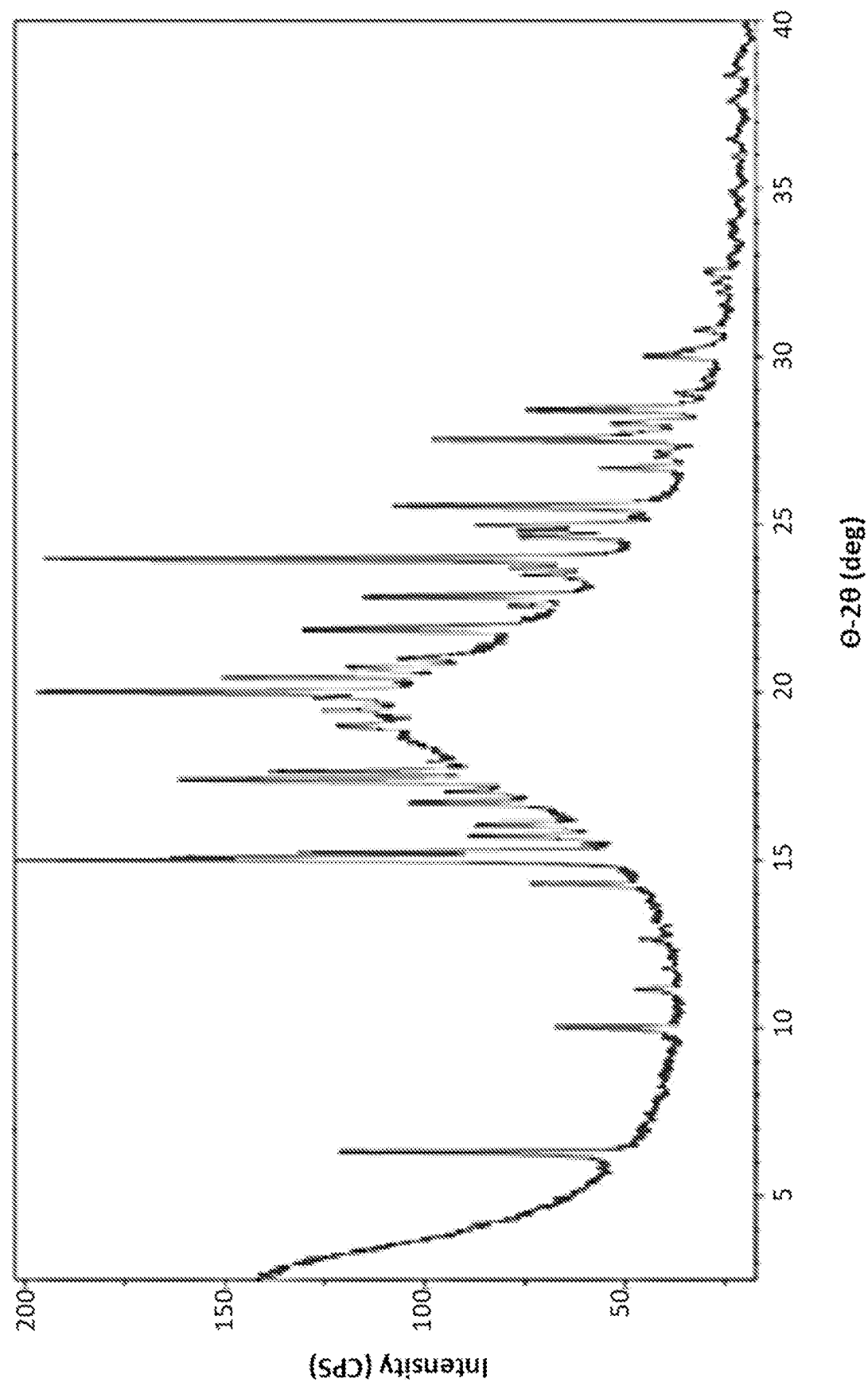
FIG. 38 shows an X-ray powder diffraction (XRPD) of Compound I Napsylate Form A.

Compound I Napsylate Form A consists of a THF solvate of a 1:1 napsylate salt of Compound I (FIG. 38). An XRPD pattern of the damp material was successfully indexed as a 1:1 napsylate with enough excess volume in the unit cell to contain at least 1 mol/mol of THF.

The stoichiometry of naphthalene-2-sulfonic acid in Compound I Napsylate Form A was shown by solution state proton nuclear magnetic resonance spectroscopy. The doublet at approximately 6.75 ppm corresponds with 1 proton in Compound I and integrates to 100. The singlet at approximately 8.14 ppm, multiplets at approximately 7.97 ppm & 7.90 ppm, and doublets at approximately 7.7 ppm, correspond with 4 protons in naphthalene-2-sulfonic acid. These peaks integrate to 986.947. The ratio of Compound I/naphthalene-2-sulfonic acid, based on integration per proton, is 100:246.74 or 1:2.5. This sample also displayed multiplets at approximately 3.60 ppm and 1.75 ppm that correspond with 8 protons in THF. These peaks integrate to a total of 2375.854. The ratio of Compound I/THF, based on integration per proton, is 100:297.0 or 1:3. Since the sample was damp with excess THF, this is not indicative of the solvent stoichiometry for Compound I Napsylate Form A.

Compound I Napsylate Material B

Solids of Compound I, prepared as described in Example 5 (120.4 mg), were combined with a naphthalene-2-sulfonic acid/THF solution (76.5 mg in 1 mL THF), and the resulting solution was left to stir at ambient temperature for 3 days, affording an off-white slurry. The slurry was filtered on a 0.2-μm nylon filter in a Swinnex filter holder. The solids were flushed with air (5×20 mL) on the filter. Resulting solids consisted of Compound I Napsylate Material B.

Figure 39:
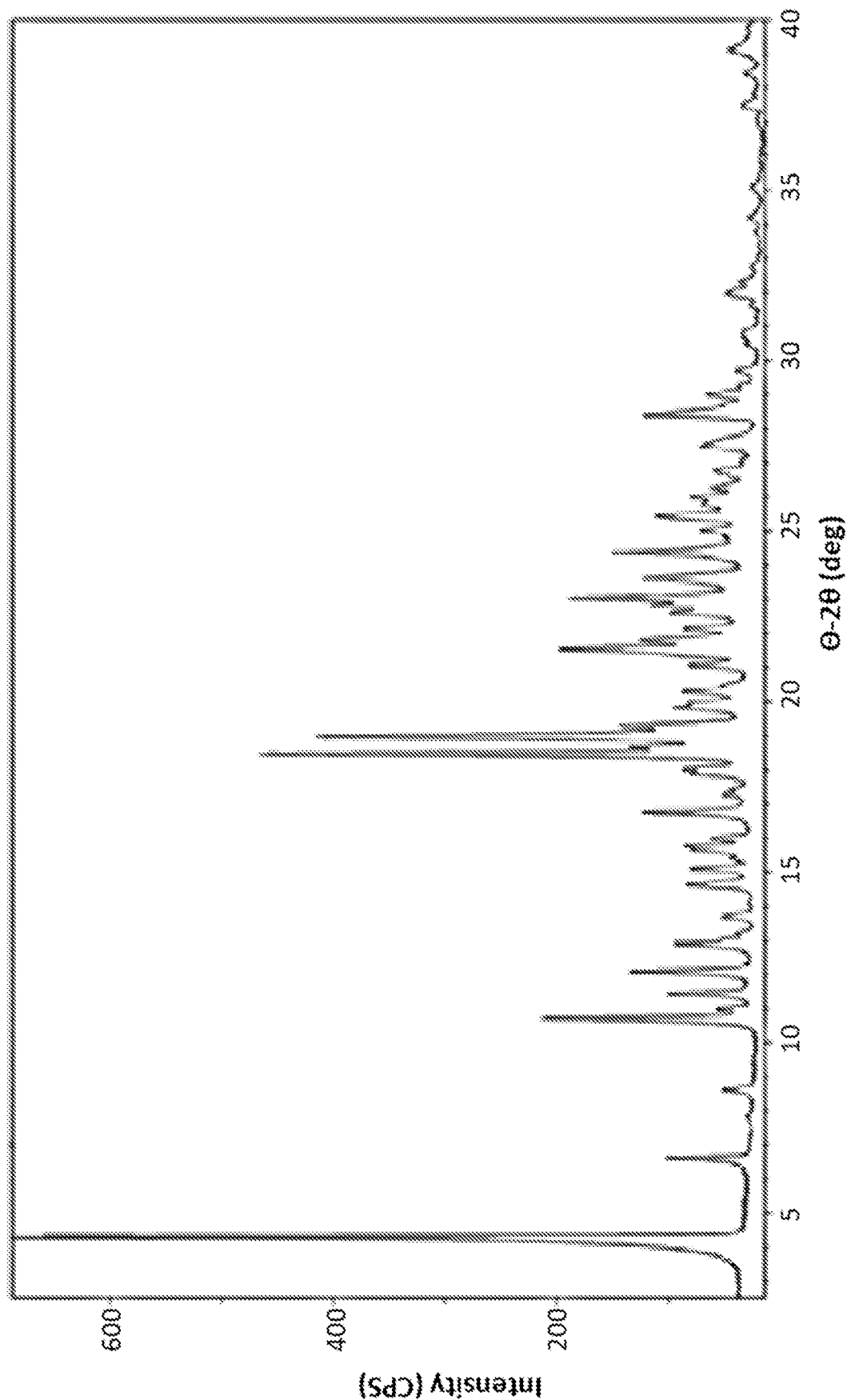
FIG. 39 shows an X-ray powder diffraction (XRPD) of Compound I Napsylate Material B.

Compound I Napsylate Material B consists of a potentially solvated 1:1 napsylate salt of Compound I (FIG. 39). The XRPD pattern of the material was not successfully indexed and phase purity could not be confirmed. NMR and TGA data suggest a possible THF solvate of 0.5 mol/mol or less.

The stoichiometry of naphthalene-1,5-disulfonic acid in Compound I Napsylate Material B was confirmed by solution state proton nuclear magnetic resonance spectroscopy. The doublet at approximately 6.75 ppm corresponds with 1 proton in Compound I and integrates to 100. The singlet at approximately 8.15 ppm, multiplets at approximately 7.97 ppm & 7.90 ppm, and doublets at approximately 7.71 ppm, correspond with 7 protons in naphthalene-2-sulfonic acid. These peaks integrate to 1030.08. The ratio of Compound I/naphthalene-2-sulfonic acid, based on integration per proton, is 100:147.15 or 1:1.5. This sample also displayed multiplets at approximately 3.60 ppm and 1.75 ppm that correspond with 8 protons in THF. These peaks integrate to a total of 428.23. The ratio of Compound I/THF, based on integration per proton, is 100:53.529 or 1:0.5.

Figure 40:
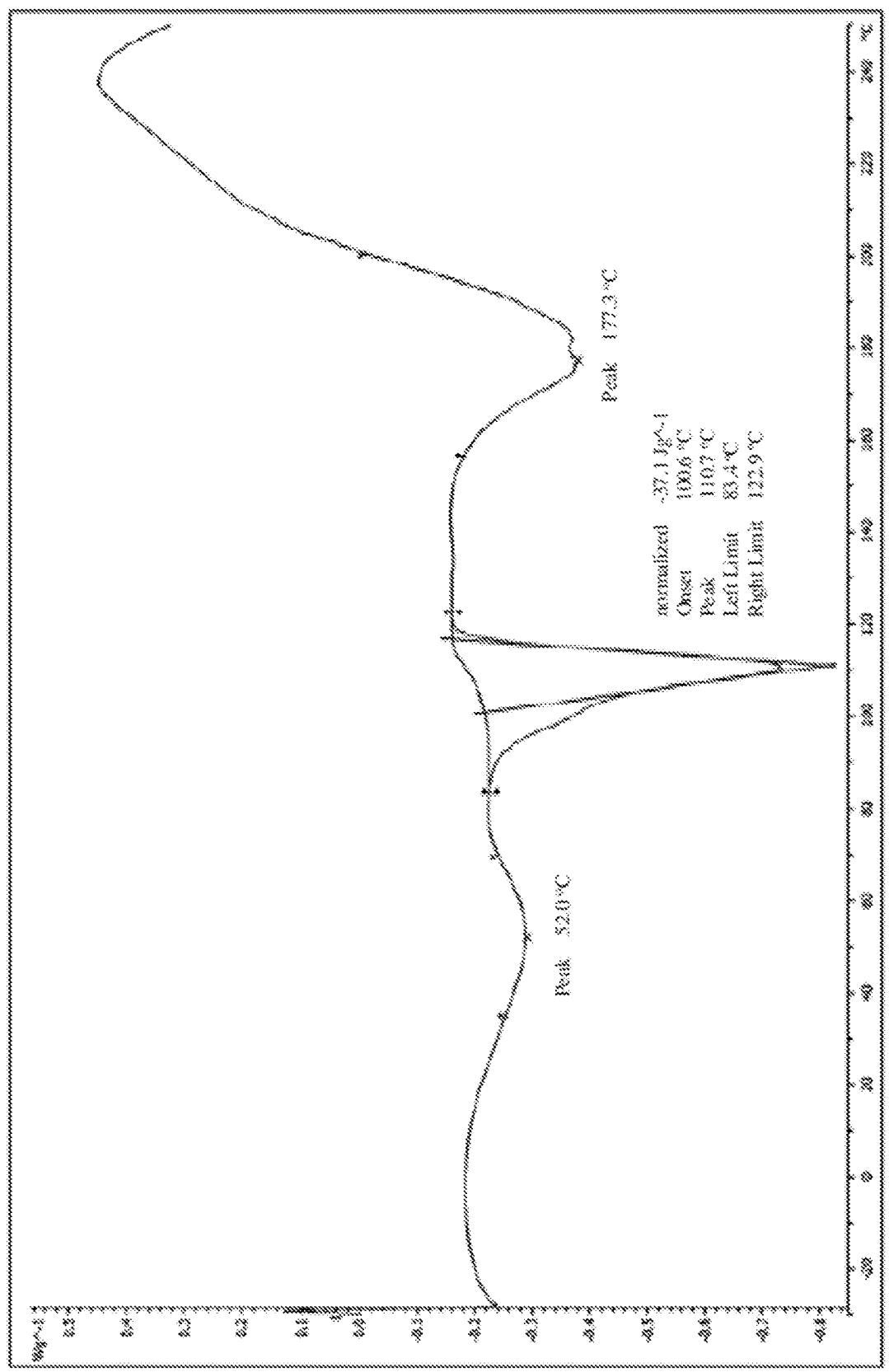
FIG. 40 shows a differential scanning calorimeter (DSC) curve of Compound I Napsylate Material B.
Figure 41:
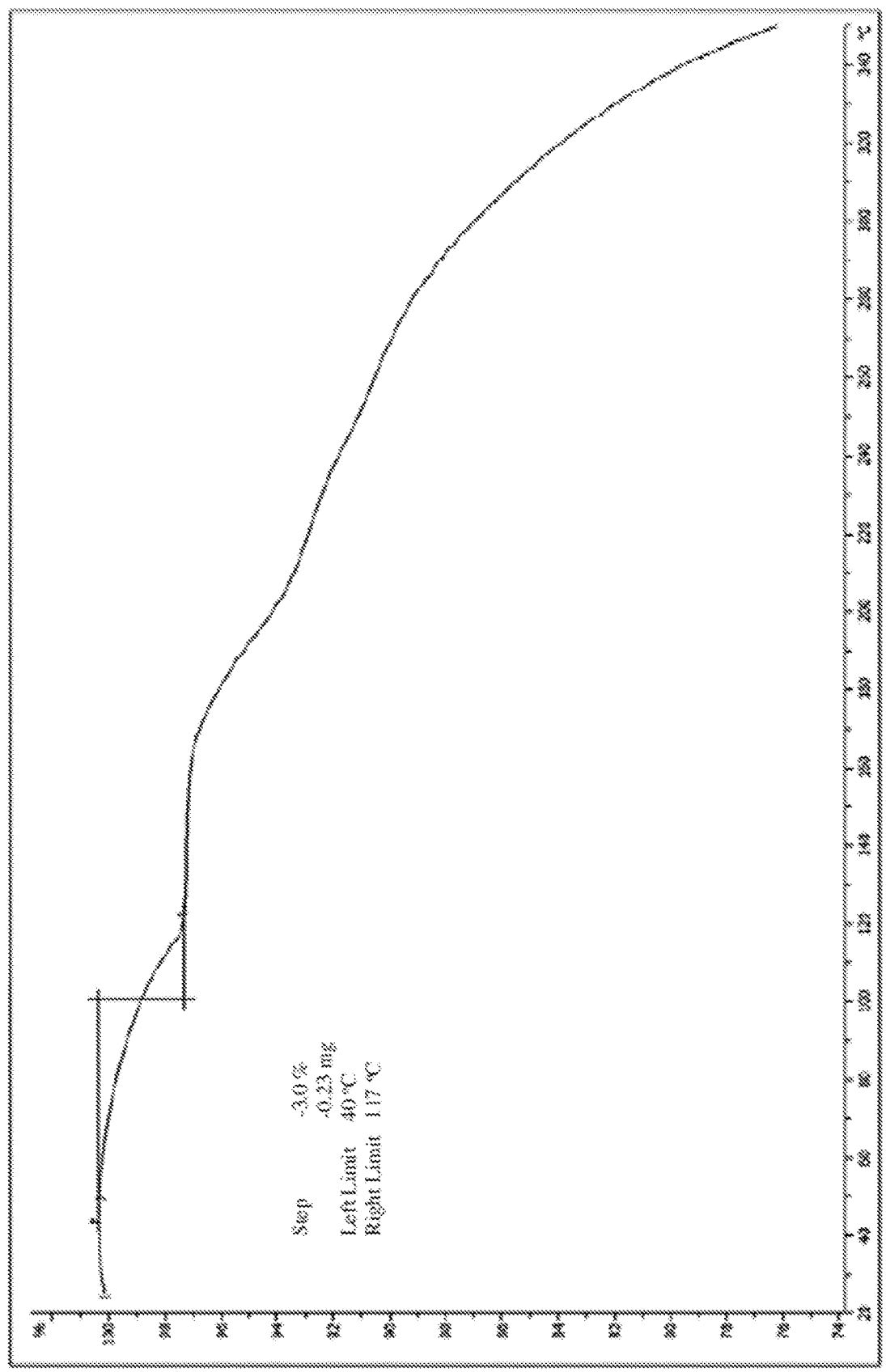
FIG. 41 shows a thermogravimetric analysis (TGA) of Compound I Napsylate Material B.

Differential scanning calorimetry of the sample showed three broad endotherms at 52.0° C., 110.7° C., and 177.3° C. (FIG. 40). A 3.0% weight loss was seen by thermogravimetric analysis over 40 to 117° C. (FIG. 41). This weight loss was calculated to be 0.26 mol/mol THF.

Compound I Oxalate Material A

A solution of oxalic acid in EtOH (23.9 mg in 1 mL EtOH) was added to solids of Compound I, prepared as described in Example 5 (98.8 mg). The off-white slurry was stirred for 2 days. The slurry was filtered on a 0.2-μm nylon filter in a Swinnex filter holder. The solids were flushed with air (5×20 mL) on the filter. Resulting solids consisted of Compound I Oxalate Material A.

Figure 42:
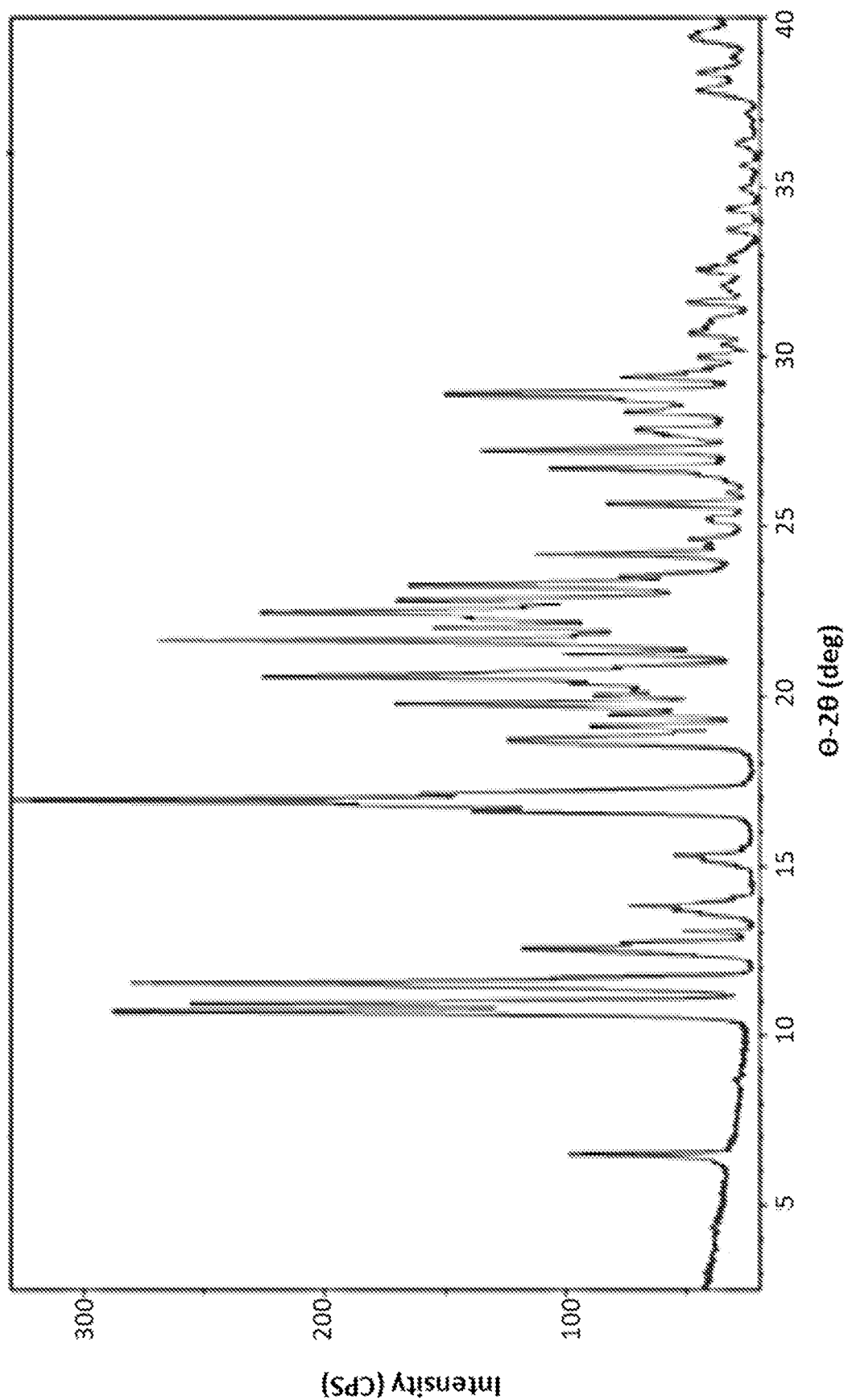
FIG. 42 shows an X-ray powder diffraction (XRPD) of Compound I Oxalate Material A.

Compound I Oxalate Material A likely consists of an unsolvated hemi-oxalate salt of Compound I (FIG. 42). The XRPD pattern of the material was not successfully indexed and phase purity could not be confirmed. Although physical stability was not evaluated, weight loss in the thermogravimetric analysis suggests Compound I Oxalate Material A is hygroscopic.

The stoichiometry of oxalic acid in Compound I Oxalate Material A was confirmed by ion chromatography to contain 0.42 mol/mol oxalate ion. Solution state proton nuclear magnetic resonance spectroscopy was consistent with the chemical structure of Compound I with no residual organic solvent evident.

Figure 43:
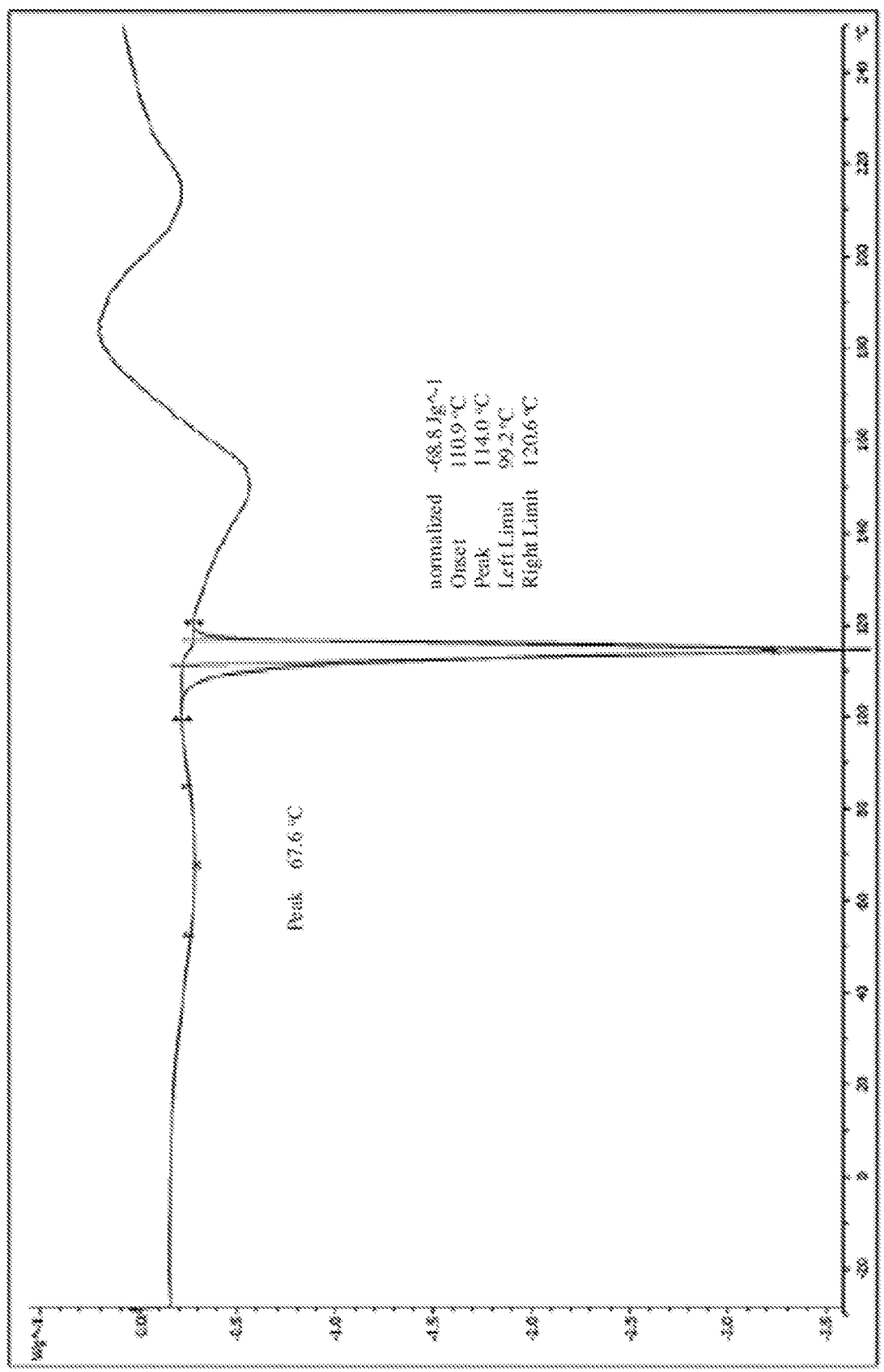
FIG. 43 shows a differential scanning calorimeter (DSC) curve of Compound I Oxalate Material A.
Figure 44:
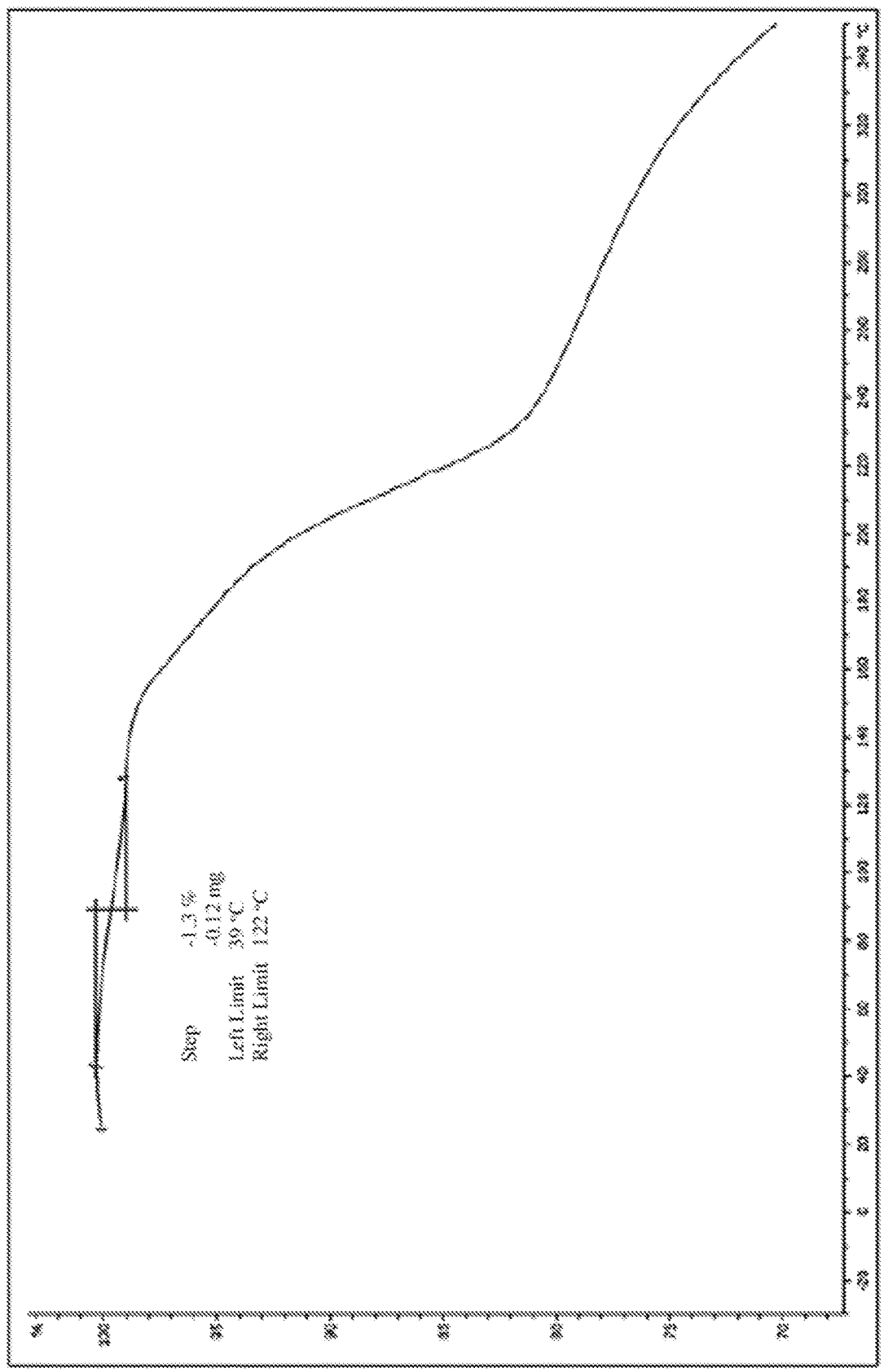
FIG. 44 shows a thermogravimetric analysis (TGA) of Compound I Oxalate Material A.

Differential scanning calorimetry of the sample displayed a broad, shallow endotherm at 67.6° C. and a sharp endotherm with an onset at 110.9° C. (FIG. 43). A 1.3% weight loss was observed by thermogravimetric analysis over 39 to 122° C. (FIG. 44). Since no residual solvent was observed by NMR, this weight loss is likely due to water, and suggests Compound I Oxalate Material A may be hygroscopic.

Compound I Oxalate Form B

A solution of oxalic acid in acetone (26.1 mg in 0.5 mL acetone) was added to solids of Compound I, prepared as described in Example 5 (106.1 mg). The clear yellow solution was stirred for 1 day, resulting in an off-white slurry. The slurry was filtered on a 0.2-µm nylon filter in a Swinnex filter holder. The solids were flushed with air (5×20 mL) on the filter. Resulting solids consisted of Compound I Oxalate Form B.

The XRPD pattern of Compound I Oxalate Form B (FIG. 45) was successfully indexed with a unit cell volume consistent with an unsolvated 1:1 oxalate salt. Physical stability of Compound I Oxalate Form B was assessed under high humidity conditions. At 90% RH and ambient temperature, the material was still predominately Compound I Oxalate Form B after 11 days (data not shown). One additional peak was noted in the XRPD pattern at 16.96° (2θ).

The aqueous solubility of Compound I Oxalate Form B was shown to be greater than 134 mg/mL.

The stoichiometry of oxalic acid in Compound I Oxalate Form B was confirmed by ion chromatography to be a 1:1 molar ratio of anion to Compound I. Solution state proton nuclear magnetic resonance spectroscopy was used to confirm the chemical structure of Compound I. No appreciable amounts of residual organic solvent were evident in the NMR.

Figure 46:
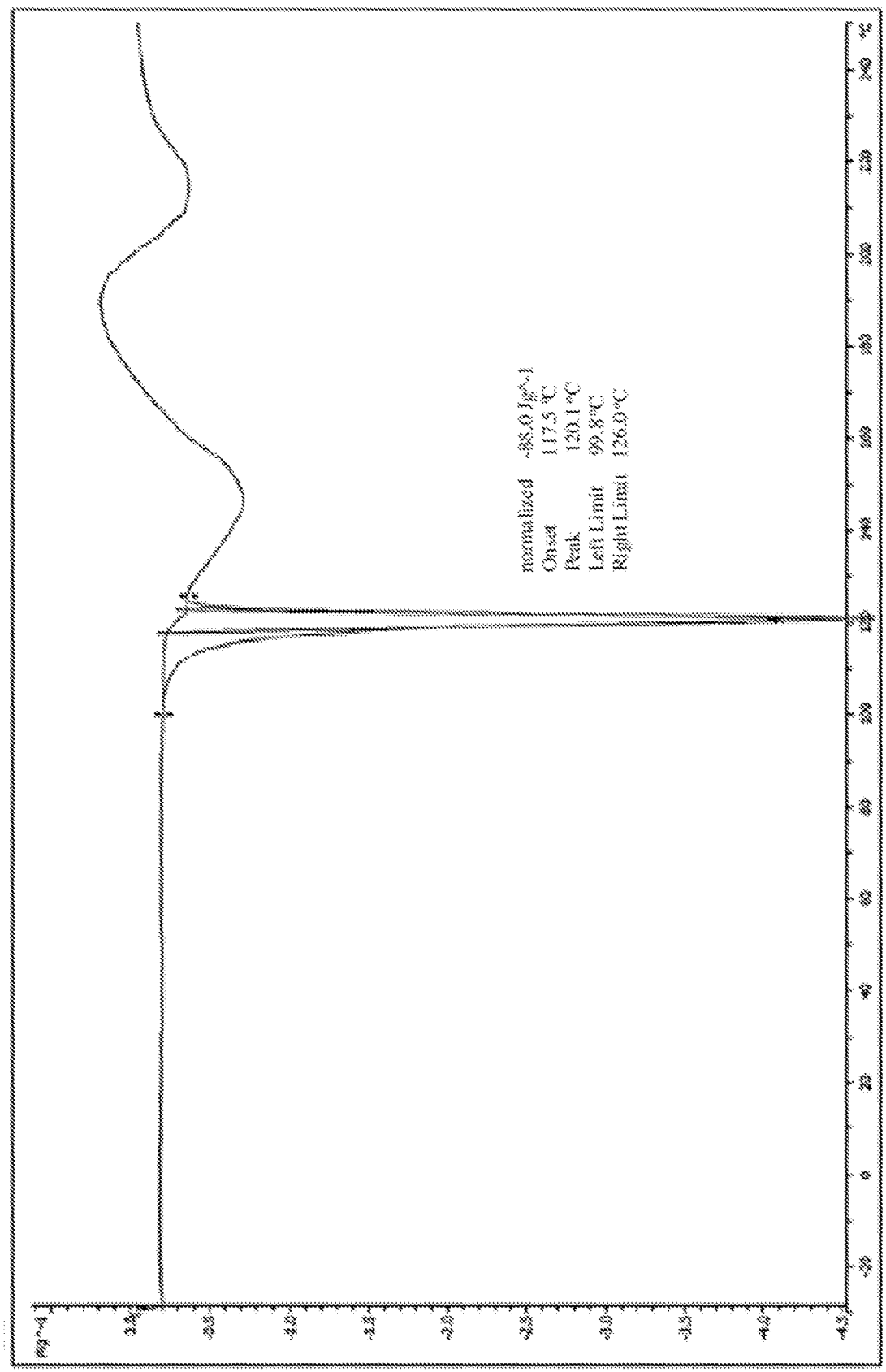
FIG. 46 shows a differential scanning calorimeter (DSC) curve of Compound I Oxalate Form B.
Figure 47:
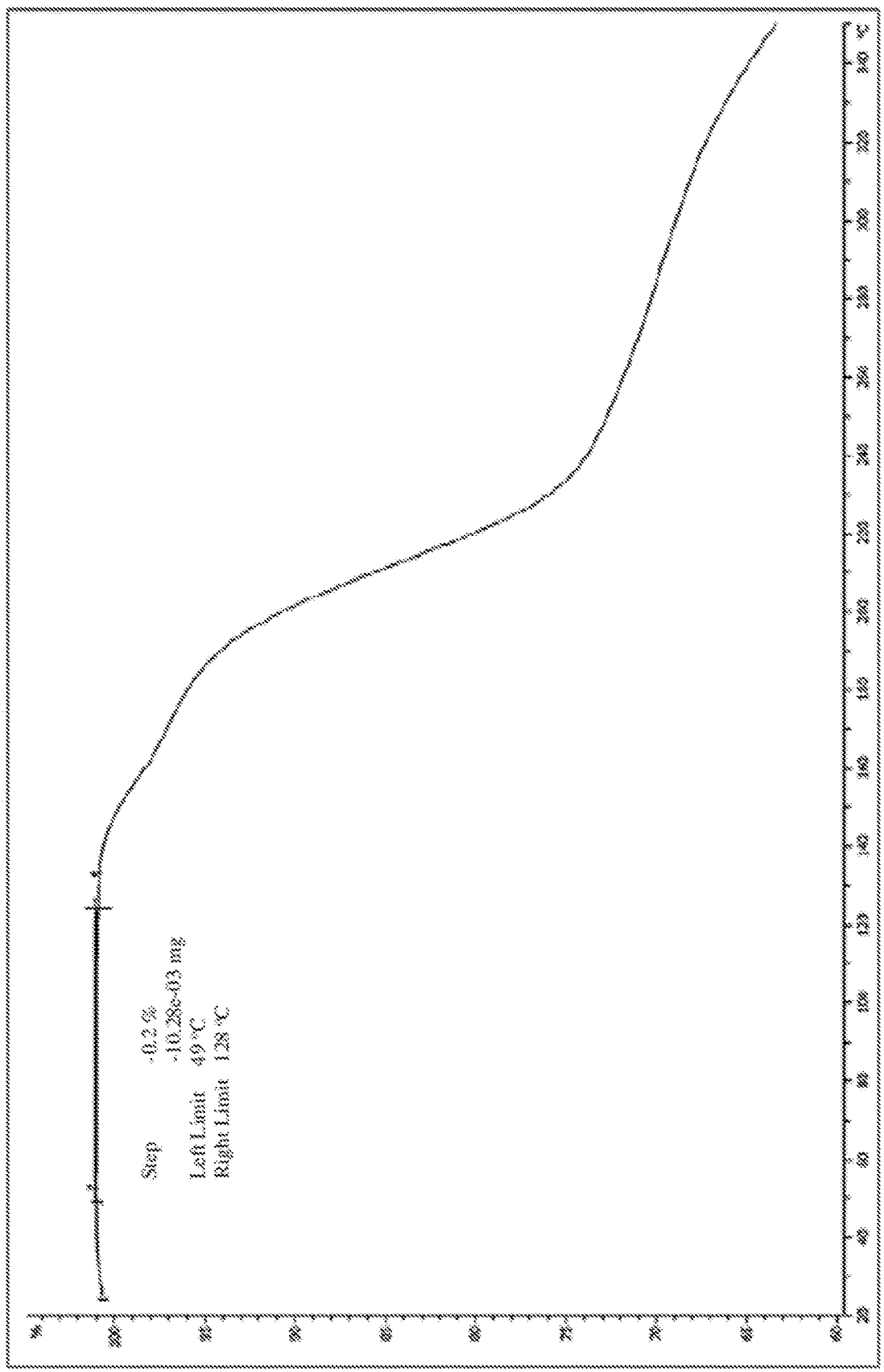
FIG. 47 shows a thermogravimetric analysis (TGA) of Compound I Oxalate Form B.

Differential scanning calorimetry of the sample showed a sharp endotherm with an onset of 117.5° C. (FIG. 46). Only 0.2% weight loss was observed by thermogravimetric analysis over 49 to 128° C., consistent with an anhydrous/unsolvated form (FIG. 47). This was followed by decomposition.

Compound I Sulfate Form A

Solids of Compound I, prepared as described in Example 5 (99.1 mg), were slurried in IPA (2 mL) at ambient temperature. Sulfuric acid (14.5 µL) was added to the slurry. The mixture was stirred for 5 days resulting in a pale pink slurry. The slurry was filtered on a 0.2-µm nylon filter in a Swinnex filter holder. The solids were flushed with air (5×20 mL) on the filter. The resulting damp pink solids were further dried in a 43° C. vacuum oven over 2 days. The dry solids consisted of Compound I Sulfate Form A.

Figure 48:
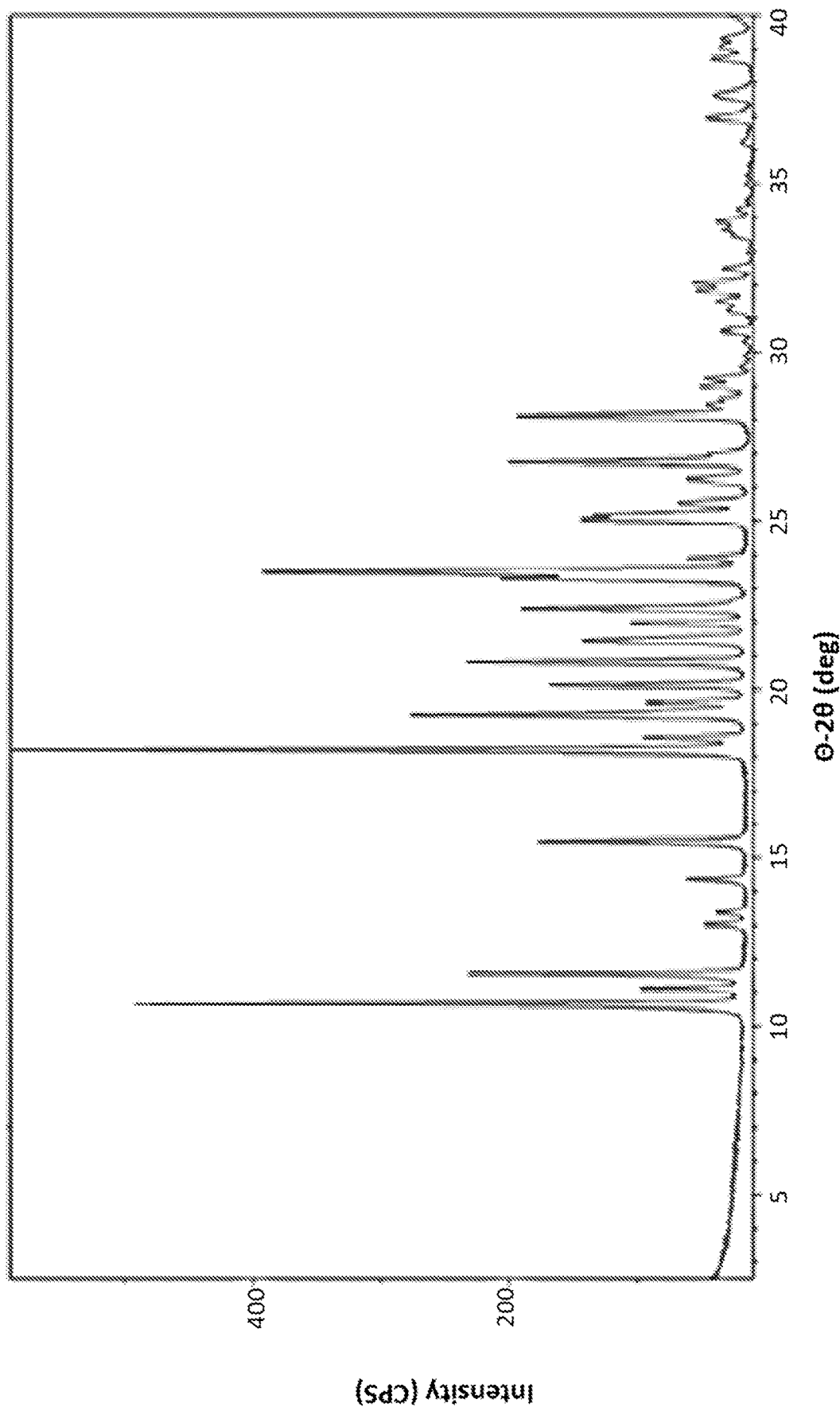
FIG. 48 shows an X-ray powder diffraction (XRPD) of Compound I Sulfate Form A.

Compound I Sulfate Form A consists of an unsolvated 1:1 sulfate salt of Compound I (FIG. 48). The XRPD pattern of the material was successfully indexed with a unit cell volume consistent with an unsolvated 1:1 sulfate. Compound I Sulfate Form A was shown to be physically stable by XRPD under vacuum at 43° C. for 2 days. However, the salt was shown to be hygroscopic and deliquesces at 90% RH at ambient temperature within 1 day.

Compound I Sulfate Form A exhibits an aqueous solubility greater than 87 mg/mL.

The stoichiometry of sulfuric acid in Compound I Sulfate Form A was confirmed by ion chromatography to be a 1:1 molar ratio of Compound I to anion. Solution state proton nuclear magnetic resonance spectroscopy was used to confirm the chemical structure of Compound I. No appreciable amounts of residual organic solvent were evident in the NMR.

Figure 49:
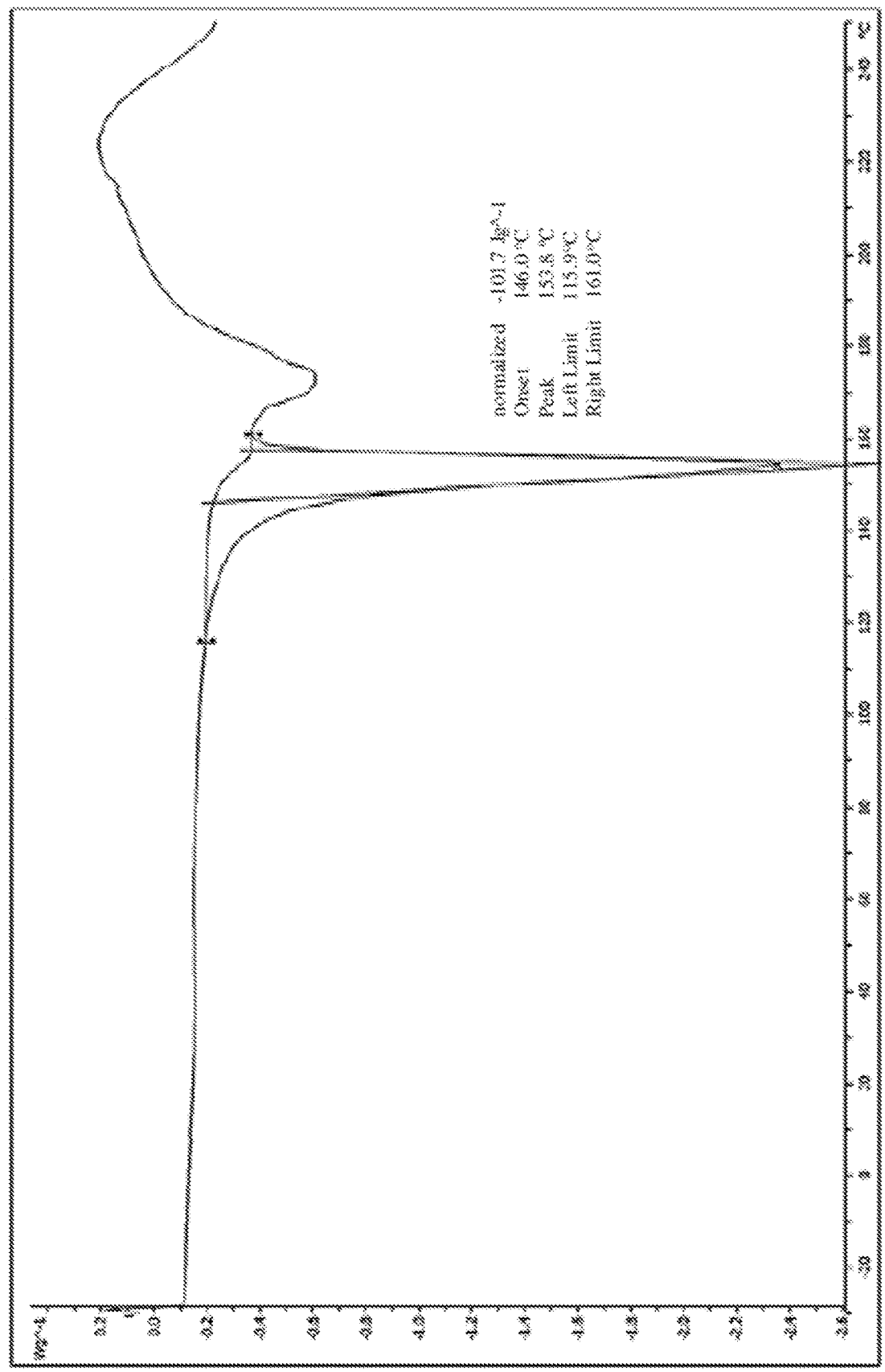
FIG. 49 shows a differential scanning calorimeter (DSC) curve of Compound I Sulfate Form A.
Figure 50:
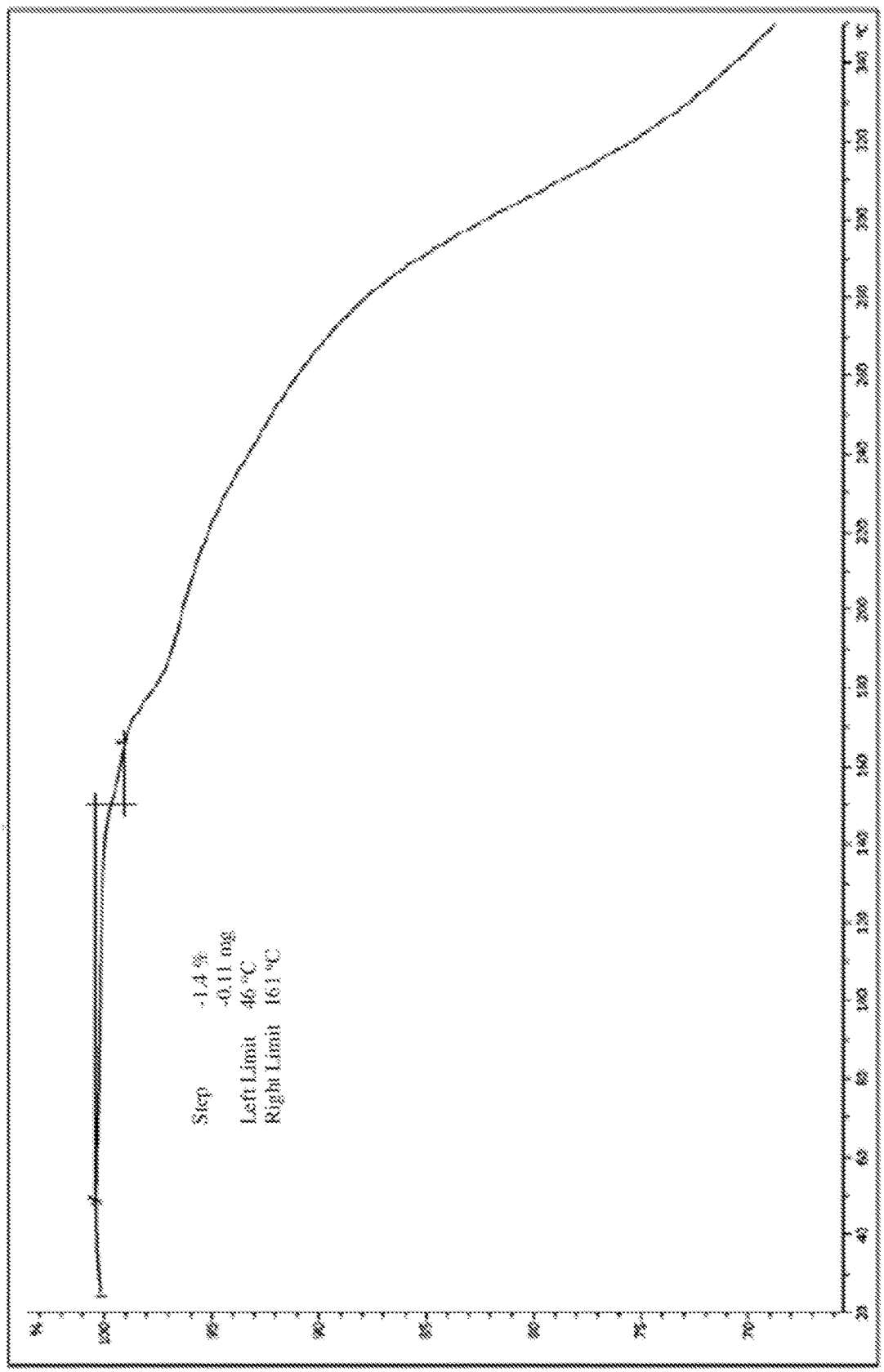
FIG. 50 shows a thermogravimetric analysis (TGA) of Compound I Sulfate Form A.

Differential scanning calorimetry of the sample showed a sharp endotherm with an onset of 146.0° C. (FIG. 49). Only 1.4% weight loss was observed by thermogravimetric analysis over 46 to 161° C. (FIG. 50). This was followed by decomposition. Since no solvent was observed in the NMR, this weight loss is likely due to water, and suggests Compound I Sulfate Form A may be hygroscopic.

Compound I Tosylate Form A

Solids of Compound I, prepared as described in Example 5 (92.3 mg), were combined with a p-toluenesulfonic acid monohydrate/THF solution (46.7 mg in 0.5 mL THF), and the resulting solution was left to stir at ambient temperature for 3 days, affording a thick off-white slurry. The slurry was filtered on a 0.2-µm nylon filter in a Swinnex filter holder. The solids were flushed with air (5×20 mL) on the filter. Resulting solids consisted of Compound I Tosylate Form A.

Figure 51:
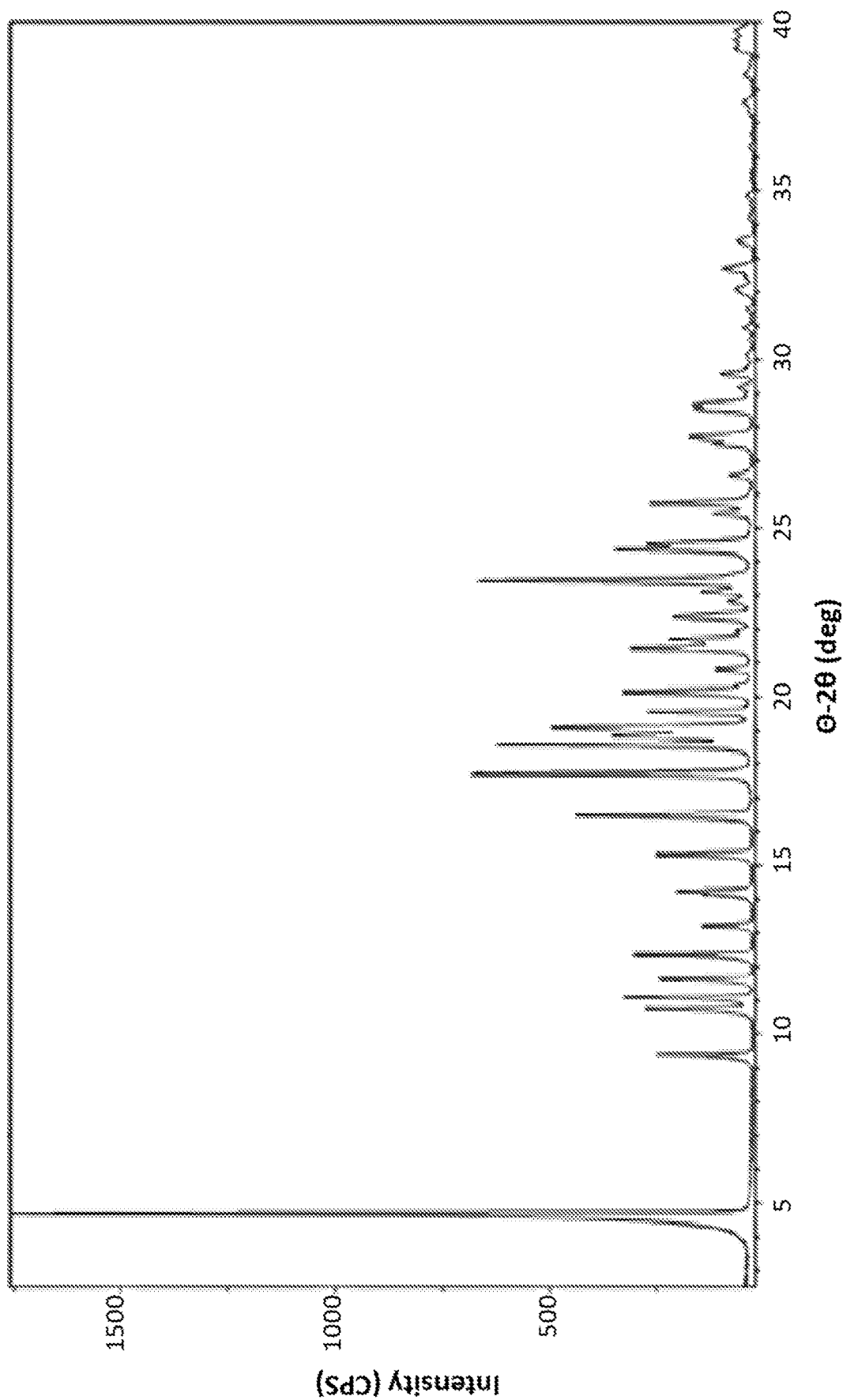
FIG. 51 shows an X-ray powder diffraction (XRPD) of Compound I Tosylate Form A.

Compound I Tosylate Form A consists of a 1:1 tosylate salt of Compound I (FIG. 51). Compound I Tosylate Form A appears to be a hemiTHF solvate; however, the unit cell volume is variable and likely compensates for differences in solvent content. An XRPD pattern (data not shown) displayed peak shifting to the right for the sample that was exposed to 44° C. under vacuum, associated with a decrease in the volume of the unit cell. The crystal structure is isostructural with Compound I Besylate Form A and Compound I Esylate Forms A & B.

The stoichiometry of p-toluenesulfonic acid in Compound I Tosylate Form A was confirmed by solution state proton nuclear magnetic resonance spectroscopy. The doublet at approximately 6.75 ppm corresponds with 1 proton in Compound I and integrates to 100. The doublets at approximately 7.45 ppm and 7.13 ppm, and the singlet at 2.29 ppm, correspond with 7 protons in p-toluenesulfonic acid. These peaks integrate to a total of 788.20. The ratio of Compound I/p-toluenesulfonic acid, based on integration per proton, is 100:112.6 or 1:1.1. This sample also displayed multiplets at approximately 3.60 ppm and 1.75 ppm that correspond with 8 protons in THF. These peaks integrate to a total of 400.61. The ratio of Compound I/THF, based on integration per proton, is 100:50.08 or 1:0.5.

Figure 52:
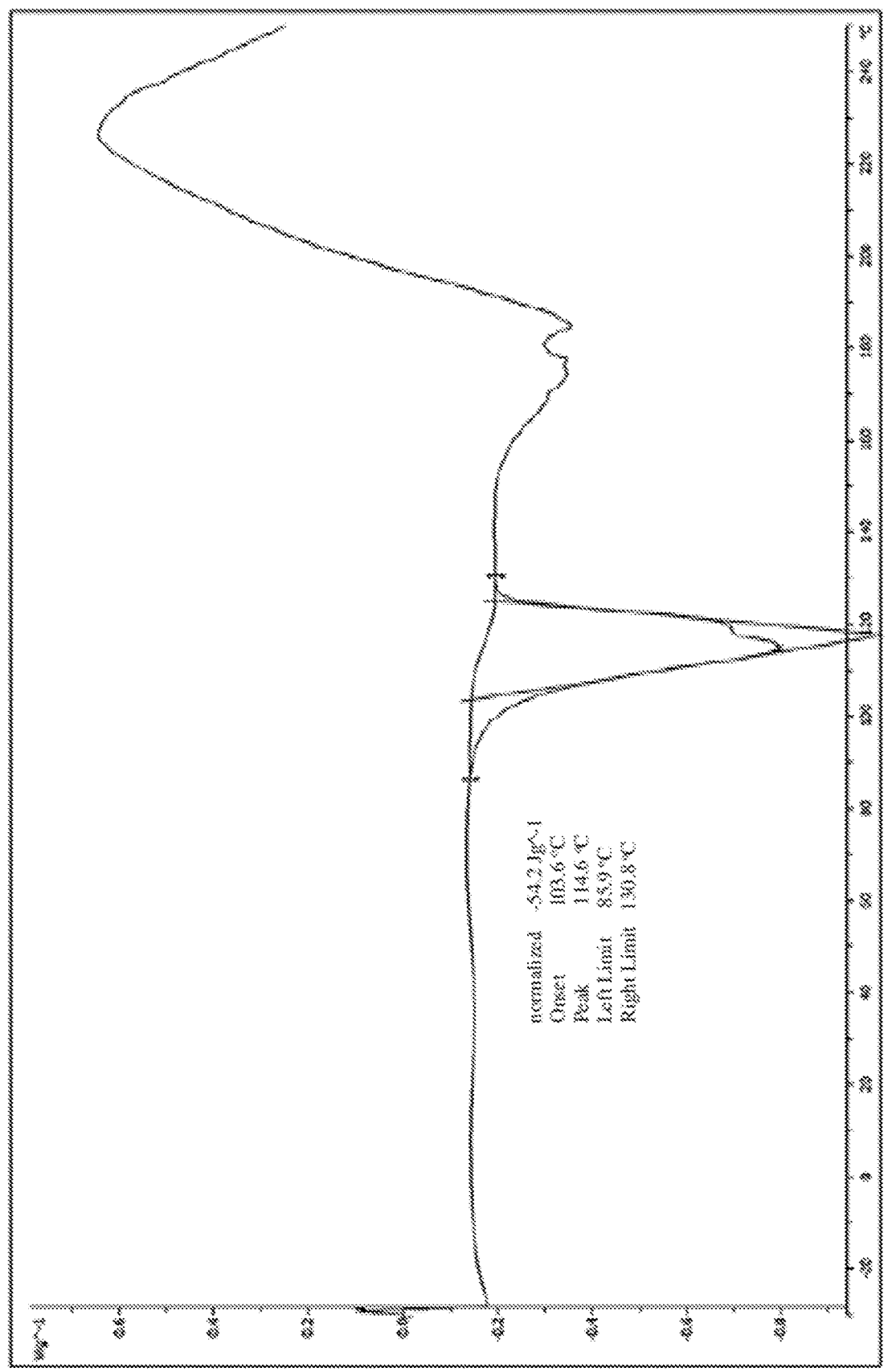
FIG. 52 shows a differential scanning calorimeter (DSC) curve of Compound I Tosylate Form A.

Differential scanning calorimetry of the solvated sample showed overlapping broad endotherms at 114.6° C. (FIG. 52). A weight loss of 3.3% was observed by TGA over 43 to 137° C. (FIG. 53), consistent with 0.3 mol THF/mol Compound I. The discrepancy between the amount of THF present in the NMR and the TGA is due to the variability allowed in the unit cell, as previously discussed.

Biological Assays

The crystalline forms as described above can be tested in published assays for biological activity, such as, but not limited to, those described in U.S. Pat. No. 10,683,285.

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

What is claimed is:

1. A crystalline Compound I Form I having the formula:

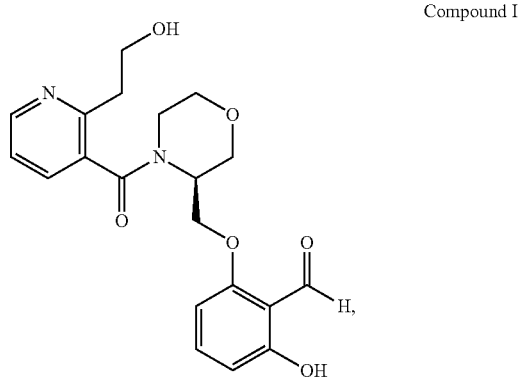

Compound I characterized by an X-ray powder diffractogram comprising diffraction peaks 10.8±0.2, 17.3±0.2, 17.5±0.2, 18.3±0.2, 23.4±0.2, 23.7±0.2, and 26.1±0.2 °2θ, as determined on a diffractometer using Cu-Kα radiation.

2. The crystalline Compound I Form I of claim 1, wherein the crystalline Compound I Form I is characterized by the X-ray powder diffractogram as substantially shown in FIG. 1.

3. The crystalline Compound I Form I of claim 1, wherein the crystalline Compound I Form I is characterized by a differential scanning calorimetry (DSC) curve that comprises an endotherm at about 111° C.

4. The crystalline Compound I Form I of claim 1, wherein the crystalline Compound I Form I is characterized by the DSC curve as substantially shown in FIG. 2A.

5. The crystalline Compound I Form I of claim 1, having unit cell parameters: a=5.50599(10) Å, b=16.4086(2) Å, c=20.4992(4) Å, α=90°, β=90°, γ=90°, and volume=1852.02(5) Å³.

6. A crystalline Compound I Material II having the formula:

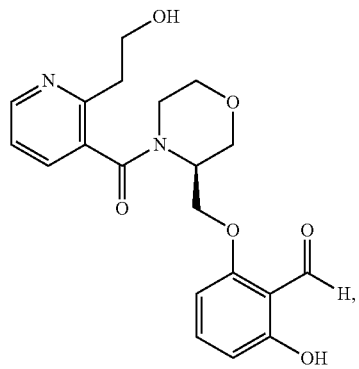 [SMILES: O=Cc1c(O)cccc1OC[C@@H]1COCCN1C(=O)c1cccnc1CCO ; "·X"]

Compound I characterized by an X-ray powder diffractogram comprising diffraction peaks 14.9±0.2, 16.7±0.2, 18.4±0.2, 18.6±0.2, 19.2±0.2, 19.6±0.2, 20.2±0.2, 22.9±0.2, and 25.8±0.2 °2θ, as determined on a diffractometer using Cu-Kα radiation.

7. The crystalline Compound I Material II of claim 6, wherein the crystalline Compound I Material II is characterized by the X-ray powder diffractogram as substantially shown in FIG. 5.

8. The crystalline Compound I Material II of claim 6, wherein the crystalline Compound I Material II is characterized by a differential scanning calorimetry (DSC) curve that comprises an endotherm at about 102° C.

9. The crystalline Compound I Material II of claim 6, wherein the crystalline Compound I Material II is characterized by the DSC curve as substantially shown in FIG. 6.

10. A crystalline Compound I HCl Form A having the formula:

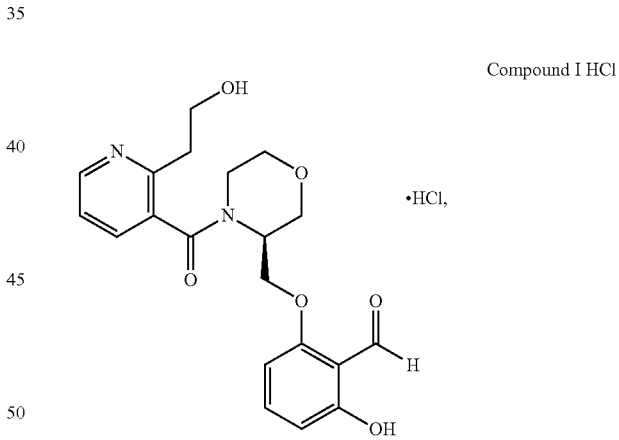

Compound I HCl characterized by an X-ray powder diffractogram comprising diffraction peaks 12.7±0.2, 16.4±0.2, 16.7±0.2, 18.5±0.2 and 23.5±0.2 °2θ, as determined on a diffractometer using Cu-Kα radiation.

11. The crystalline Compound I HCl Form A of claim 10, wherein the crystalline Compound I HCl Form A is characterized by the X-ray powder diffractogram as substantially shown in FIG. 9.

12. The crystalline Compound I HCl Form A of claim 10 wherein the crystalline Compound I HCl Form A is characterized by a differential scanning calorimetry (DSC) curve that comprises an endotherm at about 193° C.

13. The crystalline Compound I HCl Form A of claim 10, wherein the crystalline Compound I HCl Form A is characterized by the DSC curve as substantially shown in FIG. 10.

14. A pharmaceutical composition comprising the crystalline Compound I Form I of claim 1 and a pharmaceutically acceptable excipient.

15. A pharmaceutical composition comprising a pharmaceutically acceptable excipient, the crystalline Compound I Form I of claim 1, and another therapeutic agent.

16. A method for increasing oxygen affinity of hemoglobin S in a subject in need thereof, comprising administering to the subject the crystalline Compound I Form I of claim 1.

17. A method for treating a disorder mediated by hemoglobin in a subject in need thereof, comprising administering to the subject the crystalline Compound I Form I of claim 1.

18. The method of claim 17, wherein the hemoglobin is sickle hemoglobin.

19. A method for treating sickle cell disease in a subject in need thereof, comprising administering to the subject the crystalline Compound I Form I of claim 1.

* * * * *